United States Patent
Waterman et al.

(10) Patent No.: US 9,637,542 B2
(45) Date of Patent: May 2, 2017

(54) CX3CR1-TARGETING IMAGING AGENTS AND THEIR USE IN THE DIAGNOSIS AND TREATMENT OF DISEASE

(71) Applicants: Alisa K. Waterman, Weston, CT (US); Nick Mark Devoogdt, Zemst (BE); Tony Lahoutte, Ganshoren (BE); Matthias Schneider, Bethel, CT (US); Sanjaya Singh, Sandy Hook, CT (US); Cedric Jozef Néotère Ververken, Merelbeke (BE)

(72) Inventors: Alisa K. Waterman, Weston, CT (US); Nick Mark Devoogdt, Zemst (BE); Tony Lahoutte, Ganshoren (BE); Matthias Schneider, Bethel, CT (US); Sanjaya Singh, Sandy Hook, CT (US); Cedric Jozef Néotère Ververken, Merelbeke (BE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 217 days.

(21) Appl. No.: 14/463,689

(22) Filed: Aug. 20, 2014

(65) Prior Publication Data
US 2015/0056133 A1    Feb. 26, 2015

Related U.S. Application Data

(60) Provisional application No. 61/868,144, filed on Aug. 21, 2013.

(51) Int. Cl.
| | |
|---|---|
| A61K 51/10 | (2006.01) |
| C07K 16/28 | (2006.01) |
| A61K 49/00 | (2006.01) |
| A61K 49/04 | (2006.01) |
| A61K 49/22 | (2006.01) |
| G01N 33/569 | (2006.01) |

(52) U.S. Cl.
CPC .......... *C07K 16/28* (2013.01); *A61K 49/0058* (2013.01); *A61K 49/04* (2013.01); *A61K 49/221* (2013.01); *A61K 51/10* (2013.01); *A61K 51/1021* (2013.01); *A61K 51/1093* (2013.01); *G01N 33/56966* (2013.01)

(58) Field of Classification Search
CPC ........ A61K 39/39533; A61K 39/39541; A61K 39/3955; A61K 49/0058; A61K 51/1027; A61K 51/1033; A61K 51/1093; C07K 16/28; C07K 16/2866
See application file for complete search history.

(56) References Cited

U.S. PATENT DOCUMENTS

| | | | | |
|---|---|---|---|---|
| 9,035,029 | B2 * | 5/2015 | Singh | C07K 16/2866 424/143.1 |
| 2002/0192212 | A1 * | 12/2002 | Imai | C07K 16/24 424/140.1 |
| 2005/0069962 | A1 * | 3/2005 | Archer | B82Y 5/00 435/7.9 |
| 2006/0160076 | A1 * | 7/2006 | Moodie | C07K 14/521 435/6.11 |
| 2011/0085969 | A1 * | 4/2011 | Rollo | A61K 51/0491 424/1.41 |
| 2011/0182897 | A1 * | 7/2011 | Hultberg | C07K 16/10 424/134.1 |
| 2012/0141471 | A1 * | 6/2012 | Salvino | C07D 487/04 424/133.1 |

FOREIGN PATENT DOCUMENTS

| | | |
|---|---|---|
| WO | WO 2005/103684 A2 * | 11/2005 |
| WO | 2010070394 A1 | 6/2010 |
| WO | WO 2013/130381 A1 * | 9/2013 |

OTHER PUBLICATIONS

International Search Report and Written Opinion, Form PCT/ISA/220, for PCT/US2014/051779, mailed Nov. 14, 2014.
Chen, et al., Department of Immunology, "In Vivo Inhibition of CC and CX3C Chemokine-Induced Leukocyte Infiltration and Attenuation of Glomerulonephritis in Wistar-Kyoto Rats by vMIP-II", 1998, p. 193-198.
Combadiere, et al., The Journal of Biological Chemistry, "Identification of CX3CR1: A Chemotactic Receptor for the Human CX 3C Chemokine Fractalkine and a Fusion Coreceptor for HIV-1", 1998.
Liu, et al., The Journal of Nuclear Medicine, "PET Imaging of Chemokine Receptors in Vascular Injury-Acelerated Atherosclerosis", 2013.
Sawai, et al., Arthritis and Rheumatism, "T Cell Costimulation by Fractaline-Expressing Synoviocytes in Rheumatoid Arthritis", 2005.

* cited by examiner

*Primary Examiner* — Jeffrey E Russel
(74) *Attorney, Agent, or Firm* — Michael P. Morris; Atabak R. Royaee

(57) ABSTRACT

The present invention relates to CX3CR1-targeting imaging agents and their use in treatment and diagnosis of diseases. Single domain CX3CR1-targeting polypeptides linked to detection labels and their use in in vivo imaging of atherosclerotic plaques are described. The CX3CR1-targeting imaging agents are useful in the treatment and diagnosis of CX3CR1-mediated diseases including atherosclerosis.

16 Claims, 6 Drawing Sheets
(3 of 6 Drawing Sheet(s) Filed in Color)

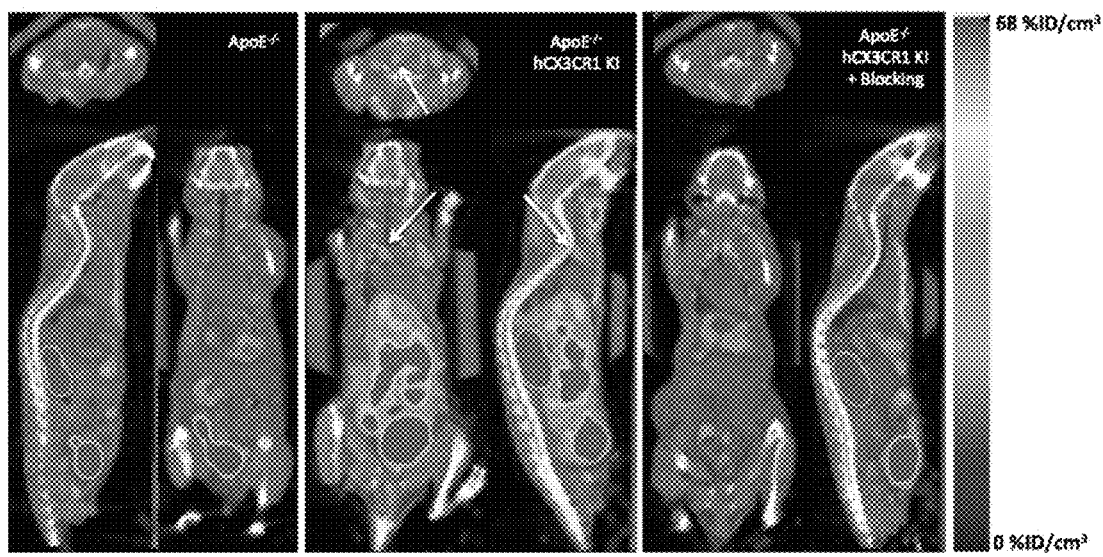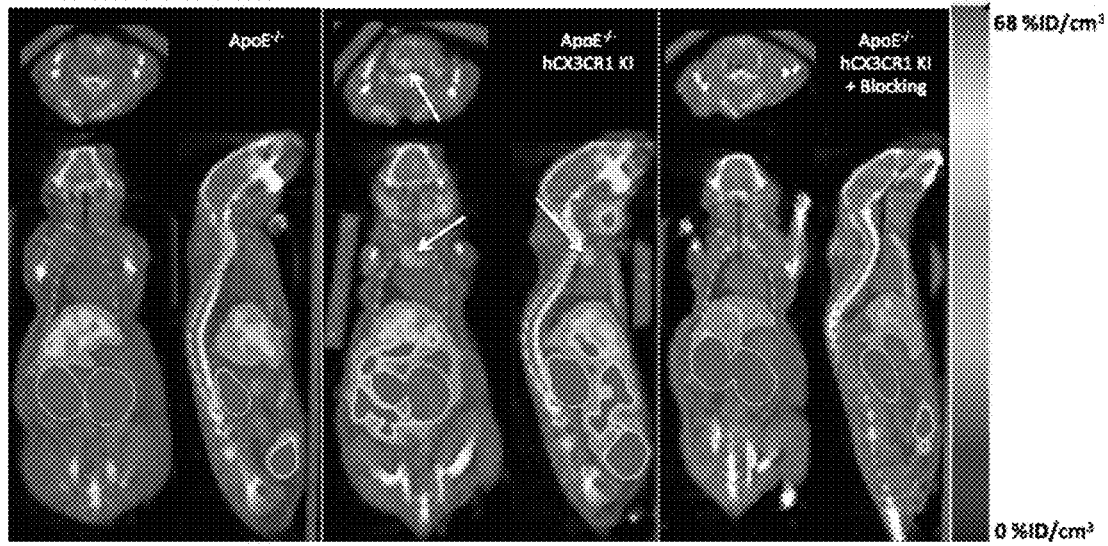
Fig.3

ER

SEQUENCE LISTING

<160> NUMBER OF SEQ ID NOS: 235

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Arg Arg Asp Leu Val
            35                  40                  45

Ala Ala Ile Asn Ser Val Gly Val Thr Lys Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Val Ile Asn Ser Val Gly Ile Thr Lys Tyr Ala Asp Ser Val Lys
        50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 3

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Arg Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 5
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

```
Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Leu Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Ser Val Gln Ala Gly Glu
 1               5                  10                  15

Ser Leu Arg Leu Ser Cys Ala Ala Ser Gly Thr Ile Phe Ser Ser Asn
                20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asn Thr Arg Tyr Trp Gly Gln Gly Thr
                100                 105                 110

Gln Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
 50                  55                  60

Gly Arg Phe Thr Ile Ser Arg Asp Asn Ala Lys Asn Thr Ala Tyr Leu
 65                  70                  75                  80
```

```
Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asn Thr Arg Tyr Trp Gly Gln Gly Thr
            100                 105                 110

Leu Val Thr Val Ser Ser
        115

<210> SEQ ID NO 9
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115
```

```
<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Pro Gly Lys Gln Arg Asp Leu
        35                  40                  45

Val Ala Leu Ile Asn Ser Val Gly Ile Thr Lys Tyr Ala Asp Ser Val
    50                  55                  60

Lys Gly Arg Phe Thr Ile Ser Ser Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Thr Ser Asp Gly Arg Arg Gly Trp Asp Thr Arg Tyr Trp Gly Gln Gly
            100                 105                 110

Thr Gln Val Thr Val Ser Ser
        115

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Lys Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

```
Ala Met Ala Trp Tyr Arg Gln Ala Pro Gly Lys Gln Arg Asp Leu Val
            35                  40                  45

Ala Leu Ile Asn Ser Val Gly Ile Thr Lys Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Ser Val Gln Ala Gly Glu
 1               5                  10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
            35                  40                  45

Ala Gly Ile Asn Ser Val Asp Ile Thr Lys Tyr Ala Asp Ser Val Lys
 50                  55                  60

Gly Arg Phe Thr Val Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asn Thr Arg Tyr Trp Gly Gln Gly Thr
            100                 105                 110

Gln Val Thr Val Ser Ser
        115

<210> SEQ ID NO 16
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Val Ile Asn Ser Val Gly Ile Thr Lys Tyr Ala Asp Ser Val Lys
 50                  55                  60

Gly Arg Phe Thr Ile Ser Gly Asp Asn Ala Lys Asn Thr Val Tyr Leu
 65                  70                  75                  80
```

```
Gln Met Asn Ser Leu Lys Pro Glu Asp Thr Ala Val Tyr Tyr Cys Thr
            85                  90                  95

Ser Asp Ala Arg Arg Gly Trp Asp Thr Arg Tyr Trp Gly Gln Gly Thr
        100                 105                 110

Leu Val Thr Val Ser Ser
        115

<210> SEQ ID NO 17
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asn Thr Arg Tyr Trp Gly Gln Gly Thr
        100                 105                 110

Gln Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Phe Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
        100                 105                 110

Gln Val Thr Val Ser Ser
        115
```

```
<210> SEQ ID NO 19
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Lys Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Phe Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 20
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Met Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 21
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 21

Lys Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Pro Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Phe Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Lys Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Val Gln Leu Val Glu Ser Gly Gly Gly Ser Met Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val

```
                35                  40                  45
Ala Ala Ile Asn Ser Val Gly Ile Thr Lys Tyr Ala Asp Ser Val Lys
        50                  55                  60
Gly Arg Phe Thr Ile Ser Arg Asp Asn Ala Lys Asn Thr Val Tyr Leu
65                  70                  75                  80
Gln Met Met Ser Leu Lys Pro Glu Asp Thr Ala Val Tyr Tyr Cys Thr
                85                  90                  95
Ser Asp Pro Arg Arg Gly Trp Asp Thr Arg Tyr Trp Gly Gln Gly Thr
            100                 105                 110
Gln Val Thr Val Ser Ser
            115

<210> SEQ ID NO 24
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Lys Val Gln Leu Val Glu Ser Gly Gly Gly Ser Val Gln Ala Gly Gly
1               5                   10                  15
Ser Leu Arg Leu Ser Cys Ala Ala Ser Gly Ser Ile Phe Ser Ser Asn
            20                  25                  30
Ala Met Ala Trp Tyr Arg Gln Ala Pro Gly Lys Gln Arg Asp Leu Val
            35                  40                  45
Ala Ala Ile Asn Ser Val Gly Ile Thr Lys Tyr Ala Asp Ser Val Lys
        50                  55                  60
Gly Arg Phe Thr Ile Ser Arg Asp Asn Ala Lys Asn Thr Val Tyr Leu
65                  70                  75                  80
Gln Met Met Ser Leu Lys Pro Glu Asp Thr Ala Val Tyr Tyr Cys Thr
                85                  90                  95
Ser Asp Pro Arg Arg Gly Trp Asp Thr Arg Tyr Trp Gly Gln Gly Thr
            100                 105                 110
Gln Val Thr Val Ser Ser
            115

<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Ser Val Gln Ala Gly Ala
1               5                   10                  15
Ser Leu Arg Leu Ser Cys Ala Ala Ser Gly Ser Ile Phe Ser Ser Asn
            20                  25                  30
Ala Met Ala Trp Tyr Arg Gln Ala Pro Gly Lys Gln Arg Asp Leu Val
            35                  40                  45
Ala Val Ile Asn Thr Val Gly Ile Thr Lys Tyr Ala Asp Ser Val Lys
        50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Thr
```

85                  90                  95

Ser Asp Ala Arg Arg Gly Trp Asp Thr Arg Tyr Trp Gly Gln Gly Thr
                100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Arg Gly Gly Ser Val Gln Ala Gly Glu
1               5                   10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Val Ile Asn Ser Val Gly Ile Thr Lys Tyr Ala Asp Ser Val Lys
50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
                100                 105                 110

Gln Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Arg Gly Gly Ser Val Gln Ala Gly Ala
1               5                   10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Val Ile Asn Thr Val Gly Ile Thr Lys Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
                100                 105                 110

Gln Val Thr Val Ser Ser
        115

```
<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Lys Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Leu Gly Lys Gln Arg Asp Leu Val
        35                  40                  45

Ala Leu Ile Asp Ser Ala Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Arg Leu Lys Pro Glu Asp Thr Ala Val Tyr Tyr Cys Ala
                85                  90                  95

Ser Asp Ala Arg Arg Gly Trp Asn Thr Lys Tyr Trp Gly Gln Gly Thr
            100                 105                 110

Leu Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val His Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Ala Lys Tyr Ala Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Lys Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 32
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Lys Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

```
Ala Gly Ile Asn Ser Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Leu Val Thr Val Ser Ser
            115

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Lys Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Val Ile Asn Lys Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Gln Val Thr Val Ser Ser
            115

<210> SEQ ID NO 34
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Ala Ile Asn Ser Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95
```

```
Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Arg Asn
            20                  25                  30

Ala Met Ala Trp Tyr Arg Gln Ala Pro Gly Lys Gln Arg Asp Leu Val
        35                  40                  45

Ala Ser Ile Asn Ser Val Gly Ile Thr Lys Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Leu Val Thr Val Ser Ser
        115

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Ser Val Gln Ala Gly Glu
1               5                   10                  15

Ser Leu Arg Leu Ser Cys Ala Ala Ser Gly Gly Ile Phe Ser Arg Asn
            20                  25                  30

Ala Met Ala Trp Tyr Arg Gln Ala Pro Gly Lys Gln Arg Asp Leu Val
        35                  40                  45

Ala Ser Ile Asn Ser Val Gly Ile Thr Lys Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
        115

<210> SEQ ID NO 37
```

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Arg Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asn Thr Arg Tyr Trp Gly Gln Gly Thr
            100                 105                 110

Gln Val Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Met Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115
```

<210> SEQ ID NO 40
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Leu Ile Asn Ser Val Gly Ile Thr Lys Tyr Ala Gly Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115
```

<210> SEQ ID NO 41
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45
```

Ala Ala Ile Asn Ser Val Gly Thr Thr Lys Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Leu Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Met Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

-continued

Ser Asp Pro Arg Arg Gly Trp Asp Thr Arg Tyr Trp Gly Gln Gly Thr
              100                 105                 110

Gln Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Leu Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Lys Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asn Thr Arg Tyr Trp Gly Gln Gly Thr
            100                 105                 110

Leu Val Thr Val Ser Ser
        115

<210> SEQ ID NO 46
<211> LENGTH: 118

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Val Ile Asn Ser Val Gly Ile Thr Lys Tyr Ala Asp Ser Val Lys
    50                  55                  60

Gly Arg Phe Thr Thr Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ser Ile Asp Ser Val Gly Ile Thr Lys Tyr Arg Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
        115

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Met Gln Leu Val Glu Ser Gly Gly Gly Ser Val Gln Ala Gly Glu

```
1               5                   10                  15
Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Gly Arg Arg Gly Trp Asp Thr Arg Tyr Trp Gly Gln Gly Thr
            100                 105                 110

Gln Val Thr Val Ser Ser
            115

<210> SEQ ID NO 49
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Ala Phe Val
            35                  40                  45

Ala Gly Ile Ser Gly Ser Ala Ser Arg Lys Tyr Tyr Ala Asp Ser Val
    50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
            85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser
            115                 120

<210> SEQ ID NO 50
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Gln Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Arg Glu Arg Ala Phe Val
            35                  40                  45

Ala Gly Ile Ser Gly Ser Ala Ser Arg Lys Tyr Tyr Ala Asp Ser Val
```

```
            50                  55                  60
Lys Gly Arg Phe Thr Val Ser Arg Asp Asn Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser
            115                 120

<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Gly Gly
  1                  5                  10                  15

Ser Leu Arg Leu Ser Cys Val Ala Ser Gly Arg Thr Phe Ser Ser Tyr
                 20                  25                  30

Ala Met Gly Trp Phe Arg Gln Ala Pro Gly Lys Glu Arg Glu Phe Val
             35                  40                  45

Ala Gly Ile Ser Gly Ser Gly Ser Arg Lys Tyr Tyr Ala Asp Ser Val
         50                  55                  60

Lys Gly Arg Phe Thr Ile Ser Arg Asp Asn Ala Arg Asn Thr Val Tyr
 65                  70                  75                  80

Leu Gln Met Asn Ser Leu Lys Pro Glu Asp Arg Ala Val Tyr Tyr Cys
                 85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser
            115                 120

<210> SEQ ID NO 52
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Val Gln Ala Gly Gly
  1                  5                  10                  15

Ser Leu Arg Leu Ser Cys Val Ala Ser Gly Arg Thr Phe Ser Ser Tyr
                 20                  25                  30

Ala Met Gly Trp Phe Arg Gln Ala Pro Gly Lys Glu Arg Glu Phe Val
             35                  40                  45

Ala Gly Ile Ser Gly Ser Gly Ser Arg Lys Tyr Tyr Ala Asp Ser Val
         50                  55                  60

Lys Gly Arg Phe Thr Ile Ser Arg Asp Asn Ala Arg Asn Thr Val Tyr
 65                  70                  75                  80

Leu Gln Met Asn Ser Leu Lys Pro Glu Asp Arg Ala Val Tyr Tyr Cys
                 85                  90                  95

Ala Ala Ser Asn Ser Tyr Pro Lys Val Gln Phe Asp Tyr Tyr Gly Gln
```

```
                100                 105                 110
Gly Thr Gln Val Thr Val Ser Ser
        115                 120

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Lys Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Ala
            100                 105                 110

Gln Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Thr
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Ser Gly Tyr Trp Gly Gln Gly Thr
            100                 105                 110

Gln Val Thr Val Ser Ser
        115

<210> SEQ ID NO 55
<211> LENGTH: 118
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 55

```
Glu Val Gln Leu Val Glu Ser Gly Gly Gly Leu Val Gln Pro Gly Gly
1               5                   10                  15
Ser Leu Arg Leu Ser Cys Ala Thr Ser Gly Ile Ile Phe Ser Asn Asn
            20                  25                  30
Ala Met Gly Trp Tyr Arg Gln Ala Pro Gly Lys Lys Arg Asp Leu Val
        35                  40                  45
Ala Ser Ile Ser Asn Ser Gly Ser Thr Asn Tyr Ala Asp Ser Ala Lys
    50                  55                  60
Gly Arg Phe Thr Val Ser Arg Asp Asn Asp Lys Asn Thr Gly Tyr Leu
65                  70                  75                  80
Gln Met Asn Ser Leu Lys Pro Glu Asp Thr Gly Val Tyr Tyr Cys Thr
                85                  90                  95
Val Asp Ala Arg Arg Gly Trp Asn Thr Ala Tyr Trp Gly Gln Gly Thr
            100                 105                 110
Gln Val Thr Val Ser Ser
        115
```

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Glu Val Gln Leu Val Glu Ser Gly Gly Gly Val Val Gln Pro Gly Gly
1               5                   10                  15
Ser Leu Arg Leu Ser Cys Val Thr Ser Gly Ile Ile Phe Ser Asn Asn
            20                  25                  30
Ala Met Gly Trp Tyr Arg Gln Gly Pro Gly Lys Lys Arg Asp Leu Val
        35                  40                  45
Ala Ser Ile Gly Ser Thr Tyr Ser Thr Asn Tyr Ala Asp Ser Val Lys
    50                  55                  60
Gly Arg Phe Thr Val Ser Arg Asp Asn Asp Lys Asn Thr Gly Tyr Leu
65                  70                  75                  80
Gln Met Asn Ser Leu Lys Pro Glu Asp Thr Gly Val Tyr Tyr Cys Thr
                85                  90                  95
Ile Asp Ala Arg Arg Gly Trp Asn Thr Ala Tyr Trp Gly Gln Gly Thr
            100                 105                 110
Pro Val Thr Val Ser Ser
        115
```

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Glu Val Gln Leu Val Glu Ser Gly Gly Gly Leu Val Gln Pro Gly Gly
1               5                   10                  15
```

```
Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Gly Tyr Trp Gly Gln Gly Thr
            100                 105                 110

Gln Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Val Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Ser Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60
```

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Ser Gly Tyr Trp Gly Gln Gly Thr
            100                 105                 110

Gln Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Arg Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Met Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

```
Gln Val Thr Val Ser Ser
        115

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Ser Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 64
<211> LENGTH: 118
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Gln Pro Gly Gly
1               5                   10                  15

Ser Leu Gly Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Thr Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
50                  55                  60

Gly Arg Phe Thr Val Ser Arg Asp Asn Asp Lys Asn Thr Gly Tyr Leu
65                  70                  75                  80

Gln Met Asn Asn Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Lys Val Gln Leu Val Glu Ser Gly Gly Gly Leu Val Gln Pro Gly Gly
1               5                   10                  15
```

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
            115

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
            115

<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Asp Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

```
Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Ala Tyr Trp Gly Gln Gly Thr
            100                 105                 110

Gln Val Thr Val Ser Ser
            115

<210> SEQ ID NO 69
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Arg Thr Asn
            20                  25                  30

Ala Met Gly Trp Tyr Arg Gln Ala Pro Gly Lys Lys Arg Asp Leu Val
         35                  40                  45

Ala Ser Ile Ser Asn Ser Gly Ser Thr Asn Tyr Ala Asp Ser Val Lys
     50                  55                  60

Gly Arg Phe Thr Val Ser Arg Asp Asn Asp Lys Asn Thr Ala Tyr Leu
 65                  70                  75                  80

Gln Met Asn Ser Leu Lys Pro Glu Asp Thr Gly Val Tyr Tyr Cys Thr
                 85                  90                  95

Ile Asp Gly Arg Arg Gly Trp Asn Thr Gly Tyr Trp Gly Gln Gly Thr
            100                 105                 110

Gln Val Thr Val Ser Ser
            115

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Val Glu Ser Gly Gly Gly Leu Val Gln Pro Gly Gly
 1               5                  10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
         35                  40                  45

Ala Ser Ile Ser Asn Ser Gly Ser Thr Asn Tyr Ala Asp Ser Val Lys
     50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Gly Tyr Trp Gly Gln Gly Thr
            100                 105                 110
```

-continued

Gln Val Thr Val Ser Ser
        115

<210> SEQ ID NO 71
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Leu Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 72
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Thr Ser Lys Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 73
<211> LENGTH: 118
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 73

Glu Val Gln Leu Val Glu Ser Arg Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 74
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Lys Ser Gly Gly Gly Leu Val Gln Pro Gly Gly
1               5                   10                  15

Ser Leu Arg Leu Ser Cys Thr Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Asn Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Ala Gly Gly
1               5                   10                  15

Ser Leu Arg Leu Ser Cys Val Thr Ser Gly Ile Ile Phe Ser Asn Asn

```
                    20                  25                  30

Ala Met Gly Trp Tyr Arg Gln Gly Pro Gly Lys Lys Arg Asp Leu Val
            35                  40                  45

Ala Ser Ile Gly Ser Thr Tyr Ser Thr Asn Tyr Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 76
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Ser Gly Tyr Trp Gly Gln Gly Thr
            100                 105                 110

Arg Val Thr Val Ser Ser
        115

<210> SEQ ID NO 77
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Lys Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
```

```
                65                  70                  75                  80
Gln Met Asn Ser Leu Lys Pro Glu Asp Thr Gly Val Tyr Tyr Cys Thr
                    85                  90                  95

Val Asp Ala Arg Arg Gly Trp Asn Thr Ala Tyr Trp Gly Gln Gly Thr
                100                 105                 110

Gln Val Thr Val Ser Ser
        115

<210> SEQ ID NO 78
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Gln Ala Gly Gly
1               5                   10                  15

Ser Leu Arg Leu Ser Cys Ala Thr Ser Gly Thr Ile Phe Ser Asn Asn
                20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                    85                  90                  95

Val Asp Ala Arg Arg Gly Trp Asn Thr Ala Tyr Trp Gly Gln Gly Thr
                100                 105                 110

Gln Val Thr Val Ser Ser
        115

<210> SEQ ID NO 79
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Arg
1               5                   10                  15

Ser Leu Arg Leu Ser Cys Ala Thr Ser Gly Thr Thr Phe Arg Ser Asn
                20                  25                  30

Ala Met Gly Trp Tyr Arg Gln Gly Pro Gly Lys Lys Arg Asp Leu Val
            35                  40                  45

Ala Ser Ile Thr Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Ser Ser Leu Lys Pro Glu Asp Thr Gly Val Tyr Tyr Cys Thr
                    85                  90                  95

Leu Asp Ala Arg Arg Gly Trp Asn Thr Gly Tyr Trp Gly Gln Gly Thr
                100                 105                 110

Gln Val Thr Val Ser Ser
```

<210> SEQ ID NO 80
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Gly Pro Gly Lys Lys Arg Asp Leu Val
        35                  40                  45

Ala Ser Ile Thr Asn Ser Gly Ser Thr Asn Tyr Ala Asp Ser Val Lys
    50                  55                  60

Gly Arg Phe Thr Val Ser Arg Asp Asn Asp Arg Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 81
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Lys Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Val Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 82
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 83
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Thr Ser Ala Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Ala Tyr Leu
65                  70                  75                  80

Gln Met Asn Ser Leu Lys Pro Glu Asp Thr Gly Val Tyr Tyr Cys Thr
                85                  90                  95

Ile Asp Gly Arg Arg Gly Trp Asn Thr Gly Tyr Trp Gly Gln Gly Thr
            100                 105                 110

Gln Val Thr Val Ser Ser
        115

<210> SEQ ID NO 84
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Thr Ser Ala Thr Ile Phe Arg Ser Asn
            20                  25                  30

```
Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
 50                  55                  60

Gly Arg Ser Thr Val Ser Arg Asp Asn Asp Lys Asn Thr Ala Tyr Leu
 65                  70                  75                  80

Gln Met Asn Ser Leu Lys Pro Glu Asp Thr Gly Val Tyr Tyr Cys Thr
                 85                  90                  95

Ile Asp Gly Arg Arg Gly Trp Asn Thr Gly Tyr Trp Gly Gln Gly Thr
            100                 105                 110

Gln Val Thr Val Ser Ser
        115

<210> SEQ ID NO 85
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Ser Asn Asn
                 20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
 50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Met Gly Val Tyr Tyr Cys Thr
                 85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 86
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Glu Ser Gly Gly Gly Leu Val Gln Pro Gly Gly
 1               5                  10                  15

Ser Leu Arg Leu Ser Cys Ala Thr Ser Gly Ile Ile Phe Ser Asn Asn
                 20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Ala Asn Tyr Ala Asp Ser Val Lys
 50                  55                  60

Gly Arg Phe Thr Val Ser Arg Asp Asn Asp Lys Asn Thr Gly Tyr Leu
 65                  70                  75                  80
```

```
Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 87
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Thr Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Gly Asp Asn Asp Lys Asn Thr Gly Tyr Leu
65                  70                  75                  80

Gln Met Asn Asn Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Ile Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Phe Trp Gly Gln Gly Thr
            100                 105                 110

Gln Val Thr Val Ser Ser
        115
```

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Ser Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 90
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Met Glu Ser Gly Gly Gly Met Val Gln Val Gly Gly
1               5                   10                  15

Ser Leu Arg Leu Ser Cys Thr Ala Ser Gly Leu Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Ser Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 91
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 91

Glu Val Gln Leu Val Glu Ser Gly Gly Leu Val Gln Pro Gly Gly
1               5                   10                  15

Ser Leu Arg Leu Ser Cys Ala Ile Ser Ala Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Ala Tyr Leu
65                  70                  75                  80

Gln Met Asn Ser Leu Lys Pro Glu Asp Thr Gly Val Tyr Tyr Cys Thr
                85                  90                  95

Ile Asp Gly Arg Arg Gly Trp Asn Thr Gly Tyr Trp Gly Gln Gly Thr
            100                 105                 110

Gln Val Thr Val Ser Ser
        115

<210> SEQ ID NO 92
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Met Gln Leu Val Glu Ser Gly Gly Gly Val Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Gly Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 93
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn His Ala Asp Ser Val Lys
 50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Ala Tyr Trp Gly Gln Gly Thr
            100                 105                 110

Gln Val Thr Val Ser Ser
            115

<210> SEQ ID NO 94
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Ser Asn Asn
             20                  25                  30

Ala Met Gly Trp Tyr Arg Gln Val Pro Gly Lys Lys Arg Asp Leu Val
            35                  40                  45

Ala Ser Ile Ser Asn Ser Gly Ser Thr Asn Tyr Ala Asp Ser Val Lys
 50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Gly Tyr Trp Gly Gln Gly Thr
            100                 105                 110

Gln Val Thr Val Ser Ser
            115

<210> SEQ ID NO 95
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Arg Gly Gly Leu Val Gln Pro Gly Gly
 1               5                  10                  15

Ser Leu Arg Leu Ser Cys Ala Thr Ser Gly Thr Ile Phe Ser Asn Asn
             20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
 50                  55                  60

Gly Arg Phe Thr Val Ser Arg Asp Asn Asp Lys Asn Thr Gly Tyr Leu
 65                  70                  75                  80

```
Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115
```

<210> SEQ ID NO 96
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Lys Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Ser Gly Tyr Trp Gly Gln Gly Thr
            100                 105                 110

Gln Val Thr Val Ser Ser
        115
```

<210> SEQ ID NO 97
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Glu Val Gln Leu Val Glu Ser Glu Gly Gly Leu Val Gln Pro Gly Gly
1               5                   10                  15

Ser Leu Arg Leu Pro Cys Ala Thr Ser Lys Thr Ile Phe Arg Ser Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115
```

<210> SEQ ID NO 98
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Thr Ser Lys Thr Ile Phe Arg Ser Asn
            20                  25                  30

Ala Met Gly Trp Tyr Arg Gln Ala Pro Gly Lys Lys Arg Gly Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 99
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

Glu Val Gln Leu Met Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
            20                  25                  30

Ala Met Gly Trp Tyr Arg Gln Gly Pro Gly Lys Lys Arg Asp Leu Val
        35                  40                  45

Ala Ser Ile Thr Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Ser Ser Leu Lys Pro Glu Asp Thr Gly Val Tyr Tyr Cys Thr
                85                  90                  95

Leu Asp Ala Arg Arg Gly Trp Asn Thr Gly Tyr Trp Gly Gln Gly Thr
            100                 105                 110

Gln Val Thr Val Ser Ser
        115

<210> SEQ ID NO 100
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Thr Asn Thr Gly Ser Thr Asn Tyr Ala Asp Ser Val Lys
    50                  55                  60

Gly Arg Phe Thr Val Ser Arg Asp Asn Asp Arg Asn Thr Val Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 101
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Glu Ser Gly Gly Gly Leu Val Gln Ala Gly Gly
1               5                   10                  15

Ser Leu Arg Leu Ser Cys Thr Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Asn Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 102
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val

```
            35                  40                  45
Ala Ser Ile Ser Asn Ser Gly Ser Thr Asn Tyr Ala Asp Ser Ala Lys
         50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Gly Tyr Trp Gly Gln Gly Thr
            100                 105                 110

Gln Val Thr Val Ser Ser
            115

<210> SEQ ID NO 103
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Leu Val Gln Pro Gly Gly Ser
 1               5                  10                  15

Leu Arg Leu Ser Cys Ala Thr Ser Gly Thr Ile Phe Ser Asn Asn Ala
             20                  25                  30

Met Gly Trp Tyr Arg Gln Ala Pro Gly Lys Lys Arg Asp Leu Val Ala
         35                  40                  45

Ser Ile Ser Asn Ser Gly Ser Thr Asn Tyr Ala Asp Ser Val Lys Gly
     50                  55                  60

Arg Phe Thr Val Ser Arg Asp Asn Asp Lys Asn Thr Gly Tyr Leu Gln
 65                  70                  75                  80

Met Asn Ser Leu Lys Pro Glu Asp Thr Gly Val Tyr Tyr Cys Thr Val
                 85                  90                  95

Asp Ala Arg Arg Gly Trp Asn Thr Ala Tyr Trp Gly Gln Gly Thr Gln
            100                 105                 110

Val Thr Val Ser Ser
            115

<210> SEQ ID NO 104
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Gln Ala Gly Gly
 1               5                  10                  15

Ser Leu Arg Leu Ser Cys Val Ala Ser Gly Ser Ile Phe Arg Ser Asn
             20                  25                  30

Ala Met Gly Trp Tyr Arg Gln Ala Pro Gly Lys Lys Arg Asp Leu Val
         35                  40                  45

Ala Ser Ile Ser Asn Ser Gly Ser Thr Asn Tyr Ala Asp Ser Val Lys
     50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
```

85                  90                  95

Ile Asp Ala Arg Arg Gly Trp Asn Thr Gly Tyr Trp Gly Gln Gly Thr
                100                 105                 110

Gln Val Thr Val Ser Ser
        115

<210> SEQ ID NO 105
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
                100                 105                 110

Gln Val Thr Val Ser Ser
        115

<210> SEQ ID NO 106
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Val Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
                100                 105                 110

Gln Val Thr Val Ser Ser
        115

```
<210> SEQ ID NO 107
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107
```

| Glu | Val | Gln | Leu | Val | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Thr | Ser | Lys | Pro | Ile | Phe | Arg | Ser | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Met | Gly | Trp | Tyr | Arg | Gln | Ala | Pro | Gly | Lys | Lys | Arg | Asp | Leu | Val |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ala | Ser | Ile | Ser | Asn | Ser | Gly | Ser | Thr | Asn | Tyr | Ala | Asp | Ser | Val | Lys |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Gly | Arg | Phe | Thr | Val | Ser | Arg | Asp | Asn | Asp | Lys | Asn | Thr | Gly | Tyr | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Met | Asn | Ser | Leu | Lys | Pro | Glu | Asp | Thr | Gly | Val | Tyr | Tyr | Cys | Thr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Val | Asp | Ala | Arg | Arg | Gly | Trp | Asn | Thr | Gly | Tyr | Trp | Gly | Gln | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gln | Val | Thr | Val | Ser | Ser |
|-----|-----|-----|-----|-----|-----|
|     |     |     | 115 |     |     |

```
<210> SEQ ID NO 108
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108
```

| Glu | Val | Gln | Leu | Val | Glu | Ser | Glu | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Thr | Thr | Ser | Gly | Thr | Ile | Phe | Ser | Asn | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Met | Gly | Trp | Tyr | Arg | Gln | Ala | Pro | Gly | Lys | Lys | Arg | Asp | Leu | Val |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ala | Ser | Ile | Ser | Asn | Ser | Gly | Ser | Thr | Asn | Tyr | Ala | Asp | Ser | Val | Lys |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Gly | Arg | Phe | Thr | Val | Ser | Arg | Asp | Asn | Asp | Lys | Asn | Thr | Gly | Tyr | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Met | Asn | Asn | Leu | Lys | Pro | Glu | Asp | Thr | Gly | Val | Tyr | Tyr | Cys | Thr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Asp | Ala | Arg | Arg | Gly | Trp | Asn | Thr | Ala | Tyr | Trp | Gly | Gln | Gly | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gln | Val | Thr | Val | Ser | Ser |
|-----|-----|-----|-----|-----|-----|
|     |     |     | 115 |     |     |

```
<210> SEQ ID NO 109
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109
```

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Pro Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 110
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Glu Ser Glu Gly Gly Val Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Gly Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Met Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

```
Ala Ser Ile Ser Asn Ser Gly Ser Thr Asn Tyr Ala Asp Ser Val Lys
            50                  55                  60

Gly Arg Phe Thr Val Ser Arg Asp Asn Asp Lys Ser Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 112
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Gly Val Val Gln Pro Gly Glu
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
            35                  40                  45

Ala Ser Ile Gly Ser Thr Tyr Ser Thr Asn Tyr Ala Asp Ser Val Lys
            50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 113
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Lys Val Gln Leu Val Glu Ser Gly Gly Gly Leu Val Gln Pro Gly Asp
1               5                   10                  15

Ser Leu Arg Leu Ser Cys Ala Ala Ser Gly Leu Thr Leu Asp Asp Tyr
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
            50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95
```

Ile Asp Ala Arg Arg Gly Trp Asn Thr Gly Tyr Trp Gly Gln Gly Thr
            100                 105                 110

Gln Val Thr Val Ser Ser
        115

<210> SEQ ID NO 114
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Lys Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Gly Tyr Trp Gly Gln Gly Thr
            100                 105                 110

Gln Val Thr Val Ser Ser
        115

<210> SEQ ID NO 115
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Val Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Arg Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 116

<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

```
Glu Val Gln Leu Val Glu Ser Gly Gly Gly Leu Val Gln Ala Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Ser Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115
```

<210> SEQ ID NO 117
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Glu Val Gln Leu Val Glu Ser Gly Gly Gly Leu Val Gln Pro Gly Gly
1               5                   10                  15

Ser Leu Arg Leu Ser Cys Ala Thr Ser Lys Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Thr Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115
```

<210> SEQ ID NO 118
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

```
Lys Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
            115
```

<210> SEQ ID NO 119
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Ala Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
            115
```

<210> SEQ ID NO 120
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45
```

Ala Ser Ile Ser Asn Ser Gly Ser Thr Asn Tyr Ala Asp Phe Val Lys
            50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 121
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Ser Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 122
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Val Gln Leu Val Glu Ser Gly Gly Gly Ser Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

```
Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 123
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Glu Ser Gly Gly Gly Leu Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 124
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Glu Ser Gly Gly Gly Ser Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 125
<211> LENGTH: 118
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Gly Ser Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 126
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Ser Gly Gly Gly Ser Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Glu Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 127
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Val Glu Ser Gly Gly Gly Leu Val Gln Pro Gly Gly

```
                1               5                   10                  15
Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
            35                  40                  45

Ala Ala Ile Asn Ser Val Gly Val Thr Lys Tyr Ala Asp Ser Val Lys
            50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 128
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Ala Ile Asn Ser Val Gly Val Thr Lys Tyr Ala Asp Ser Val Lys
            50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 129
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Glu Leu Val
            35                  40                  45

Ala Ala Ile Asn Ser Val Gly Val Thr Lys Tyr Ala Asp Ser Val Lys
```

```
                    50                  55                  60
Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                     85                  90                  95

Ser Asp Pro Arg Arg Gly Trp Asp Thr Arg Tyr Trp Gly Gln Gly Thr
                100                 105                 110

Leu Val Thr Val Ser Ser
            115

<210> SEQ ID NO 130
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ser Asn
             20                  25                  30

Ala Met Ala Trp Tyr Arg Gln Ala Pro Gly Lys Gln Arg Glu Leu Val
         35                  40                  45

Ala Ala Ile Asn Ser Val Gly Val Thr Lys Tyr Ala Asp Ser Val Lys
     50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                     85                  90                  95

Ser Asp Pro Arg Arg Gly Trp Asp Thr Arg Tyr Trp Gly Gln Gly Thr
                100                 105                 110

Leu Val Thr Val Ser Ser
            115

<210> SEQ ID NO 131
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
             20                  25                  30

Ala Met Ala Trp Tyr Arg Gln Ala Pro Gly Lys Arg Arg Asp Leu Val
         35                  40                  45

Ala Ala Ile Ser Ser Val Gly Val Thr Lys Tyr Ala Asp Ser Val Lys
     50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                     85                  90                  95

Ser Asp Pro Arg Arg Gly Trp Asp Thr Arg Tyr Trp Gly Gln Gly Thr
```

-continued

```
                100                 105                 110

Leu Val Thr Val Ser Ser
        115

<210> SEQ ID NO 132
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Gln Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 133
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Gly Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 134
<211> LENGTH: 118
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Thr Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 135
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Thr Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 136
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Gly Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 137
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Pro Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 138
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
        100                 105                 110

Leu Val Thr Val Ser Ser
        115

<210> SEQ ID NO 139
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Thr Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
        100                 105                 110

Leu Val Thr Val Ser Ser
        115

<210> SEQ ID NO 140
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
        100                 105                 110

Leu Val Thr Val Ser Ser
        115

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Ser Ile Phe Ser Ser Asn Ala Met Ala
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Thr Ile Phe Ser Ser Asn Ala Met Ala
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Ser Ile Phe Ser Ser Asn Ala Lys Ala
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Ser Ile Phe Ser Arg Asn Ala Met Ala
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Ile Phe Ser Arg Asn Ala Met Ala
1               5                   10

<210> SEQ ID NO 146
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 146

Gly Arg Thr Phe Ser Ser Tyr Ala Met Gly
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Thr Ile Phe Ser Asn Asn Ala Met Gly
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Thr Ile Phe Ser Asn Thr Ala Met Gly
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Ile Ile Phe Ser Asn Asn Ala Met Gly
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Arg Thr Ile Phe Arg Ser Asn Ala Met Gly
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Thr Ile Phe Arg Ser Asn Ala Met Gly
1               5                   10
```

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Thr Ile Phe Arg Thr Asn Ala Met Gly
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Lys Thr Ile Phe Arg Ser Asn Ala Met Gly
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Thr Thr Phe Arg Ser Asn Ala Met Gly
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Thr Ile Phe Arg Ser Asn Ala Met Gly
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Leu Ile Phe Ser Asn Asn Ala Met Gly
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 157

Gly Ser Ile Phe Arg Ser Asn Ala Met Gly
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Thr Ile Phe Ser Asn Asn Ala Met Gly
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Thr Val Phe Ser Asn Asn Ala Met Gly
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Lys Pro Ile Phe Arg Ser Asn Ala Met Gly
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Leu Thr Leu Asp Asp Tyr Ala Met Gly
1               5                   10

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Ile Asn Ser Val Gly Val Thr Lys
1               5

<210> SEQ ID NO 163
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 163

Val Ile Asn Ser Val Gly Ile Thr Lys
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Ile Asn Ser Val Gly Ile Thr Lys
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Ile Asn Ser Val Asp Ile Thr Lys
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ile Asn Ser Val Gly Ile Thr Lys
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Ile Asn Ser Val Gly Ile Thr Lys
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Val Ile Asn Thr Val Gly Ile Thr Lys
1               5
```

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Leu Ile Asp Ser Ala Gly Ile Thr Lys
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Ile Asn Ser Val Gly Ile Ala Lys
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Ile Asn Lys Val Gly Ile Thr Lys
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Ile Asn Ser Val Gly Ile Thr Lys
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Ile Asn Ser Val Asp Ile Thr Arg
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 174

Ala Ile Asn Ser Val Gly Thr Thr Lys
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ile Asp Ser Val Gly Ile Thr Lys
1               5

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ile Ser Gly Ser Ala Ser Arg Lys Tyr
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Ile Ser Gly Ser Gly Ser Arg Lys Tyr
1               5                   10

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Ile Ser Ser Ser Gly Ser Thr Asn
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Ile Ser Asn Ser Gly Ser Thr Asn
1               5

<210> SEQ ID NO 180
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Ile Gly Ser Thr Tyr Ser Thr Asn
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Ile Ser Ser Thr Tyr Ser Thr Asn
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Ile Thr Asn Ser Gly Ser Thr Asn
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ile Ser Asn Ser Gly Ser Ala Asn
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Ile Ser Ile Ser Gly Ser Thr Asn
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Ile Thr Asn Thr Gly Ser Thr Asn
```

```
1               5

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Pro Arg Arg Gly Trp Asp Thr Arg Tyr
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Ala Arg Arg Gly Trp Asp Thr Arg Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asp Pro Arg Arg Gly Trp Asn Thr Arg Tyr
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Gly Arg Arg Gly Trp Asp Thr Arg Tyr
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Ala Arg Arg Gly Trp Asn Thr Lys Tyr
1               5                   10

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 191

Ser Asn Ser Tyr Pro Lys Val Gln Phe Asp Tyr
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Ala Arg Arg Gly Trp Asn Thr Ala Tyr
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asp Ala Arg Arg Gly Trp Asn Ser Gly Tyr
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Ala Arg Arg Gly Trp Asn Thr Gly Tyr
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asp Gly Arg Arg Gly Trp Asn Thr Gly Tyr
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asp Ala Arg Arg Gly Trp Asn Thr Gly Phe
1               5                   10

<210> SEQ ID NO 197

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 198
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Thr Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 199
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65              70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 200
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Thr Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65              70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Ala
        115

<210> SEQ ID NO 201
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

```
Ala Ala Ile Ser Thr Val Gly Val Thr Lys Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser Lys
            115
```

```
<210> SEQ ID NO 202
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ser Thr
                 20                  25                  30

Ala Met Ala Trp Tyr Arg Gln Ala Pro Gly Lys Arg Arg Asp Leu Val
             35                  40                  45

Ala Ala Ile Ser Thr Val Gly Val Thr Lys Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser Ala Lys
            115                 120
```

```
<210> SEQ ID NO 203
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Glu Val Gln Leu Val Glu Ser Gly Gly Gly Leu Val Gln Ala Gly Gly
 1               5                  10                  15

Ser Leu Arg Leu Ser Cys Val Ala Ser Gly Arg Thr Phe Ser Ser Tyr
                 20                  25                  30

Ala Met Gly Trp Phe Arg Gln Ala Pro Gly Lys Glu Arg Ala Phe Val
             35                  40                  45

Ala Gly Ile Ser Gly Ser Ala Ser Arg Lys Tyr Tyr Ala Asp Ser Val
 50                  55                  60

Lys Gly Arg Phe Thr Val Ser Arg Asp Asn Ala Arg Asn Thr Val Tyr
 65                  70                  75                  80

Leu Gln Met Asn Ser Leu Lys Pro Glu Asp Thr Ala Val Tyr Tyr Cys
                 85                  90                  95
```

```
Ala Ala Ser Asn Ser Tyr Pro Lys Val Gln Phe Asp Tyr Tyr Gly Gln
                100                 105                 110

Gly Thr Gln Val Thr Val Ser Ser Gly Gly Gly Gly Ser Gly Gly Gly
            115                 120                 125

Gly Ser Gly Gly Gly Ser Gly Gly Gly Ser Gly Gly Gly Gly
        130                 135                 140

Ser Gly Gly Gly Gly Ser Gly Gly Gly Ser Lys Val Gln Leu Val
145                 150                 155                 160

Glu Ser Gly Gly Gly Leu Val Gln Pro Gly Ser Leu Arg Leu Ser
                165                 170                 175

Cys Ala Thr Ser Gly Thr Ile Phe Ser Asn Asn Ala Met Gly Trp Tyr
                180                 185                 190

Arg Gln Ala Pro Gly Lys Lys Arg Asp Leu Val Ala Ser Ile Ser Ser
                195                 200                 205

Ser Gly Ser Thr Asn Tyr Ala Asp Ser Val Lys Gly Arg Phe Thr Val
            210                 215                 220

Ser Arg Asp Asn Asp Lys Asn Thr Gly Tyr Leu Gln Met Asn Ser Leu
225                 230                 235                 240

Lys Pro Glu Asp Thr Gly Val Tyr Tyr Cys Thr Leu Asp Ala Arg Arg
                245                 250                 255

Gly Trp Asn Thr Ala Tyr Trp Gly Gln Gly Ala Gln Val Thr Val Ser
                260                 265                 270

Ser

<210> SEQ ID NO 204
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Lys Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Ala
                100                 105                 110

Gln Val Thr Val Ser Ser Gly Gly Gly Gly Ser Gly Gly Gly Gly Ser
            115                 120                 125

Gly Gly Gly Gly Ser Gly Gly Gly Gly Ser Gly Gly Gly Ser Gly
        130                 135                 140

Gly Gly Gly Ser Gly Gly Gly Ser Glu Val Gln Leu Val Glu Ser
145                 150                 155                 160

Gly Gly Gly Leu Val Gln Ala Gly Gly Ser Leu Arg Leu Ser Cys Val
                165                 170                 175
```

```
Ala Ser Gly Arg Thr Phe Ser Ser Tyr Ala Met Gly Trp Phe Arg Gln
            180                 185                 190

Ala Pro Gly Lys Glu Arg Ala Phe Val Ala Gly Ile Ser Gly Ser Ala
            195                 200                 205

Ser Arg Lys Tyr Tyr Ala Asp Ser Val Lys Gly Arg Phe Thr Val Ser
            210                 215                 220

Arg Asp Asn Ala Arg Asn Thr Val Tyr Leu Gln Met Asn Ser Leu Lys
225                 230                 235                 240

Pro Glu Asp Thr Ala Val Tyr Tyr Cys Ala Ala Ser Asn Ser Tyr Pro
            245                 250                 255

Lys Val Gln Phe Asp Tyr Tyr Gly Gln Gly Thr Gln Val Thr Val Ser
            260                 265                 270

Ser
```

<210> SEQ ID NO 205
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Gly Ile Asn Ser Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Ser Gly Gly Gly Ser Gly Gly Gly Gly Ser Gly
        130                 135                 140

Gly Gly Gly Ser Gly Gly Gly Gly Ser Lys Val Gln Leu Val Glu Ser
145                 150                 155                 160

Gly Gly Gly Leu Val Gln Pro Gly Gly Ser Leu Arg Leu Ser Cys Ala
            165                 170                 175

Thr Ser Gly Thr Ile Phe Ser Asn Asn Ala Met Gly Trp Tyr Arg Gln
            180                 185                 190

Ala Pro Gly Lys Lys Arg Asp Leu Val Ala Ser Ile Ser Ser Ser Gly
            195                 200                 205

Ser Thr Asn Tyr Ala Asp Ser Val Lys Gly Arg Phe Thr Val Ser Arg
            210                 215                 220

Asp Asn Asp Lys Asn Thr Gly Tyr Leu Gln Met Asn Ser Leu Lys Pro
225                 230                 235                 240

Glu Asp Thr Gly Val Tyr Tyr Cys Thr Leu Asp Ala Arg Arg Gly Trp
            245                 250                 255
```

```
Asn Thr Ala Tyr Trp Gly Gln Gly Ala Gln Val Thr Val Ser Ser
            260                 265                 270
```

<210> SEQ ID NO 206
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Val Ile Asn Ser Val Gly Ile Thr Lys Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser Gly Gly Gly Ser Gly Gly Gly Gly Ser
        115                 120                 125

Gly Gly Gly Gly Ser Gly Gly Gly Ser Gly Gly Gly Ser Gly
    130                 135                 140

Gly Gly Gly Ser Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
                165                 170                 175

Ala Ser Gly Ser Ile Phe Ser Ser Asn Ala Met Ala Trp Tyr Arg Gln
            180                 185                 190

Ala Pro Gly Lys Gln Arg Asp Leu Val Ala Val Ile Asn Ser Val Gly
        195                 200                 205

Ile Thr Lys Tyr Ala Asp Ser Val Lys Gly Arg Phe Thr Ile Ser Gly
    210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Ala Arg Arg Gly Trp
                245                 250                 255

Asp Thr Arg Tyr Trp Gly Gln Gly Thr Gln Val Thr Val Ser Ser
            260                 265                 270
```

<210> SEQ ID NO 207
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

```
Glu Val Gln Leu Val Glu Ser Gly Gly Gly Ser Val Gln Ala Gly Glu
1               5                   10                  15
```

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu
        35                  40                  45

Val Ala Leu Ile Asn Ser Val Gly Ile Thr Lys Tyr Ala Asp Ser Val
    50                  55                  60

Lys Gly Arg Phe Thr Ile Ser Ser Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Thr Ser Asp Gly Arg Arg Gly Trp Asp Thr Arg Tyr Trp Gly Gln Gly
            100                 105                 110

Thr Gln Val Thr Val Ser Ser Gly Gly Gly Ser Gly Gly Gly Gly
        115                 120                 125

Ser Gly Gly Gly Gly Ser Gly Gly Gly Ser Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Ser Val Gln Ala Gly Glu Ser Leu Arg Leu Ser Cys
            165                 170                 175

Ala Ala Ser Gly Ser Ile Phe Ser Ser Asn Ala Met Ala Trp Tyr Arg
        180                 185                 190

Gln Ala Pro Pro Gly Lys Gln Arg Asp Leu Val Ala Leu Ile Asn Ser
            195                 200                 205

Val Gly Ile Thr Lys Tyr Ala Asp Ser Val Lys Gly Arg Phe Thr Ile
        210                 215                 220

Ser Ser Asp Asn Ala Lys Asn Thr Val Tyr Leu Glu Met Asn Ser Leu
225                 230                 235                 240

Lys Pro Glu Asp Thr Ala Val Tyr Tyr Cys Thr Ser Asp Gly Arg Arg
                245                 250                 255

Gly Trp Asp Thr Arg Tyr Trp Gly Gln Gly Thr Gln Val Thr Val Ser
            260                 265                 270

Ser

<210> SEQ ID NO 208
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
                100                 105                 110

Gln Val Thr Val Ser Ser Gly Gly Gly Ser Gly Gly Gly Gly Ser
        115                 120                 125

Gly Gly Gly Gly Ser Gly Gly Gly Ser Gly Gly Gly Ser Gly
130                 135                 140

Gly Gly Gly Ser Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
                165                 170                 175

Ala Ser Gly Ser Ile Phe Ser Ser Asn Ala Met Ala Trp Tyr Arg Gln
                180                 185                 190

Ala Pro Gly Lys Arg Arg Asp Leu Val Ala Ala Ile Asn Ser Val Gly
                195                 200                 205

Val Thr Lys Tyr Ala Asp Ser Val Lys Gly Arg Phe Thr Ile Ser Arg
        210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Pro Arg Arg Gly Trp
                245                 250                 255

Asp Thr Arg Tyr Trp Gly Gln Gly Thr Gln Val Thr Val Ser Ser
                260                 265                 270

<210> SEQ ID NO 209
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Met Gln Leu Val Glu Ser Gly Gly Ser Val Gln Ala Gly Glu
1               5                   10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
                35                  40                  45

Ala Leu Ile Asn Ser Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Gly Arg Arg Gly Trp Asp Thr Arg Tyr Trp Gly Gln Gly Thr
                100                 105                 110

Gln Val Thr Val Ser Ser Gly Gly Gly Gly Ser Gly Gly Gly Gly Ser
        115                 120                 125

Gly Gly Gly Gly Ser Gly Gly Gly Ser Gly Gly Gly Gly Ser Gly
130                 135                 140

Gly Gly Gly Ser Gly Gly Gly Ser Glu Met Gln Leu Val Glu Ser
145                 150                 155                 160

Gly Gly Gly Ser Val Gln Ala Gly Glu Ser Leu Arg Leu Ser Cys Ala
                165                 170                 175

Ala Ser Gly Ser Ile Phe Ser Ser Asn Ala Met Ala Trp Tyr Arg Gln
                180                 185                 190

Ala Pro Gly Lys Gln Arg Asp Leu Val Ala Leu Ile Asn Ser Val Gly
            195                 200                 205

Ile Thr Lys Tyr Ala Asp Ser Val Lys Gly Arg Phe Thr Ile Ser Arg
    210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Gly Arg Arg Gly Trp
                245                 250                 255

Asp Thr Arg Tyr Trp Gly Gln Gly Thr Gln Val Thr Val Ser Ser
            260                 265                 270

<210> SEQ ID NO 210
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
                165                 170                 175

Ala Ser Gly Ser Ile Phe Ser Ser Asn Ala Met Ala Trp Tyr Arg Gln
            180                 185                 190

Ala Pro Gly Lys Gln Arg Asp Leu Val Ala Gly Ile Asn Ser Val Gly
        195                 200                 205

Ile Thr Lys Tyr Ala Asp Ser Val Lys Gly Arg Phe Thr Ile Ser Arg
    210                 215                 220

Asp Asn Ala Lys Asn Thr Ala Tyr Leu Gln Met Asn Ser Leu Lys Pro
225                 230                 235                 240

Glu Asp Thr Ala Val Tyr Tyr Cys Thr Ser Asp Pro Arg Arg Gly Trp
                245                 250                 255

Asp Thr Arg Tyr Trp Gly Gln Gly Thr Leu Val Thr Val Ser Ser
            260                 265                 270

<210> SEQ ID NO 211
<211> LENGTH: 273
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 211

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Ala Phe Val
        35                  40                  45

Ala Gly Ile Ser Gly Ser Ala Ser Arg Lys Tyr Tyr Ala Asp Ser Val
    50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Ser Val Gln Ala Gly Glu Ser Leu Arg Leu Ser
                165                 170                 175

Cys Ala Ala Ser Gly Ser Ile Phe Ser Ser Asn Ala Met Ala Trp Tyr
            180                 185                 190

Arg Gln Ala Pro Gly Lys Arg Arg Asp Leu Val Ala Ala Ile Asn Ser
        195                 200                 205

Val Gly Val Thr Lys Tyr Ala Asp Ser Val Lys Gly Arg Phe Thr Ile
    210                 215                 220

Ser Arg Asp Asn Ala Lys Asn Thr Val Tyr Leu Gln Met Asn Ser Leu
225                 230                 235                 240

Lys Pro Glu Asp Thr Ala Val Tyr Tyr Cys Thr Ser Asp Pro Arg Arg
                245                 250                 255

Gly Trp Asp Thr Arg Tyr Trp Gly Gln Gly Thr Gln Val Thr Val Ser
            260                 265                 270

Ser

<210> SEQ ID NO 212
<211> LENGTH: 273
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 212

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

-continued

Ala Met Gly Trp Phe Arg Gln Ala Pro Gly Lys Glu Arg Ala Phe Val
            35                  40                  45

Ala Gly Ile Ser Gly Ser Ala Ser Arg Lys Tyr Tyr Ala Asp Ser Val
 50                  55                  60

Lys Gly Arg Phe Thr Val Ser Arg Asp Asn Ala Arg Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
               100                 105                 110

Gly Thr Gln Val Thr Val Ser Ser Gly Gly Gly Gly Ser Gly Gly Gly
             115                 120                 125

Gly Ser Gly Gly Gly Gly Ser Gly Gly Gly Ser Gly Gly Gly Gly
             130                 135                 140

Ser Gly Gly Gly Gly Ser Gly Gly Gly Ser Glu Val Gln Leu Val
145                 150                 155                 160

Glu Ser Gly Gly Gly Ser Val Gln Ala Gly Glu Ser Leu Arg Leu Ser
                165                 170                 175

Cys Ala Ala Ser Gly Ser Ile Phe Ser Ser Asn Ala Met Ala Trp Tyr
            180                 185                 190

Arg Gln Ala Pro Gly Lys Gln Arg Asp Leu Val Ala Gly Ile Asn Ser
        195                 200                 205

Val Gly Ile Thr Lys Tyr Ala Asp Ser Val Lys Gly Arg Phe Thr Ile
    210                 215                 220

Ser Arg Asp Asn Ala Lys Asn Thr Ala Tyr Leu Gln Met Asn Ser Leu
225                 230                 235                 240

Lys Pro Glu Asp Thr Ala Val Tyr Tyr Cys Thr Ser Asp Pro Arg Arg
                245                 250                 255

Gly Trp Asp Thr Arg Tyr Trp Gly Gln Gly Thr Leu Val Thr Val Ser
            260                 265                 270

Ser

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Ser Ile Phe Ser Ser Thr Ala Met Ala
1               5                   10

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Ile Ser Ser Val Gly Val Thr Lys
1               5

<210> SEQ ID NO 215
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ala Ile Gln Ser Val Gly Val Thr Lys
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Ile Gly Ser Val Gly Val Thr Lys
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Ile Thr Ser Val Gly Val Thr Lys
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Ile Asn Thr Val Gly Val Thr Lys
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ala Ile Asn Gly Val Gly Val Thr Lys
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ala Ile Asn Pro Val Gly Val Thr Lys
```

```
                                              1               5
```

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Ala Ile Ser Thr Val Gly Val Thr Lys
1               5
```

<210> SEQ ID NO 222
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

```
Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Ala Phe Val
        35                  40                  45

Ala Gly Ile Ser Gly Ser Ala Ser Arg Lys Tyr Tyr Ala Asp Ser Val
    50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Val Ala Ser Gly Arg Thr Phe Ser Ser Tyr Ala Met Gly Trp Phe
            180                 185                 190

Arg Gln Ala Pro Gly Lys Glu Arg Ala Phe Val Ala Gly Ile Ser Gly
        195                 200                 205

Ser Ala Ser Arg Lys Tyr Tyr Ala Asp Ser Val Lys Gly Arg Phe Thr
    210                 215                 220

Val Ser Arg Asp Asn Ala Arg Asn Thr Val Tyr Leu Gln Met Asn Ser
225                 230                 235                 240

Leu Lys Pro Glu Asp Thr Ala Val Tyr Tyr Cys Ala Ala Ser Asn Ser
                245                 250                 255

Tyr Pro Lys Val Gln Phe Asp Tyr Tyr Gly Gln Gly Thr Leu Val Thr
            260                 265                 270

Val Ser Ser
```

<210> SEQ ID NO 223
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Thr Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Ser Ile Phe Ser Ser Thr Ala Met Ala Trp Tyr Arg Gln
            180                 185                 190

Ala Pro Gly Lys Arg Arg Asp Leu Val Ala Ala Ile Ser Thr Val Gly
        195                 200                 205

Val Thr Lys Tyr Ala Asp Ser Val Lys Gly Arg Phe Thr Ile Ser Arg
    210                 215                 220

Asp Asn Ser Lys Asn Thr Val Tyr Leu Gln Met Asn Ser Leu Arg Pro
225                 230                 235                 240

Glu Asp Thr Ala Val Tyr Tyr Cys Thr Ser Asp Pro Arg Arg Gly Trp
                245                 250                 255

Asp Thr Arg Tyr Trp Gly Gln Gly Thr Leu Val Thr Val Ser Ser
            260                 265                 270

<210> SEQ ID NO 224
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

Lys Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn

```
            20                  25                  30

Ala Met Gly Trp Tyr Arg Gln Ala Pro Gly Lys Lys Arg Asp Leu Val
        35                  40                  45

Ala Ser Ile Ser Ser Gly Ser Thr Asn Tyr Ala Asp Ser Val Lys
50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Ala
                100                 105                 110

Gln Val Thr Val Ser Ser Ala Ala Glu Gln Lys Leu Ile Ser Glu
        115                 120                 125

Glu Asp Leu Asn Gly Ala Ala His His His His His His
    130                 135                 140

<210> SEQ ID NO 225
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
                100                 105                 110

Gln Val Thr Val Ser Ser Ala Ala Ala Glu Gln Lys Leu Ile Ser Glu
        115                 120                 125

Glu Asp Leu Asn Gly Ala Ala His His His His His
    130                 135                 140

<210> SEQ ID NO 226
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Ala Phe Val
```

```
                35                  40                  45
Ala Gly Ile Ser Gly Ser Ala Ser Arg Lys Tyr Tyr Ala Asp Ser Val
         50                  55                  60
Lys Gly Arg Phe Thr Val Ser Arg Asp Asn Ala Arg Asn Thr Val Tyr
 65                  70                  75                  80
Leu Gln Met Asn Ser Leu Lys Pro Glu Asp Thr Ala Val Tyr Tyr Cys
                 85                  90                  95
Ala Ala Ser Asn Ser Tyr Pro Lys Val Gln Phe Asp Tyr Tyr Gly Gln
                100                 105                 110
Gly Thr Gln Val Thr Val Ser Ser Ala Ala Ala Glu Gln Lys Leu Ile
            115                 120                 125
Ser Glu Glu Asp Leu Asn Gly Ala Ala His His His His His His
130                 135                 140
```

<210> SEQ ID NO 227
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

```
Glu Val Gln Leu Val Glu Ser Gly Gly Gly Ser Val Gln Ala Gly Glu
 1               5                  10                  15
Ser Leu Arg Leu Ser Cys Ala Ala Ser Gly Ser Ile Phe Ser Ser Asn
                20                  25                  30
Ala Met Ala Trp Tyr Arg Gln Ala Pro Gly Lys Gln Arg Asp Leu
                35                  40                  45
Val Ala Leu Ile Asn Ser Val Gly Ile Thr Lys Tyr Ala Asp Ser Val
         50                  55                  60
Lys Gly Arg Phe Thr Ile Ser Ser Asp Asn Ala Lys Asn Thr Val Tyr
 65                  70                  75                  80
Leu Glu Met Asn Ser Leu Lys Pro Glu Asp Thr Ala Val Tyr Tyr Cys
                 85                  90                  95
Thr Ser Asp Gly Arg Arg Gly Trp Asp Thr Arg Tyr Trp Gly Gln Gly
                100                 105                 110
Thr Gln Val Thr Val Ser Ser Ala Ala Ala Glu Gln Lys Leu Ile Ser
            115                 120                 125
Glu Glu Asp Leu Asn Gly Ala Ala His His His His His His
130                 135                 140
```

<210> SEQ ID NO 228
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

```
Glu Val Gln Leu Val Glu Ser Gly Gly Gly Leu Val Gln Ala Gly Gly
 1               5                  10                  15
Ser Leu Arg Leu Ser Cys Val Ala Ser Gly Arg Thr Phe Ser Ser Tyr
                20                  25                  30
Ala Met Gly Trp Phe Arg Gln Ala Pro Gly Lys Glu Arg Ala Phe Val
                35                  40                  45
Ala Gly Ile Ser Gly Ser Ala Ser Arg Lys Tyr Tyr Ala Asp Ser Val
```

```
                  50                  55                  60
Lys Gly Arg Phe Thr Val Ser Arg Asp Asn Ala Arg Asn Thr Val Tyr
 65                  70                  75                  80

Leu Gln Met Asn Ser Leu Lys Pro Glu Asp Thr Ala Val Tyr Tyr Cys
                     85                  90                  95

Ala Ala Ser Asn Ser Tyr Pro Lys Val Gln Phe Asp Tyr Tyr Gly Gln
                    100                 105                 110

Gly Thr Leu Val Thr Val Ser Ser Gly Gly Gly Ser Gly Gly Gly Gly
                115                 120                 125

Gly Ser Gly Gly Gly Gly Ser Gly Gly Gly Ser Gly Gly Gly Gly
            130                 135                 140

Ser Gly Gly Gly Gly Ser Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Val Ala Ser Gly Arg Thr Phe Ser Ser Tyr Ala Met Gly Trp Phe
                180                 185                 190

Arg Gln Ala Pro Gly Lys Glu Arg Ala Phe Val Ala Gly Ile Ser Gly
                195                 200                 205

Ser Ala Ser Arg Lys Tyr Tyr Ala Asp Ser Val Lys Gly Arg Phe Thr
210                 215                 220

Val Ser Arg Asp Asn Ala Arg Asn Thr Val Tyr Leu Gln Met Asn Ser
225                 230                 235                 240

Leu Lys Pro Glu Asp Thr Ala Val Tyr Tyr Cys Ala Ala Ser Asn Ser
                245                 250                 255

Tyr Pro Lys Val Gln Phe Asp Tyr Tyr Gly Gln Gly Thr Leu Val Thr
                260                 265                 270

Val Ser Ser Ala Ala Ala Glu Gln Lys Leu Ile Ser Glu Glu Asp Leu
                275                 280                 285

Asn Gly Ala Ala His His His His His His
290                 295

<210> SEQ ID NO 229
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Arg Arg Asp Leu Val
                35                  40                  45

Ala Ala Ile Asn Ser Val Gly Val Thr Lys Tyr Ala Asp Ser Val Lys
             50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110
```

```
Gln Val Thr Val Ser Ser Gly Gly Gly Gly Ser
            115                 120                 125
Gly Gly Gly Gly Ser Gly Gly Gly Ser Gly Gly Gly Ser Gly
        130                 135                 140
Gly Gly Gly Ser Gly Gly Gly Ser Glu Val Gln Leu Val Glu Ser
145                 150                 155                 160
Gly Gly Gly Ser Val Gln Ala Gly Glu Ser Leu Arg Leu Ser Cys Ala
                165                 170                 175
Ala Ser Gly Ser Ile Phe Ser Ser Asn Ala Met Ala Trp Tyr Arg Gln
            180                 185                 190
Ala Pro Gly Lys Arg Arg Asp Leu Val Ala Ala Ile Asn Ser Val Gly
        195                 200                 205
Val Thr Lys Tyr Ala Asp Ser Val Lys Gly Arg Phe Thr Ile Ser Arg
    210                 215                 220
Asp Asn Ala Lys Asn Thr Val Tyr Leu Gln Met Asn Ser Leu Lys Pro
225                 230                 235                 240
Glu Asp Thr Ala Val Tyr Tyr Cys Thr Ser Asp Pro Arg Arg Gly Trp
                245                 250                 255
Asp Thr Arg Tyr Trp Gly Gln Gly Thr Gln Val Thr Val Ser Ser Ala
            260                 265                 270
Ala Ala Glu Gln Lys Leu Ile Ser Glu Glu Asp Leu Asn Gly Ala Ala
        275                 280                 285
His His His His His His
    290

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 230

His His His His His His
1               5

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Gly Gly Gly Ser Gly Gly Gly Gly Ser Gly Gly Gly Gly Ser
1               5                   10                  15

<210> SEQ ID NO 232
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Gly Gly Gly Ser Gly Gly Gly Ser Gly Gly Gly Gly Ser Gly
1               5                   10                  15

Gly Gly Gly Ser
```

```
<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Gly Gly Gly Ser
1               5

<210> SEQ ID NO 234
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Gly Gly Ser
1

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Gly Gly Ser Ser Gly Gly Gly Ser Ser Gly Gly Gly Ser Ser
1               5                   10                  15
```

CX3CR1-TARGETING IMAGING AGENTS AND THEIR USE IN THE DIAGNOSIS AND TREATMENT OF DISEASE

SEQUENCE LISTING

The instant application contains a Sequence Listing which has been submitted electronically in ASCII format and is hereby incorporated by reference in its entirety. Said ASCII copy, created on Aug. 28, 2014, is named 09-0622-US-2_SL.txt and is 227,056 bytes in size.

FIELD OF THE INVENTION

The present invention relates to CX3CR1-binding polypeptides and their uses in in vivo imaging for the diagnosis and treatment of diseases including atherosclerosis.

BACKGROUND

Cardiovascular diseases are a major cause of death in the United States and other developed countries. Atherosclerosis is a progressive disease of the arterial wall where lipid deposition and chronic inflammation lead to the development of plaque. While most plaques will remain asymptomatic, some may become susceptible to thrombosis (vulnerable) and rupture resulting in myocardial infarctions or strokes. Various imaging modalities have been developed to view the vessel wall (Verjans, 2013; *J. of Cardiovasc. Trans. Res.* ePub June, 2013). Several technologies such as optical coherence tomography (OCT) and intravascular ultrasound (IVUS) can provide information on plaque composition and stability however they require invasive procedures. Another technology utilizes $^{18}$F-fluorodeoxyglucose, a substrate that is taken up by actively metabolizing cells such as plaque macrophages, and can be detected by positron emission tomography (PET). While $^{18}$F-FDG PET has shown clinical utility for monitoring plaque inflammation, it can also be taken up into many tissues nonselectively. New molecular imaging tools are needed to provide insight into the active cellular and molecular processes that drive the progression of atherosclerotic disease and the development of vulnerable plaques. Tools that support the detection of highly inflamed and/or rupture-prone lesions would provide a valuable mechanism for the identification of at-risk patients and for the assessment of the efficacy of novel therapies.

SUMMARY OF THE INVENTION

The present invention provides novel CX3CR1-targeted imaging agents. In another aspect, these imaging agents are useful for diagnosing atherosclerotic disease. In another aspect these imaging agents are useful in selecting or stratifying patients with atherosclerosis who would benefit by treatment with a CX3CR1 antagonist therapeutic or other known treatments for atherosclerotic disease. In a further aspect these imaging agents are useful in diagnosis of diseases characterized by increased tissue expression of CX3CR1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3: Total body SPECT/CT images of the biodistribution of $^{99m}$Tc-CX3CR1BII66B02 and $^{99m}$Tc-CX3CR1BII318 in hCX3CR1 KI ApoE$^{-/-}$ mice that were fed a high fat, high cholesterol diet for 16 weeks. Transverse, coronal and sagittal views enable visualization of the uptake of $^{99m}$Tc-VHH domains into atherosclerotic lesions at the base of the aorta (white arrows). An excess of unlabeled VHH domain was co-administered to demonstrate specificity (+ blocking).

DETAILED DESCRIPTION OF THE INVENTION

Figure 1:
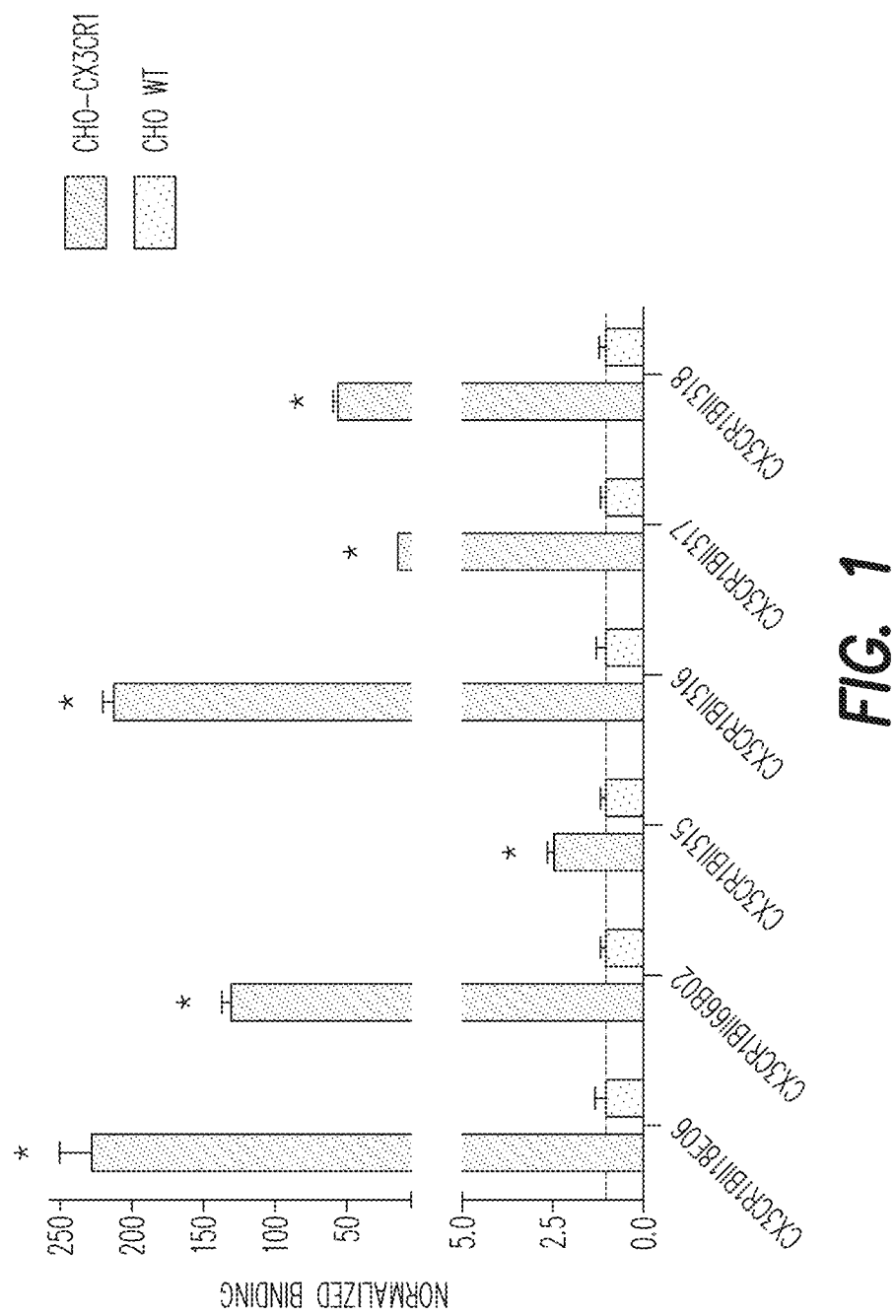
FIG. 1: Normalized binding of $^{99m}$Tc-VHH domains (1 nM) to CHO-hCX3CR1 and CHO-WT cells.

The present invention relates to imaging agents, also known as imaging tracers, based on immunoglobulin single variable domain polypeptides that specifically bind CX3CR1 and their use as diagnostic tools. The imaging agents are comprised of a CX3CR1-targeting single variable domain polypeptide linked to a detection label. The single variable domain polypeptides comprising the imaging agents of the present invention are preferably, but not limited to, VHH domains (or simply "VHHs") from camelids, as defined hereinafter.

CX3CR1 is a G-protein coupled integral membrane protein, and a member of the chemokine receptor family. It has a unique ligand, fractalkine, which is produced as an integral membrane protein. It can also be released into the circulation by proteolytic cleavage. In humans, a CX3CR1 variant (V249I/T280M) with decreased activity has been shown to be associated with a lower risk of cardiovascular disease (coronary heart disease, cerebrovascular disease or peripheral vascular disease) (McDermott, 2001; *Circ. Res.* 89:401), coronary artery disease (angiographic evidence of stenosis) (McDermott, 2003; *J. Clin. Invest.* 111:1241), and carotid artery occlusive disease (Ghilardi, 2004; *Stroke* 35:1276). Several independent mouse genetic studies have shown a beneficial effect of CX3CR1 deficiency on atherosclerosis. A reduction in lesion area in the aortic arch and thoracic aorta as well as a decrease in monocyte/macrophage accumulation in plaques were seen in two independently derived strains of CX3CR1$^{-/-}$ apoE$^{-/-}$ mice fed a high fat diet (Combadière, 2003; *Circulation,* 107:1009, Lesnik, 2003; *J. Clin. Invest.* 111:333).

CX3CR1 is predominantly expressed on cell types such as monocytes, dendritic cells and T cells that have been associated with the initiation and progression of atherosclerotic plaques. It is highly expressed on circulating human intermediate (CD14+CD16+) and non-classical (CD14$^{dim}$CD16+) monocytes (Cros, 2010; *Immunity* 33:375). Increased numbers of circulating CD16+CX3CR1+ monocytes were observed in patients with unstable angina pectoris with evidence of ruptured plaques as determined by intravascular OCT (Ikejima, 2010; *Circ. J.* 74:337). Similarly, increased circulating CD16+ monocytes levels correlated with vulnerable plaque as measured by multidetector computed tomography in patients with stable angina pectoris (Kashiwagii, 2010; *Atherosclerosis* 212:71) and CD14+CD16+ monocyte levels independently predicted cardiovascular events in patients undergoing elective coronary angiography (Ragacev, 2012; *J. Am. Coll. Cardiol.* 60:1512). By immunohistochemistry, CX3CR1 has also been shown to be expressed in human carotid plaques with the number of CX3CR1+ cells increasing with lesion development (Stolla, 2012; *PLOS One* 7:e43572). CX3CR1 appears to be a marker for plaques with elevated levels of inflammation.

Immunoglobulin single variable (VHH) domains are well suited for use as imaging agents (De Vos, 2013; *Expert Opin. Biol. Ther.* 8:1149). One type of VHH is derived from the antigen binding domain of camelid single chain antibodies. Due to their small size (<15 kDa) which leads to rapid clearance from the blood and their high affinity which allows specific target binding, imaging with good signal to background can be carried out shortly after administration enabling the use of short-lived radioisotopes which minimizes patient exposure. VHH domains have also good physicochemical properties and are stable in blood and under conditions required for labeling for use in various imaging modalities. A VHH domain specific for CX3CR1 could provide a valuable non-invasive imaging tool identifying inflamed or unstable plaques and could be utilized for patient selection, stratification, diagnosis, prognosis or monitoring treatment success for new atherosclerosis therapies. It could also be used for in vivo imaging in other diseases characterized by elevated CX3CR1 tissue expression.

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" (2$^{nd}$ Ed.), Gower Medical Publishing, London, New York (1989), as well as to the general background art cited herein; Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein;

Unless indicated otherwise, the terms "immunoglobulin" and "immunoglobulin sequence"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation;

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The terms "immunoglobulin single variable domain" and "single variable domain" as used herein mean an immunoglobulin variable domain which is capable of specifically binding to an epitope of the antigen without pairing with an additional variable immunoglobulin domain. One example of immunoglobulin single variable domains in the meaning of the present invention are "domain antibodies", such as the immunoglobulin single variable domains VH and VL (VH domains and VL domains). Another example of immunoglobulin single variable domains are "VHH domains" (or simply "VHHs") from camelids, as defined hereinafter.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e. by a VH-VL pair of immunoglobulin domains, which jointly bind to an epitope of the respective antigen.

"VHH domains", also known as VHHs, $V_HH$ domains, VHH antibody fragments, and VHH antibodies, have originally been described as the antigen binding immunoglobulin (variable) domain of "heavy chain antibodies" (i.e. of "antibodies devoid of light chains"; C. Hamers-Casterman et al., 1993; *Nature* 363: 446). The term "VHH domain" has been chosen in order to distinguish these variable domains from the heavy chain variable domains that are present in conventional 4-chain antibodies (which are referred to herein as "V$_H$ domains" or "VH domains") and from the light chain variable domains that are present in conventional 4-chain antibodies (which are referred to herein as "V$_L$ domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms VHH domain, VHH, V$_H$H domain, VHH antibody fragment, VHH antibody, as well as "Nanobody®" and "Nanobody® domain" ("Nanobody" being a trademark of the company Ablynx N.V.; Ghent; Belgium) are used interchangeably and are representatives of immunoglobulin single variable domains (having the structure: FR1-CDR1-FR2-CDR2-FR3-CDR3-FR4 and specifically binding to an epitope without requiring the presence of a second immunoglobulin variable domain), and which are distinguished from VH domains by the so-called "hallmark residues", as defined in e.g. WO2009/109635, FIG. 1.

The amino acid residues of a VHH domain are numbered according to the general numbering for V$_H$ domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans, 1999; *J. Immunol. Methods,* 231: 25. According to this numbering, FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for V$_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of V$_H$ domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Further structural characteristics and functional properties of VHH domains and polypeptides containing the same can be summarized as follows:

VHH domains (which have been "designed" by nature to functionally bind to an antigen without the presence of, and without any interaction with, a light chain variable domain) can function as a single, relatively small, functional antigen-binding structural unit, domain or polypeptide. This distinguishes the VHH domains from the VH and VL domains of conventional 4-chain antibodies, which by themselves are generally not suited for practical application as single antigen-binding proteins or immunoglobulin single variable domains, but need to be combined in some form or another to provide a functional antigen-binding unit (as in for example conventional antibody fragments such as Fab fragments; in scFv's, which consist of a VH domain covalently linked to a VL domain).

Because of these unique properties, the use of VHH domains—either alone or as part of a larger polypeptide—offers a number of significant advantages over the use of conventional VH and VL domains, scFv's or conventional antibody fragments (such as Fab- or F(ab')2-fragments):

only a single domain is required to bind an antigen with high affinity and with high selectivity, so that there is no need to have two separate domains present, nor to assure that these two domains are present in the right spacial conformation and configuration (i.e. through the use of especially designed linkers, as with scFv's);
VHH domains can be expressed from a single gene and require no post-translational folding or modifications;
VHH domains can easily be engineered into multivalent and multispecific formats (as further discussed herein);
VHH domains are highly soluble and do not have a tendency to aggregate (as with the mouse-derived antigen-binding domains described by Ward et al., 1989; *Nature,* 341: 544;
VHH domains are highly stable to heat, pH, proteases and other denaturing agents or conditions and, thus, may be prepared, stored or transported without the use of refrigeration equipment, conveying a cost, time and environmental savings;

VHH domains are easy and relatively cheap to prepare, even on a scale required for production. For example, VHH domains and polypeptides containing the same can be produced using microbial fermentation (e.g. as further described below) and do not require the use of mammalian expression systems, as with for example conventional antibody fragments;

VHH domains are relatively small (approximately 15 kDa, or 10 times smaller than a conventional IgG) compared to conventional 4-chain antibodies and antigen-binding fragments thereof, and therefore show high(er) penetration into tissues and can be administered in higher doses than such conventional 4-chain antibodies and antigen-binding fragments thereof;

VHH domains can show so-called cavity-binding properties (inter alia due to their extended CDR3 loop, compared to conventional VH domains) and can therefore also access targets and epitopes not accessible to conventional 4-chain antibodies and antigen-binding fragments thereof.

Methods of obtaining VHH domains binding to a specific antigen or epitope have been described earlier, e.g. in WO2006/040153 and WO2006/122786. As also described therein in detail, VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being. A humanized VHH domain can contain one or more partially or fully human framework region sequences, and, in an even more specific embodiment, can contain human framework region sequences derived from DP-29, DP-47, DP-51, or parts thereof, optionally combined with JH sequences, such as JH5.

The terms "epitope" and "antigenic determinant", which can be used interchangeably, refer to the part of a macromolecule, such as a polypeptide, that is recognized by antigen-binding molecules, such as conventional antibodies or the polypeptides of the invention, and more particularly by the antigen-binding site of said molecules. Epitopes define the minimum binding site for an immunoglobulin, and thus represent the target of specificity of an immunoglobulin.

A polypeptide (such as an immunoglobulin, an antibody, an immunoglobulin single variable domain, a polypeptide of the invention, or generally an antigen binding molecule or a fragment thereof) that can "bind to" or "specifically bind to", that "targets" or "is targeting for" that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g anti-CX3CR1).

Generally, the term "specificity" refers to the number of different types of antigens or epitopes to which a particular antigen-binding molecule or antigen-binding protein (such as an immunoglobulin, an antibody, an immunoglobulin single variable domain, or a polypeptide of the invention) can bind. The specificity of an antigen-binding protein can be determined based on its affinity and/or avidity. The affinity, represented by the equilibrium constant for the dissociation of an antigen with an antigen-binding protein (KD), is a measure for the binding strength between an epitope and an antigen-binding site on the antigen-binding protein: the lesser the value of the KD, the stronger the binding strength between an epitope and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin, an antibody, an immunoglobulin single variable domain, or a polypeptide of the invention) and the pertinent antigen. Avidity is related to both the affinity between an epitope and its antigen binding site on the antigen-binding molecule and the number of pertinent binding sites present on the antigen-binding molecule.

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, for example from WO 98/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows:

Ala into Gly or into Ser;
Arg into Lys;
Asn into Gln or into His;
Asp into Glu;
Cys into Ser;
Gln into Asn;
Glu into Asp;
Gly into Ala or into Pro;
His into Asn or into Gln;
Ile into Leu or into Val;
Leu into Ile or into Val;
Lys into Arg, into Gln or into Glu;
Met into Leu, into Tyr or into Ile;
Phe into Met, into Leu or into Tyr;
Ser into Thr;
Thr into Ser;
Trp into Tyr;
Tyr into Trp or into Phe;
Val into Ile or into Leu.

"Sequence identity" between e.g. two immunoglobulin single variable domain sequences indicates the percentage of amino acids that are identical between these two sequences. It may be calculated or determined as described in paragraph f) on pages 49 and 50 of WO08/020079. "Sequence similarity" indicates the percentage of amino acids that either are identical or that represent conservative amino acid substitutions.

Target Specificity

The CX3CR1-targeting polypeptides of the invention have specificity for human CX3CR1. Thus, the imaging agents of the invention comprising CX3CR1-targeting polypeptides and a detection label preferably bind to human CX3CR1 (SEQ ID NO:230).

The CX3CR1-targeting polypeptide portion of the imaging agents described herein is comprised of VHH domains. Representative VHH domains have CDR sequences shown in Tables 1, 2, 3 (representative polypeptides of families 101, 9 and 13, respectively) and 4 (representative polypeptides of optimized variants of family 101. An optimized variant is humanized and/or optimized for stability, potency, manufacturability and/or similarity to human framework regions.

TABLE 1

Family 101

| VHH domain | SEQ | CDR1* | SEQ CDR1 | CDR2* | SEQ CDR2 | CDR3* | SEQ CDR3 |
|---|---|---|---|---|---|---|---|
| CX3CR1BI IPMP66B02 | 1 | GSIFSSNAMA | 141 | AINSVGVTK | 162 | DPRRGWDTRY | 186 |
| CX3CR1BI IPMP54A12 | 2 | GSIFSSNAMA | 141 | VINSVGITK | 163 | DARRGWDTRY | 187 |
| CX3CR1BI IPMP54A3 | 3 | GSIFSSNAMA | 141 | GINSVGITK | 164 | DPRRGWDTRY | 186 |
| CX3CR1BI IPMP54A4 | 4 | GSIFSSNAMA | 141 | GINSVGITK | 164 | DPRRGWDTRY | 186 |
| CX3CR1BI IPMP54A5 | 5 | GSIFSSNAMA | 141 | GINSVGITK | 164 | DPRRGWDTRY | 186 |
| CX3CR1BI IPMP54A7 | 6 | GTIFSSNAMA | 142 | GINSVDITK | 165 | DPRRGWNTRY | 188 |
| CX3CR1BI IPMP54B1 | 7 | GSIFSSNAMA | 141 | GINSVGITK | 164 | DPRRGWDTRY | 186 |
| CX3CR1BI IPMP54B2 | 8 | GTIFSSNAMA | 142 | GINSVDITK | 165 | DPRRGWNTRY | 188 |
| CX3CR1BI IPMP54B3 | 9 | GSIFSSNAMA | 141 | AINSVGITK | 166 | DPRRGWDTRY | 186 |
| CX3CR1BI IPMP54B5 | 10 | GSIFSSNAMA | 141 | GINSVGITK | 164 | DPRRGWDTRY | 186 |
| CX3CR1BI IPMP54D5 | 11 | GSIFSSNAMA | 141 | LINSVGITK | 167 | DGRRGWDTRY | 189 |
| CX3CR1BI IPMP54D8 | 12 | GSIFSSNAMA | 141 | GINSVGITK | 164 | DPRRGWDTRY | 186 |
| CX3CR1BI IPMP54F6 | 13 | GSIFSSNAMA | 141 | AINSVGITK | 166 | DPRRGWDTRY | 186 |
| CX3CR1BI IPMP54G3 | 14 | GSIFSSNAMA | 141 | LINSVGITK | 167 | DPRRGWDTRY | 186 |
| CX3CR1BI IPMP54H1 | 15 | GTIFSSNAMA | 142 | GINSVDITK | 165 | DPRRGWNTRY | 188 |
| CX3CR1BI IPMP54H4 | 16 | GSIFSSNAMA | 141 | VINSVGITK | 163 | DARRGWDTRY | 187 |
| CX3CR1BI IPMP61F10 | 17 | GTIFSSNAMA | 142 | GINSVDITK | 165 | DPRRGWNTRY | 188 |
| CX3CR1BI IPMP61D1 | 18 | GSIFSSNAMA | 141 | LINSVGITK | 167 | DPRRGWDTRY | 186 |
| CX3CR1BI IPMP61D5 | 19 | GSIFSSNAMA | 141 | LINSVGITK | 167 | DPRRGWDTRY | 186 |
| CX3CR1BI IPMP61E2 | 20 | GSIFSSNAMA | 141 | GINSVGITK | 164 | DPRRGWDTRY | 186 |
| CX3CR1BI IPMP61F1 | 21 | GSIFSSNAMA | 141 | AINSVGITK | 166 | DPRRGWDTRY | 186 |
| CX3CR1BI IPMP61G2 | 22 | GSIFSSNAMA | 141 | LINSVGITK | 167 | DPRRGWDTRY | 186 |
| CX3CR1BI IPMP61G3 | 23 | GSIFSSNAMA | 141 | AINSVGITK | 166 | DPRRGWDTRY | 186 |
| CX3CR1BI IPMP61G4 | 24 | GSIFSSNAMA | 141 | AINSVGITK | 166 | DPRRGWDTRY | 186 |
| CX3CR1BI IPMP61F4 | 25 | GSIFSSNAMA | 141 | VINTVGITK | 168 | DARRGWDTRY | 187 |
| CX3CR1BI IPMP61A1 | 26 | GSIFSSNAMA | 141 | VINSVGITK | 163 | DARRGWDTRY | 187 |
| CX3CR1BI IPMP61B2 | 27 | GSIFSSNAMA | 141 | VINTVGITK | 168 | DARRGWDTRY | 187 |
| CX3CR1BI IPMP61C9 | 28 | GSIFSSNAMA | 141 | LIDSAGITK | 169 | DARRGWNTKY | 190 |
| CX3CR1BI IPMP65H02 | 29 | GSIFSSNAMA | 141 | AINSVGITK | 166 | DPRRGWDTRY | 186 |
| CX3CR1BI IPMP65E11 | 30 | GSIFSSNAMA | 141 | GINSVGIAK | 170 | DPRRGWDTRY | 186 |
| CX3CR1BI IPMP65E10 | 31 | GSIFSSNAKA | 143 | GINSVGITK | 164 | DPRRGWDTRY | 186 |
| CX3CR1BI IPMP65E05 | 32 | GSIFSSNAMA | 141 | GINSVGITK | 164 | DPRRGWDTRY | 186 |
| CX3CR1BI IPMP65B11 | 33 | GSIFSSNAMA | 141 | VINKVGITK | 171 | DPRRGWDTRY | 186 |
| CX3CR1BI IPMP65B07 | 34 | GSIFSSNAMA | 141 | AINSVGITK | 166 | DPRRGWDTRY | 186 |
| CX3CR1BI IPMP65B09 | 35 | GSIFSRNAMA | 144 | SINSVGITK | 172 | DARRGWDTRY | 187 |
| CX3CR1BI IPMP65H01 | 36 | GGIFSRNAMA | 145 | SINSVGITK | 172 | DARRGWDTRY | 187 |
| CX3CR1BI IPMP65G07 | 37 | GTIFSSNAMA | 142 | GINSVDITR | 173 | DPRRGWNTRY | 188 |

TABLE 1-continued

Family 101

| VHH domain | SEQ | CDR1* | SEQ CDR1 | CDR2* | SEQ CDR2 | CDR3* | SEQ CDR3 |
|---|---|---|---|---|---|---|---|
| CX3CR1BIIPMP66H08 | 38 | GSIFSSNAMA | 141 | LINSVGITK | 167 | DPRRGWDTRY | 186 |
| CX3CR1BIIPMP66H04 | 39 | GSIFSSNAMA | 141 | AINSVGITK | 166 | DPRRGWDTRY | 186 |
| CX3CR1BIIPMP66F02 | 40 | GSIFSSNAMA | 141 | LINSVGITK | 167 | DPRRGWDTRY | 186 |
| CX3CR1BIIPMP66E11 | 41 | GSIFSSNAMA | 141 | AINSVGTTK | 174 | DPRRGWDTRY | 186 |
| CX3CR1BIIPMP66D10 | 42 | GSIFSSNAMA | 141 | LINSVGITK | 167 | DPRRGWDTRY | 186 |
| CX3CR1BIIPMP66D08 | 43 | GSIFSSNAMA | 141 | GINSVGITK | 164 | DPRRGWDTRY | 186 |
| CX3CR1BIIPMP66A04 | 44 | GSIFSSNAMA | 141 | LINSVGITK | 167 | DPRRGWDTRY | 186 |
| CX3CR1BIIPMP66D04 | 45 | GTIFSSNAMA | 142 | GINSVDITK | 165 | DPRRGWNTRY | 188 |
| CX3CR1BIIPMP66D02 | 46 | GSIFSSNAMA | 141 | VINSVGITK | 163 | DARRGWDTRY | 187 |
| CX3CR1BIIPMP66D06 | 47 | GSIFSSNAMA | 141 | SIDSVGITK | 175 | DARRGWDTRY | 187 |
| CX3CR1BIIPMP66G01 | 48 | GSIFSSNAMA | 141 | LINSVGITK | 167 | DGRRGWDTRY | 189 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

TABLE 2

Family 9

| VHH domain | SEQ | CDR1* | SEQ CDR1 | CDR2* | SEQ CDR2 | CDR3* | SEQ CDR3 |
|---|---|---|---|---|---|---|---|
| CX3CR1BIIPMP11H1 | 49 | GRTFSSYAMG | 146 | GISGSASRKY | 176 | SNSYPKVQFDY | 191 |
| CX3CR1BIIPMP12B6 | 50 | GRTFSSYAMG | 146 | GISGSASRKY | 176 | SNSYPKVQFDY | 191 |
| CX3CR1BIIPMP12G9 | 51 | GRTFSSYAMG | 146 | GISGSGSRKY | 177 | SNSYPKVQFDY | 191 |
| CX3CR1BIIPMP15G11 | 52 | GRTFSSYAMG | 146 | GISGSGSRKY | 177 | SNSYPKVQFDY | 191 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

TABLE 3

Family 13

| VHH domain | SEQ | CDR1* | SEQ CDR1 | CDR2* | SEQ CDR2 | CDR3* | SEQ CDR3 |
|---|---|---|---|---|---|---|---|
| CX3CR1BIIPMP18E6 | 53 | GTIFSNNAMG | 147 | SISSSGSTN | 178 | DARRGWNTAY | 192 |
| CX3CR1BIIPMP12C2 | 54 | GTIFSNTAMG | 148 | SISNSGSTN | 179 | DARRGWNSGY | 193 |
| CX3CR1BIIPMP18A10 | 55 | GIIFSNNAMG | 149 | SISNSGSTN | 179 | DARRGWNTAY | 192 |
| CX3CR1BIIPMP18A2 | 56 | GIIFSNNAMG | 149 | SIGSTYSTN | 180 | DARRGWNTAY | 192 |
| CX3CR1BIIPMP18A8 | 57 | RTIFSRNAMG | 150 | SISNSGSTN | 179 | DARRGWNTGY | 194 |
| CX3CR1BIIPMP18A9 | 58 | GIIFSNNAMG | 149 | SISSTYSTN | 181 | DARRGWNTAY | 192 |
| CX3CR1BIIPMP18B7 | 59 | GTIFSRNAMG | 151 | SISNSGSTN | 179 | DARRGWNSGY | 193 |
| CX3CR1BIIPMP18B9 | 60 | GTIFSNNAMG | 147 | SISSSGSTN | 178 | DARRGWNTAY | 192 |
| CX3CR1BIIPMP18C6 | 61 | GTIFSNNAMG | 147 | SISNSGSTN | 179 | DARRGWNTAY | 192 |
| CX3CR1BIIPMP18C9 | 62 | GIIFSNNAMG | 149 | SISNSGSTN | 179 | DARRGWNTAY | 192 |
| CX3CR1BIIPMP18D1 | 63 | GIIFSNNAMG | 149 | SISNSGSTN | 179 | DARRGWNTAY | 192 |
| CX3CR1BIIPMP18D10 | 64 | GTIFSNNAMG | 147 | SISNSGSTN | 179 | DARRGWNTAY | 192 |
| CX3CR1BIIPMP18D12 | 65 | GTIFSNNAMG | 147 | SISNSGSTN | 179 | DARRGWNTAY | 192 |
| CX3CR1BIIPMP18F1 | 66 | GTIFSNNAMG | 147 | SISNSGSTN | 179 | DARRGWNTAY | 192 |
| CX3CR1BIIPMP18F5 | 67 | GTIFSNNAMG | 147 | SISNSGSTN | 179 | DARRGWNTAY | 192 |
| CX3CR1BIIPMP18F6 | 68 | GTIFSNNAMG | 147 | SISNSGSTN | 179 | DARRGWNTAY | 192 |
| CX3CR1BIIPMP18F9 | 69 | GTIFRTNAMG | 152 | SISNSGSTN | 179 | DGRRGWNTGY | 195 |
| CX3CR1BIIPMP18G5 | 70 | RTIFSRNAMG | 150 | SISNSGSTN | 179 | DARRGWNTGY | 194 |
| CX3CR1BIIPMP18H1 | 71 | GTIFSNNAMG | 147 | SISNSGSTN | 179 | DARRGWNTAY | 192 |
| CX3CR1BIIPMP18H10 | 72 | KTIFSRNAMG | 153 | SISNSGSTN | 179 | DARRGWNTGY | 194 |
| CX3CR1BIIPMP18H7 | 73 | GIIFSNNAMG | 149 | SISNSGSTN | 179 | DARRGWNTAY | 192 |
| CX3CR1BIIPMP18H9 | 74 | GTIFSNNAMG | 147 | SISNSGSTN | 179 | DARRGWNTAY | 192 |
| CX3CR1BIIPMP20B3 | 75 | GIIFSNNAMG | 149 | SIGSTYSTN | 180 | DARRGWNTAY | 192 |

TABLE 3-continued

Family 13

| VHH domain | CDR1* | SEQ CDR1 | CDR2* | SEQ CDR2 | CDR3* | SEQ CDR3 |
|---|---|---|---|---|---|---|
| CX3CR1BIIPMP20C12 | GTIFRSNAMG | 76 | SISNSGSTN | 151 | DARRGWNSGY | 179 193 |
| CX3CR1BIIPMP20C3 | GIIFSNNAMG | 77 | SISNSGSTN | 149 | DARRGWNTAY | 179 192 |
| CX3CR1BIIPMP20C6 | GTIFSNNAMG | 78 | SISNSGSTN | 147 | DARRGWNTAY | 179 192 |
| CX3CR1BIIPMP20D8 | GTTFSNAMG | 79 | SITNSGSTN | 154 | DARRGWNTGY | 182 194 |
| CX3CR1BIIPMP20E1 | RTIFRSNAMG | 80 | SITNSGSTN | 150 | DARRGWNTGY | 182 194 |
| CX3CR1BIIPMP20E5 | GTIFSNNAMG | 81 | SISNSGSTN | 147 | DARRGWNTGY | 179 194 |
| CX3CR1BIIPMP20F3 | GTIFSNNAMG | 82 | SISSSGSTN | 147 | DARRGWNTAY | 178 192 |
| CX3CR1BIIPMP20F4 | ATIFRSNAMG | 83 | SISNSGSTN | 155 | DGRRGWNTGY | 179 195 |
| CX3CR1BIIPMP20F5 | ATIFRSNAMG | 84 | SISNSGSTN | 155 | DGRRGWNTGY | 179 195 |
| CX3CR1BIIPMP21B6 | GTIFSNNAMG | 85 | SISNSGSTN | 147 | DARRGWNTAY | 179 192 |
| CX3CR1BIIPMP24A12 | GIIFSNNAMG | 86 | SISNSGSAN | 149 | DARRGWNTAY | 183 192 |
| CX3CR1BIIPMP24A6 | GTIFSNNAMG | 87 | SISNSGSTN | 147 | DARRGWNTAY | 179 192 |
| CX3CR1BIIPMP24B9 | GTIFRSNAMG | 88 | SISISGSTN | 151 | DARRGWNTGF | 184 196 |
| CX3CR1BIIPMP24D3 | GIIFSNNAMG | 89 | SISSTYSTN | 149 | DARRGWNTAY | 181 192 |
| CX3CR1BIIPMP24F7 | GLIFSNNAMG | 90 | SISSTYSTN | 156 | DARRGWNTAY | 181 192 |
| CX3CR1BIIPMP28B4 | ATIFRSNAMG | 91 | SISNSGSTN | 155 | DGRRGWNTGY | 179 195 |
| CX3CR1BIIPMP28F1 | GIIFSNNAMG | 92 | SIGSTYSTN | 149 | DARRGWNTAY | 180 192 |
| CX3CR1BIIPMP28F6 | GIIFSNNAMG | 93 | SIGSTYSTN | 149 | DARRGWNTAY | 180 192 |
| CX3CR1BIIPMP28F9 | GTIFSNNAMG | 94 | SISNSGSTN | 147 | DARRGWNTGY | 179 194 |
| CX3CR1BIIPMP29A5 | GTIFSNNAMG | 95 | SISNSGSTN | 147 | DARRGWNTAY | 179 192 |
| CX3CR1BIIPMP29D5 | GTIFRSNAMG | 96 | SISNSGSTN | 151 | DARRGWNSGY | 179 193 |
| CX3CR1BIIPMP29E3 | KTIFRSNAMG | 97 | SISNSGSTN | 153 | DARRGWNTGY | 179 194 |
| CX3CR1BIIPMP29E7 | KTIFRSNAMG | 98 | SISNSGSTN | 153 | DARRGWNTGY | 179 194 |
| CX3CR1BIIPMP29G10 | GTIFRSNAMG | 99 | SITNSGSTN | 151 | DARRGWNTGY | 182 194 |
| CX3CR1BIIPMP29G7 | GIIFSNNAMG | 100 | SITNTGSTN | 149 | DARRGWNTAY | 185 192 |
| CX3CR1BIIPMP29H1 | GTIFSNNAMG | 101 | SISNSGSTN | 147 | DARRGWNTAY | 179 192 |
| CX3CR1BIIPMP37A8 | RTIFRSNAMG | 102 | SISNSGSTN | 150 | DARRGWNTGY | 179 194 |
| CX3CR1BIIPMP37B9 | GTIFSNNAMG | 103 | SISNSGSTN | 147 | DARRGWNTAY | 179 192 |
| CX3CR1BIIPMP37C12 | GSIFRSNAMG | 104 | SISNSGSTN | 157 | DARRGWNTGY | 179 194 |
| CX3CR1BIIPMP37C7 | RTIFSNNAMG | 105 | SISNSGSTN | 158 | DARRGWNTAY | 179 192 |
| CX3CR1BIIPMP37D9 | GTVFSNNAMG | 106 | SISSSGSTN | 159 | DARRGWNTAY | 178 192 |
| CX3CR1BIIPMP37E12 | KPIFRSNAMG | 107 | SISNSGSTN | 160 | DARRGWNTGY | 179 194 |
| CX3CR1BIIPMP41B10 | GTIFSNNAMG | 108 | SISNSGSTN | 147 | DARRGWNTAY | 179 192 |
| CX3CR1BIIPMP41B11 | GTIFSNNAMG | 109 | SISNSGSTN | 147 | DARRGWNTAY | 179 192 |
| CX3CR1BIIPMP41B8 | GIIFSNNAMG | 110 | SIGSTYSTN | 149 | DARRGWNTAY | 180 192 |
| CX3CR1BIIPMP41C10 | RTIFRSNAMG | 111 | SISNSGSTN | 150 | DARRGWNTGY | 179 194 |
| CX3CR1BIIPMP41F9 | GIIFSNNAMG | 112 | SIGSTYSTN | 149 | DARRGWNTAY | 180 192 |
| CX3CR1BIIPMP41H10 | GLTLDDYAMG | 113 | SISNSGSTN | 161 | DARRGWNTGY | 179 194 |
| CX3CR1BIIPMP46B5 | RTIFRSNAMG | 114 | SISNSGSTN | 150 | DARRGWNTGY | 179 194 |
| CX3CR1BIIPMP46D3 | GTIFSNNAMG | 115 | SISNSGSTN | 147 | DARRGWNTGY | 179 194 |
| CX3CR1BIIPMP46H5 | GIIFSNNAMG | 116 | SISSTYSTN | 149 | DARRGWNTAY | 181 192 |
| CX3CR1BIIPMP48B8 | KTIFRSNAMG | 117 | SISNSGSTN | 153 | DARRGWNTGY | 179 194 |
| CX3CR1BIIPMP48D11 | RTIFRSNAMG | 118 | SISNSGSTN | 150 | DARRGWNTGY | 179 194 |
| CX3CR1BIIPMP48G8 | RTIFRSNAMG | 119 | SISNSGSTN | 150 | DARRGWNTGY | 179 194 |

TABLE 3-continued

Family 13

| VHH domain | SEQ CDR1* | CDR1 | SEQ CDR2* | CDR2 | SEQ CDR3* | CDR3 |
|---|---|---|---|---|---|---|
| CX3CR1BI IPMP48H9 | 120 | GTIFSNN AMG | 147 | SISNSGST N | 179 | DARRGW NTAY | 192 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

TABLE 4

Optimized variants

| VHH domain | SEQ CDR1 | CDR1 | SEQ CDR2 | CDR2 | SEQ CDR3 | CDR3 |
|---|---|---|---|---|---|---|
| CX3CR1BI IPMP66B02 | 1 | GSIFSSNA MA | 141 | AINSVGV TK | 162 | DPRRGW DTRY | 186 |
| CX3CR1BI I043 | 121 | GSIFSSNA MA | 141 | AINSVGV TK | 162 | DPRRGW DTRY | 186 |
| CX3CR1BI I045 | 122 | GSIFSSNA MA | 141 | AINSVGV TK | 162 | DPRRGW DTRY | 186 |
| CX3CR1BI I047 | 123 | GSIFSSNA MA | 141 | AINSVGV TK | 162 | DPRRGW DTRY | 186 |
| CX3CR1BI I048 | 124 | GSIFSSNA MA | 141 | AINSVGV TK | 162 | DPRRGW DTRY | 186 |
| CX3CR1BI I049 | 125 | GSIFSSNA MA | 141 | AINSVGV TK | 162 | DPRRGW DTRY | 186 |
| CX3CR1BI I050 | 126 | GSIFSSNA MA | 141 | AINSVGV TK | 162 | DPRRGW DTRY | 186 |
| CX3CR1BI I061 | 127 | GSIFSSNA MA | 141 | AINSVGV TK | 162 | DPRRGW DTRY | 186 |
| CX3CR1BI I056 | 128 | GSIFSSNA MA | 141 | AINSVGV TK | 162 | DPRRGW DTRY | 186 |
| CX3CR1BI I057 | 129 | GSIFSSNA MA | 141 | AINSVGV TK | 162 | DPRRGW DTRY | 186 |
| CX3CR1BI I060 | 130 | GSIFSSNA MA | 141 | AINSVGV TK | 162 | DPRRGW DTRY | 186 |
| CX3CR1BI I065 | 131 | GSIFSSNA MA | 141 | AISSVGV TK | 214 | DPRRGW DTRY | 186 |
| CX3CR1BI I067 | 132 | GSIFSSNA MA | 141 | AIQSVGV TK | 215 | DPRRGW DTRY | 186 |
| CX3CR1BI I068 | 133 | GSIFSSNA MA | 141 | AIGSVGV TK | 216 | DPRRGW DTRY | 186 |
| CX3CR1BI I074 | 134 | GSIFSSNA MA | 141 | AITSVGV TK | 217 | DPRRGW DTRY | 186 |
| CX3CR1BI I118 | 135 | GSIFSSNA MA | 141 | AINTVGV TK | 218 | DPRRGW DTRY | 186 |
| CX3CR1BI I129 | 136 | GSIFSSNA MA | 141 | AINGVGV TK | 219 | DPRRGW DTRY | 186 |
| CX3CR1BI I158 | 137 | GSIFSSNA MA | 141 | AINPVGV TK | 220 | DPRRGW DTRY | 186 |
| CX3CR1BI I306 | 138 | GSIFSSTA MA | 213 | AISSVGV TK | 214 | DPRRGW DTRY | 186 |
| CX3CR1BI I307 | 139 | GSIFSSTA MA | 213 | AISTVGV TK | 221 | DPRRGW DTRY | 186 |
| CX3CR1BI I308 | 140 | GSIFSSNA MA | 141 | AINSVGV TK | 162 | DPRRGW DTRY | 186 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

Representative sequences of VHH domains that may comprise the CX3CR1-targeting polypeptide portion of the imaging agents described herein are shown in Tables 5 and 6 below:

TABLE 5

VHH domains
SEQ ID NO: 1-48 are VHH domains of family 101. SEQ ID NO: 49-52 are VHH domains of family 9. SEQ ID NO: 53-120 are VHH domains of family 13.

| | | |
|---|---|---|
| CX3CR1BI IPMP66B02 | EVQLVESGGGSVQAGESLRLSCAASGSIFSSNA MAWYRQAPGKRRDLVAAINSVGVTKYADSVK GRFTISRDNAKNTVYLQMNSLKPEDTAVYYCT SDPRRGWDTRYWGQGTQVTVSS | SEQ ID NO: 1 |
| CX3CR1BI IPMP54A1 | EVQLVESGGGSVQAGESLRLSCAASGSIFSSNA MAWYRQAPGKQRDLVAVINSVGITKYADSVK GRFTISGDNAKNTVYLQMNSLKPEDTAVYYCT SDARRGWDTRYWGQGTQVTVSS | SEQ ID NO: 2 |
| CX3CR1BI IPMP54A3 | EVQLVESGGGSVQAGESLRLSCAASGSIFSSNA MAWYRQAPGKQRDLVAGINSVGITKYADSVK GRFTISRDNAKNTVYLQMNSLKPEDTAVYYCT SDPRRGWDTRYWGQGTQVTVSS | SEQ ID NO: 3 |
| CX3CR1BI IPMP54A4 | EVQLVESGRGSVQAGESLRLSCAASGSIFSSNA MAWYRQAPGKQRDLVAGINSVGITKYADSVK GRFTISRDNAKNTVYLQMNSLKPEDTAVYYCT SDPRRGWDTRYWGQGTQVTVSS | SEQ ID NO: 4 |
| CX3CR1BI IPMP54A5 | EVQLVESGGGSVQAGESLRLSCAASGSIFSSNA MAWYRQAPGKQRDLVAGINSVGITKYADSVK GRFTISRDNAKNTVYLQMNSLKPEDTAVYYCT SDPRRGWDTRYWGQGTLVTVSS | SEQ ID NO: 5 |
| CX3CR1BI IPMP54A7 | EVQLVESGGGSVQAGESLRLSCAASGTIFSSNA MAWYRQAPGKQRDLVAGINSVDITKYADSVK GRFTISRDNAKNTVYLQMNSLKPEDTAVYYCT SDPRRGWNTRYWGQGTQVTVSS | SEQ ID NO: 6 |
| CX3CR1BI IPMP54B1 | EVQLVESGGGSVQAGESLRLSCAASGSIFSSNA MAWYRQAPGKQRDLVAGINSVGITKYADSVK GRFTISRDNAKNTAYLQMNSLKPEDTAVYYCT SDPRRGWDTRYWGQGTQVTVSS | SEQ ID NO: 7 |
| CX3CR1BI IPMP54B2 | EVQLVESGGGSVQAGESLRLSCAASGTIFSSNA MAWYRQAPGKQRDLVAGINSVDITKYADSVK GRFTISRDNAKNTVYLQMNSLKPEDTAVYYCT SDPRRGWNTRYWGQGTLVTVSS | SEQ ID NO: 8 |
| CX3CR1BI IPMP54B3 | EVQLVESGGGSVQAGESLRLSCAASGSIFSSNA MAWYRQAPGKQRDLVAAINSVGITKYADSVK GRFTISRDNAKNTVYLQMNSLKPEDTAVYYCT SDPRRGWDTRYWGQGTQVTVSS | SEQ ID NO: 9 |
| CX3CR1BI IPMP54B5 | EVQLVESGGGSVQAGESLRLSCAASGSIFSSNA MAWYRQAPGKQRDLVAGINSVGITKYADSVK GRFTISRDNAKNTAYLQMNSLKPEDTAVYYCT SDPRRGWDTRYWGQGTLVTVSS | SEQ ID NO: 10 |

TABLE 5-continued

VHH domains
SEQ ID NO: 1-48 are VHH domains of family 101. SEQ ID NO: 49-52 are VHH domains of family 9. SEQ ID NO: 53-120 are VHH domains of family 13.

CX3CR1BIIPMP54D5 EVQLVESGGGSVQAGESLRLSCAASGSIFSSNAMAWYRQAPPGKQRDLVALINSVGITKYADSVKGRFTISSDNAKNTVYLEMNSLKPEDTAVYYCTSDGRRGWDTRYWGQGTQVTVSS SEQ ID NO: 11

CX3CR1BIIPMP54D8 EVQLVESGGGSVQAGGSLRLSCAASGSIFSSNAMAWYRQAPGKQRDLVAGINSVGITKYADSVKGRFTISRDNAKNTVYLQMNSLKPEDTAVYYCTSDPRRGWDTRYWGQGTLVTVSS SEQ ID NO: 12

CX3CR1BIIPMP54F6 KVQLVESGGGSVQAGESLRLSCAASGSIFSSNAMAWYRQAPGKQRDLVAAINSVGITKYADSVKGRFTISRDNAKNTVYLQMNSLKPEDTAVYYCTSDPRRGWDTRYWGQGTLVTVSS SEQ ID NO: 13

CX3CR1BIIPMP54G3 EVQLVESGGGSVQAGESLRLSCAASGSIFSSNAMAWYRQAPGKQRDLVALINSVGITKYADSVKGRFTISRDNAKNTVYLQMNSLKPEDTAVYYCTSDPRRGWDTRYWGQGTLVTVSS SEQ ID NO: 14

CX3CR1BIIPMP54H1 EVQLVESGGGSVQAGESLRLSCAASGTIFSSNAMAWYRQAPGKQRDLVAGINSVDITKYADSVKGRFTVSRDNAKNTVYLQMNSLKPEDTAVYYCTSDPRRGWNTRYWGQGTQVTVSS SEQ ID NO: 15

CX3CR1BIIPMP54H4 EVQLVESGGGSVQAGESLRLSCAASGSIFSSNAMAWYRQAPGKQRDLVAVINSVGITKYADSVKGRFTISGDNAKNTVYLQMNSLKPEDTAVYYCTSDARRGWDTRYWGQGTLVTVSS SEQ ID NO: 16

CX3CR1BIIPMP61F10 KVQLVESGGGSVQAGESLRLSCAASGTIFSSNAMAWYRQAPGKQRDLVAGINSVDITKYADSVKGRFTISRDNAKNTVYLQMNSLKPEDTAVYYCTSDPRRGWNTRYWGQGTQVTVSS SEQ ID NO: 17

CX3CR1BIIPMP61D1 EVQLVESGGGSVQAGESLRLSCAASGSIFSSNAMAWYRQAFGKQRDLVALINSVGITKYADSVKGRFTISRDNAKNTVYLQMNSLKPEDTAVYYCTSDPRRGWDTRYWGQGTQVTVSS SEQ ID NO: 18

CX3CR1BIIPMP61D5 KVQLVESGGGSVQAGESLRLSCAASGSIFSSNAMAWYRQAFGKQRDLVALINSVGITKYADSVKGRFTISRDNAKNTVYLQMNSLKPEDTAVYYCTSDPRRGWDTRYWGQGTQVTVSS SEQ ID NO: 19

CX3CR1BIIPMP61E2 EVQLVESGGGSVQAGESLRLSCAASGSIFSSNAMAWYRQAPGKQRDLVAGINSVGITKYADSVKGRFTISRDNAKNTVYLQMNSLKPEDMAVYYCTSDPRRGWDTRYWGQGTQVTVSS SEQ ID NO: 20

CX3CR1BIIPMP61F11 KVQLVESGGGSVQAGESLRLSCAASGSIFSSNAMAWYRQPPGKQRDLVAAINSVGITKYADSVKGRFTIFRDNAKNTVYLQMNSLKPEDTAVYYCTSDPRRGWDTRYWGQGTQVTVSS SEQ ID NO: 21

CX3CR1BIIPMP61G2 EVQLVKSGGGSVQAGESLRLSCAASGSIFSSNAMAWYRQAPGKQRDLVALINSVGITKYADSVKGRFTISRDNAKNTVYLQMNSLKPEDTAVYYCTSDPRRGWDTRYWGQGTQVTVSS SEQ ID NO: 22

CX3CR1BIIPMP61G3 KVQLVESGGGSMQAGESLRLSCAASGSIFSSNAMAWYRQAPGKQRDLVAAINSVGITKYADSVKGRFTISRDNAKNTVYLQMMSLKPEDTAVYYCTSDPRRGWDTRYWGQGTQVTVSS SEQ ID NO: 23

CX3CR1BIIPMP61G4 KVQLVESGGGSVQAGGSLRLSCAASGSIFSSNAMAWYRQAPGKQRDLVAGINSVGITKYADSVKGRFTISRDNAKNTVYLQMNSLKPEDTAVYYCTSDPRRGWDTRYWGQGTQVTVSS SEQ ID NO: 24

CX3CR1BIIPMP61F4 EVQLVESGGGSVQAGASLRLSCAASGSIFSSNAMAWYRQAPGKQRDLVAVINTVGITKYADSVKGRFTISRDNAKNTVYLQMNSLKPEDTAVYYCTSDARRGWDTRYWGQGTLVTVSS SEQ ID NO: 25

CX3CR1BIIPMP61A11 MAWYRQAPGKQRDLVAVINSVGITKYADSVKGRFTISGDNAKNTVYLQMNSLKPEDTAVYYCTSDARRGWDTRYWGQGTQVTVSS SEQ ID NO: 26

CX3CR1BIIPMP61B2 EVQLVESRGGSVQAGASLRLSCAASGSIFSSNAMAWYRQAPGKQRDLVAVINTVGITKYADSVKGRFTISRDNAKNTVYLQMNSLKPEDTAVYYCTSDARRGWDTRYWGQGTQVTVSS SEQ ID NO: 27

CX3CR1BIIPMP61C9 EVQLVKSGGGSVQAGESLRLSCAASGSIFSSNAMAWYRQALGKQRDLVALIDSAGITKYADSVKGRFTISRDNAKNTVYLQMNRLKPEDTAVYYCASDARRGWNTKYWGQGTLVTVSS SEQ ID NO: 28

CX3CR1BIIPMP65H02 EVQLVESGGGSVQAGESLRLSCAASGSIFSSNAMAWYRQAPGKQRDLVAAINSVGITKYADSVKGRFTISRDNAKNTVHLQMNSLKPEDTAVYYCSDPRRGWDTRYWGQGTLVTVSS SEQ ID NO: 29

CX3CR1BIIPMP65E11 EVQLVESGGGSVQAGESLRLSCAASGSIFSSNAMAWYRQAPGKQRDLVAGINSVGIAKYADSVKGRFTISRDNAKNTVYLQMNSLKPEDTAVYYCSDPRRGWDTRYWGQGTLVTVSS SEQ ID NO: 30

CX3CR1BIIPMP65E10 KAWYRQAPGKQRDLVAGINSVGITKYADSVKGRFTISRDNAKNTVYLQMNSLKPEDTAVYYCSDPRRGWDTRYWGQGTLVTVSS SEQ ID NO: 31

CX3CR1BIIPMP65E05 KVQLVESGGGSVQAGESLRLSCAASGSIFSSNAMAWYRQAPGKQRDLVAGINSVGITKYADSVKGRFTISRDNAKNTVYLQMNSLKPEDTAVYYCSDPRRGWDTRYWGQGTLVTVSS SEQ ID NO: 32

CX3CR1BIIPMP65B11 EVQLVKSGGGSVQAGESLRLSCAASGSIFSSNAMAWYRQAPGKQRDLVAVINKVGITKYADSVKGRFTISRDNAKNTVYLQMNSLKPEDTAVYYCSDPRRGWDTRYWGQGTLVTVSS SEQ ID NO: 33

CX3CR1BIIPMP65B07 EVQLVESGGGSVQAGESLRLSCAASGSIFSSNAMAWYRQAPGKQRDLVAAINSVGITKYADSVKGRFTISRDNAKNTVYLQMNSLKPEDTAVYYCSDPRRGWDTRYWGQGTLVTVSS SEQ ID NO: 34

CX3CR1BIIPMP65B09 EVQLVESGGGSVQAGESLRLSCAASGSIFSRNAMAWYRQAPGKQRDLVASINSVGITKYGDSVKGRFTISRDNAKNTVYLQMNSLKPEDTAVYYCSDARRGWDTRYWGQGTLVTVSS SEQ ID NO: 35

CX3CR1BIIPMP65H01 EVQLVESGGGSVQAGESLRLSCAASGGIFSRNAMAWYRQAPGKQRDLVASINSVGITKYGDSVKGRFTISRDNAKNTVYLQMNSLKPEDTAVYYCSDARRGWDTRYWGQGTQVTVSS SEQ ID NO: 36

CX3CR1BIIPMP65G07 EVQLVESGGGSVQAGESLRLSCAASGTIFSSNAMAWYRQAPGKQRDLVAGINSVDITRYADSVKGRFTISRDNAKNTVYLQMNSLKPEDTAVYYCSDPRRGWNTRYWGQGTQVTVSS SEQ ID NO: 37

CX3CR1BIIPMP66H08 EVQLVESGGGSVQAGESLRLSCAASGSIFSSNAMAWYRQAPGKQRDLVALINSVGITKYADSVKGRFTISRDNAKNTVYLQMNSLKPEDTAVYYCSDPRRGWDTRYWGQGTQVTVSS SEQ ID NO: 38

CX3CR1BIIPMP66H04 EVQLVESGGGSVQAGGSLRLSCAASGSIFSSNAMAWYRQAPGKQRDLVAAINSVGITKYADSVKGRFTISRDNAKNTVYLQMMSLKPEDTAVYYCSDPRRGWDTRYWGQGTLVTVSS SEQ ID NO: 39

TABLE 5-continued

VHH domains
SEQ ID NO: 1-48 are VHH domains of family 101. SEQ ID NO: 49-52 are VHH domains of family 9. SEQ ID NO: 53-120 are VHH domains of family 13.

| | | |
|---|---|---|
| CX3CR1BIIPMP66F02 | EVQLVESGGGSVQAGESLRLSCAASGSIFSSNAMAWYRQAPGKQRDLVALINSVGITKYAGSVKGRFTISRDNAKNTVYLQMNSLKPEDTAVYYCTSDPRRGWDTRYWGQGTQVTVSS | SEQ ID NO: 40 |
| CX3CR1BIIPMP66E11 | EVQLVESGGGSVQAGESLRLSCAASGSIFSSNAMAWYRQAPGKQRDLVAAINSVGTTKYADSVKGRFTISRDNAKNTVYLQMNSLKPEDTAVYYCTSDPRRGWDTRYWGQGTQVTVSS | SEQ ID NO: 41 |
| CX3CR1BIIPMP66D10 | EVQLVESGGGSVQAGESLRLSCAASGSIFSSNAMAWYRQALGKQRDLVALINSVGITKYADSVKGRFTISRDNAKNTVYLQMNSLKPEDTAVYYCTSDPRRGWDTRYWGQGTQVTVSS | SEQ ID NO: 42 |
| CX3CR1BIIPMP66D08 | EVQLMESGGGSVQAGESLRLSCAASGSIFSSNAMAWYRQAPGKQRDLVAGINSVGITKYADSVKGRFTISRDNAKNTVYLQMNSLKPEDTAVYYCTSDPRRGWDTRYWGQGTQVTVSS | SEQ ID NO: 43 |
| CX3CR1BIIPMP66A04 | EVQLVESGGGSVQAGESLRLSCAASGSIFSSNAMAWYRQALGKQRDLVALINSVGITKYADSVKGRFTISRDNAKNTVYLQMNSLKPEDTAVYYCTSDPRRGWDTRYWGQGTLVTVSS | SEQ ID NO: 44 |
| CX3CR1BIIPMP66D04 | KVQLVESGGGSVQAGESLRLSCAASGTIFSSNAMAWYRQAPGKQRDLVAGINSVDITKYADSVKGRFTISRDNAKNTVYLQMNSLKPEDTAVYYCTSDPRRGWNTRYWGQGTLVTVSS | SEQ ID NO: 45 |
| CX3CR1BIIPMP66D02 | EVQLVESGGGSVQAGESLRLSCAASGSIFSSNAMAWYRQAPGKQRDLVAVINSVGITKYADSVKGRFTTSGDNAKNTVYLQMNSLKPEDTAVYYCTSDARRGWDTRYWGQGTQVTVSS | SEQ ID NO: 46 |
| CX3CR1BIIPMP66D06 | EVQLVESGGGSVQAGESLRLSCAASGSIFSSNAMAWYRQAPGKQRDLVASIDSVGITKYRDSVKGRFTISRDNAKNTVYLQMNSLKPEDTAVYYCTSDARRGWDTRYWGQGTQVTVSS | SEQ ID NO: 47 |
| CX3CR1BIIPMP66G01 | EMQLVESGGGSVQAGESLRLSCAASGSIFSSNAMAWYRQAPGKQRDLVALINSVGITKYADSVKGRFTISRDNAKNTVYLQMNSLKPEDTAVYYCTSDGRRGWDTRYWGQGTQVTVSS | SEQ ID NO: 48 |
| CX3CR1BIIPMP11H11 | EVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTQVTVSS | SEQ ID NO: 49 |
| CX3CR1BIIPMP12B6 | EVQLVQSGGGLVQAGGSLRLSCVASGRTFSSYAMGWFRQAPGRERAFVAGISGSASRKYYADSVKGRFTVSRDNARNTVYLQMNSLKPEDTAVYYCAASNSYPKVQFDYYGQGTQVTVSS | SEQ ID NO: 50 |
| CX3CR1BIIPMP12G9 | EVQLVESGGGLVQPGGSLRLSCVASGRTFSSYAMGWFRQAPGKEREFVAGISGSGSRKYYADSVKGRFTISRDNARNTVYLQMNSLKPEDRAVYYCAASNSYPKVQFDYYGQGTQVTVSS | SEQ ID NO: 51 |
| CX3CR1BIIPMP15G11 | EVQLVESGGGLVQAGGSLRLSCVASGRTFSSYAMGWFRQAPGKEREFVAGISGSGSRKYYADSVKGRFTISRDNARNTVYLQMNSLKPEDRAVYYCAASNSYPKVQFDYYGQGTQVTVSS | SEQ ID NO: 52 |
| CX3CR1BIIPMP18E6 | KVQLVESGGGLVQPGGSLRLSCATSGTIFSNNAMGWYRQAPGKKRDLVASISSSGSTNYADSVKGRFTVSRDNDKNTGYLQMNSLKPEDTGVYYCTLDARRGWNTAYWGQGAQVTVSS | SEQ ID NO: 53 |
| CX3CR1BIIPMP12C2 | EVQLVESGGGLVQPGGSLRLSCATSGTIFSNTAMGWYRQAPGKKRDLVASISNSGSTNYADSVKGRFTVSRDNDKNTGYLQMNSLKPEDTGVYYCTVDARRGWNSGYWGQGTQVTVSS | SEQ ID NO: 54 |
| CX3CR1BIIPMP18A10 | EVQLVESGGGLVQPGGSLRLSCATSGIIFSNNAMGWYRQAPGKKRDLVASISNSGSTNYADSAKGRFTVSRDNDKNTGYLQMNSLKPEDTGVYYCTVDARRGWNTAYWGQGTQVTVSS | SEQ ID NO: 55 |
| CX3CR1BIIPMP18A2 | EVQLVESGGGVVQPGGSLRLSCVTSGIIFSNNAMGWYRQGPGKKRDLVASIGSTYSTNYADSVKGRFTVSRDNDKNTGYLQMNSLKPEDTGVYYCTIDARRGWNTAYWGQGTPVTVSS | SEQ ID NO: 56 |
| CX3CR1BIIPMP18A8 | EVQLVESGGGLVQPGGSLRLSCATSRTIFRSNAMGWYRQAPGKKRDLVASISNSGSTNYADSVKGRFTVSRDNDKNTGYLQMNSLKPEDTGVYYCTIDARRGWNTGYWGQGTQVTVSS | SEQ ID NO: 57 |
| CX3CR1BIIPMP18A9 | EVQLVESGGGVVQPGGSLRLSCVTSGIIFSNNAMGWYRQGPGKKRDLVASISSTYSTNYADSVKGRFTVSRDNDKNTGYLQMNSLKPEDTGVYYCTIDARRGWNTAYWGQGTPVTVSS | SEQ ID NO: 58 |
| CX3CR1BIIPMP18B7 | EVQLVESGGGLVQPGGSLRLSCATSGTIFRSNAMGWYRQAPGKKRDLVASISNSGSTNYADSVKGRFTVSRDNDKNTGYLQMNSLKPEDTGVYYCTVDARRGWNSGYWGQGTQVTVSS | SEQ ID NO: 59 |
| CX3CR1BIIPMP18B9 | EVQLVESRGGLVQPGGSLRLSCATSGTIFSNNAMGWYRQAPGKKRDLVASISSSGSTNYADSVKGRFTVSRDNDKNTGYLQMNSLKPEDTGVYYCTLDARRGWNTAYWGQGTQVTVSS | SEQ ID NO: 60 |
| CX3CR1BIIPMP18C6 | EVQLMESGGGLVQPGGSLRLSCATSGTIFSNNAMGWYRQAPGKKRDLVASISNSGSTNYADSVKGRFTVSRDNDKNTGYLQMNSLKPEDTGVYYCTVDARRGWNTAYWGQGTQVTVSS | SEQ ID NO: 61 |
| CX3CR1BIIPMP18C9 | EVQLVESGGGLVQPGGSLRLSCATSGIIFSNNAMGWYRQAPGKKRDLVASISNSGSTNYADSVKGRFTVSRDNDKNTGYLQMNSLKPEDTGVYYCTVDARRGWNTAYWGQGTQVTVSS | SEQ ID NO: 62 |
| CX3CR1BIIPMP18D1 | EVQLVESGGGLVQPGGSLRLSCATSGIIFSNNAMGWYRQAPGKKRDLVASISNSGSTNYADSVKGRFTVSRDNDKSTGYLQMNSLKPEDTGVYYCTVDARRGWNTAYWGQGTQVTVSS | SEQ ID NO: 63 |
| CX3CR1BIIPMP18D10 | EVQLVESGGGLVQPGGSLGLSCATSGTIFSNNAMGWYRQAPGKKRDLVASISNSGSTNYADSVKGRFTVSRDNDKNTGYLQMNSLKPEDTGVYYCTVDARRGWNTAYWGQGTQVTVSS | SEQ ID NO: 64 |
| CX3CR1BIIPMP18D12 | EVQLVESGGGLVQPGGSLRLSCTTSGTIFSNNAMGWYRQAPGKKRDLVASISNSGSTNYADSVKGRFTVSRDNDKNTGYLQMNNLKPEDTGVYYCTLDARRGWNTAYWGQGTQVTVSS | SEQ ID NO: 65 |
| CX3CR1BIIPMP18F1 | KVQLVESGGGLVQPGGSLRLSCATSGTIFSNNAMGWYRQAPGKKRDLVASISNSGSTNYADSVKGRFTVSRDNDKNTGYLQMNSLKPEDTGVYYCTVDARRGWNTAYWGQGTQVTVSS | SEQ ID NO: 66 |
| CX3CR1BIIPMP18F5 | EVQLVESGGGLVQPGGSLRLSCATSGTIFSNNAMGWYRQAPGKKRDLVASISNSGSTNYADSVKGRFTVSRDNDKNTGYLQMNSLKPEDTGVYYCTVDARRGWNTAYWGQGTQVTVSS | SEQ ID NO: 67 |

TABLE 5-continued

VHH domains
SEQ ID NO: 1-48 are VHH domains of family 101. SEQ ID NO: 49-52 are VHH domains of family 9. SEQ ID NO: 53-120 are VHH domains of family 13.

CX3CR1BI EVQLVDSGGGLVQPGGSLRLSCATSGTIFSNNA SEQ ID 68
IPMP18F6 MGWYRQAPGKKRDLVASISNSGSTNYADSVK NO:
GRFTVSRDNDKNTGYLQMNSLKPEDTGVYYC
TVDARRGWNTAYWGQGTQVTSS

CX3CR1BI EVQLVESGGGLVQPGGSLRLSCATSGTIFRTNA SEQ ID 69
IPMP18F9 MGWYRQAPGKKRDLVASISNSGSTNYADSVK NO:
GRFTVSRDNDKNTAYLQMNSLKPEDTGVYYC
TIDGRRGWNTGYWGQGTQVTSS

CX3CR1BI EVQLVESGGGLVQPGGSLRLSCATSRTIFRSNA SEQ ID 70
IPMP18G5 MGWYRQAPGKKRDLVASISNSGSTNYADSVK NO:
GRFTVSRDNDKNTGYLQMNSLKPEDTGVYYC
TVDARRGWNTGYWGQGTQVTSS

CX3CR1BI EVQLVESGGGLVQPGGSLRLSCATSGTIFSNNA SEQ ID 71
IPMP18H1 MGWYRQALGKKRDLVASISNSGSTNYADSVK NO:
GRFTVSRDNDKNTGYLQMNSLKPEDTGVYYC
TVDARRGWNTAYWGQGTQVTSS

CX3CR1BI EVQLVESGGGLVQPGGSLRLSCATSKTIFRSNA SEQ ID 72
IPMP18H1 MGWYRQAPGKKRDLVASISNSGSTNYADSVK NO:
0 GRFTVSRDNDKNTGYLQMNSLKPEDTGVYYC
TVDARRGWNTGYWGQGTQVTSS

CX3CR1BI EVQLVESRGGLVQPGGSLRLSCATSGIIFSNNA SEQ ID 73
IPMP18H7 MGWYRQAPGKKRDLVASISNSGSTNYADSVK NO:
GRFTVSRDNDKNTGYLQMNSLKPEDTGVYYC
TVDARRGWNTGYWGQGTQVTSS

CX3CR1BI EVQLVKSGGGLVQPGGSLRLSCTTSGTIFSNNA SEQ ID 74
IPMP18H9 MGWYRQAPGKKRDLVASISNSGSTNYADSVK NO:
GRFTVSRDNDKNTGYLQMNNLKPEDTGVYYC
TLDARRGWNTAYWGQGTQVTSS

CX3CR1BI EVQLVESGGGLVQAGGSLRLSCVTSGIIFSNNA SEQ ID 75
IPMP20B3 MGWYRQGPGKKRDLVASIGSTYSTNYADSVK NO:
GRFTVSRDNDKNTGYLQMNSLKPEDTGVYYC
TIDARRGWNTAYWGQGTPVTSS

CX3CR1BI EVQLVESGGGLVQPGGSLRLSCATSGTIFRSNA SEQ ID 76
IPMP20C1 MGWYRQAPGKKRDLVASISNSGSTNYADSVK NO:
2 GRFTVSRDNDKNTGYLQMNSLKPEDTGVYYC
TVDARRGWNSGYWGQGTRVTSS

CX3CR1BI KVQLVESGGGLVQPGGSLRLSCATSGIIFSNNA SEQ ID 77
IPMP20C3 MGWYRQAPGKKRDLVASISNSGSTNYADSVK NO:
GRFTVSRDNDKNTGYLQMNSLKPEDTGVYYC
TVDARRGWNTAYWGQGTQVTSS

CX3CR1BI EVQLVESGGGLVQAGGSLRLSCATSGTIFSNNA SEQ ID 78
IPMP20C6 MGWYRQAPGKKRDLVASISNSGSTNYADSVK NO:
GRFTVSRDNDKNTGYLQMNSLKPEDTGVYYC
TVDARRGWNTAYWGQGTQVTSS

CX3CR1BI EVQLVESGGGLVQPGRSLRLSCATSGTTFRSNA SEQ ID 79
IPMP20D8 MGWYRQGPGKKRDLVASITNSGSTNYADSVK NO:
GRFTVSRDNDKNTGYLQMSSLKPEDTGVYYCT
LDARRGWNTGYWGQGTQVTSS

CX3CR1BI EVQLVESGGGLVQPGGSLRLSCATSRTIFRSNA SEQ ID 80
IPMP20E1 MGWYRQGPGKKRDLVASITNSGSTNYADSVK NO:
1 GRFTVSRDNDRNTGYLQMNSLKPEDTGVYYC
TVDARRGWNTGYWGQGTQVTSS

CX3CR1BI KVQLVESGGGLVQPGGSLRLSCATSGTIFSNNA SEQ ID 81
IPMP20E5 MGWYRQVPGKKRDLVASISNSGSTNYADSVK NO:
GRFTVSRDNDKNTGYLQMNSLKPEDTGVYYC
TVDARRGWNTGYWGQGTQVTSS

CX3CR1BI EVQLVESGGGLVQPGGSLRLSCATSGTIFSNNA SEQ ID 82
IPMP20F3 MGWYRQAPGKKRDLVASISSSGSTNYADSVK NO:
GRFTVSRDNDKNTGYLQMNSLKPEDTGVYYC
TLDARRGWNTAYWGQGTQVTSS

CX3CR1BI EVQLVESGGGLVQPGGSLRLSCATSATIFRSNA SEQ ID 83
IPMP20F4 MGWYRQAPGKKRDLVASISNSGSTNYADSVK NO:
GRFTVSRDNDKNTAYLQMNSLKPEDTGVYYC
TIDGRRGWNTGYWGQGTQVTSS

CX3CR1BI EVQLVESGGGLVQPGGSLRLSCATSATIFRSNA SEQ ID 84
IPMP20F5 MGWYRQAPGKKRDLVASISNSGSTNYADSVK NO:
GRSTVSRDNDKNTAYLQMNSLKPEDTGVYYC
TIDGRRGWNTGYWGQGTQVTSS

CX3CR1BI EVQLVESGGGLVQPGGSLRLSCATSGTIFSNNA SEQ ID 85
IPMP21B6 MGWYRQAPGKKRDLVASISNSGSTNYADSVK NO:
GRFTVSRDNDKNTGYLQMNSLKPEDMGVYYC
TVDARRGWNTAYWGQGTQVTSS

CX3CR1BI EVQLVESGGGLVQPGGSLRLSCATSGIIFSNNA SEQ ID 86
IPMP24A1 MGWYRQAPGKKRDLVASISNSGSANYADSVK NO:
2 GRFTVSRDNDKNTGYLQMNSLKPEDTGVYYC
TVDARRGWNTAYWGQGTQVTSS

CX3CR1BI EVQLVESGGGLVQPGGSLRLSCTTSGTIFSNNA SEQ ID 87
IPMP24A6 MGWYRQAPGKKRDLVASISNSGSTNYADSVK NO:
GRFTVSGDNDKNTGYLQMNNLKPEDTGVYYC
TLDARRGWNTAYWGQGTQVTSS

CX3CR1BI EVQLVESGGGLVQPGGSLRLSCATSGTIFRSNA SEQ ID 88
IPMP24B9 MGWYRQAPGKKRDLVASISISGSTNYADSVKG NO:
RFTVSRDNDKNTGYLQMNSLKPEDTGVYYCT
VDARRGWNTGFWGQGTQVTSS

CX3CR1BI EVQLVESGGGLVQPGGSLRLSCVTSGIIFSNNA SEQ ID 89
IPMP24D3 MGWYRQGPGKKRDLVASISSTYSTNYADSVK NO:
GRFTVSRDNDKNTGYLQMNSLKPEDTGVYYC
TIDARRGWNTAYWGQGTPVTSS

CX3CR1BI EVQLMESGGGMVQVGGSLRLSCTASGLIFSNN SEQ ID 90
IPMP24F7 AMGWYRQGPGKKRDLVASISSTYSTNYADSV NO:
KGRFTVSRDNDKNTGYLQMNSLKPEDTGVYY
CTIDARRGWNTAYWGQGTPVTSS

CX3CR1BI EVQLVESGGGLVQPGGSLRLSCAISATIFRSNA SEQ ID 91
IPMP28B4 MGWYRQAPGKKRDLVASISNSGSTNYADSVK NO:
GRFTVSRDNDKNTAYLQMNSLKPEDTGVYYC
TIDGRRGWNTGYWGQGTQVTSS

CX3CR1BI EMQLVESGGGVVQPGGSLRLSCVTSGIIFSNNA SEQ ID 92
IPMP28F1 MGWYRQGPGKKRDLVASIGSTYSTNYADSVK NO:
GRFTVSRDNDKNTGYLQMNSLKPEDTGVYYC
TIDARRGWNTAYWGQGTPVTSS

CX3CR1BI EVQLVESGGGLVQPGGSLRLSCATSGIIFSNNA SEQ ID 93
IPMP28F6 MGWYRQAPGKKRDLVASISNSGSTNHADSVK NO:
GRFTVSRDNDKNTGYLQMNSLKPEDTGVYYC
TVDARRGWNTAYWGQGTQVTSS

CX3CR1BI EVQLVESGGGLVQPGGSLRLSCATSGTIFSNNA SEQ ID 94
IPMP28F9 MGWYRQVPGKKRDLVASISNSGSTNYADSVK NO:
GRFTVSRDNDKNTGYLQMNSLKPEDTGVYYC
TVDARRGWNTGYWGQGTQVTSS

CX3CR1BI EVQLVESRGGLVQPGGSLRLSCATSGTIFSNNA SEQ ID 95
IPMP29A5 MGWYRQAPGKKRDLVASISNSGSTNYADSVK NO:
GRFTVSRDNDKNTGYLQMNSLKPEDTGVYYC
TVDARRGWNTAYWGQGTQVTSS

TABLE 5-continued

VHH domains
SEQ ID NO: 1-48 are VHH domains of family 101. SEQ ID NO: 49-52 are VHH domains of family 9. SEQ ID NO: 53-120 are VHH domains of family 13.

CX3CR1BI KVQLVESGGGLVQPGGSLRLSCATSGTIFRSNA SEQ ID NO: 96
IPMP29D5 MGWYRQAPGKKRDLVASISNSGSTNYADSVK
GRFTVSRDNDKNTGYLQMNSLKPEDTGVYYC
TVDARRGWNSGYWGQGTQVTVSS

CX3CR1BI EVQLVESEGGGLVQPGGSLRLPCATSKTIFRSNA SEQ ID NO: 97
IPMP29E3 MGWYRQAPGKKRDLVASISNSGSTNYADSVK
GRFTVSRDNDKNTGYLQMNSLKPEDTGVYYC
TVDARRGWNTGYWGQGTQVTVSS

CX3CR1BI EVQLVESGGGLVQPGGSLRLSCATSKTIFRSNA SEQ ID NO: 98
IPMP29E7 MGWYRQAPGKKRGLVASISNSGSTNYADSVK
GRFTVSRDNDKNTGYLQMNSLKPEDTGVYYC
TVDARRGWNTGYWGQGTQVTVSS

CX3CR1BI EVQLMESGGGLVQPGGSLRLSCATSGTIFRSNA SEQ ID NO: 99
IPMP29G1 MGWYRQGPGKKRDLVASITNSGSTNYADSVK
GRFTVSRDNDKNTGYLQMSSLKPEDTGVYYCT
LDARRGWNTGYWGQGTQVTVSS

CX3CR1BI EVQLVESGGGLVQPGGSLRLSCATSGIIFSNNA SEQ ID NO: 100
IPMP29G7 MGWYRQGPGKKRDLVASITNTGSTNYADSVK
GRFTVSRDNDRNTVYLQMNSLKPEDTGVYYC
TVDARRGWNTAYWGQGTQVTVSS

CX3CR1BI EVQLVESGGGLVQAGGSLRLSCTTSGTIFSNNA SEQ ID NO: 101
IPMP29H1 MGWYRQAPGKKRDLVASISNSGSTNYADSVK
GRFTVSRDNDKNTGYLQMNNLKPEDTGVYYC
TLDARRGWNTAYWGQGTQVTVSS

CX3CR1BI EVQLVESGGGLVQPGGSLRLSCATSRTIFRSNA SEQ ID NO: 102
IPMP37A8 MGWYRQAPGKKRDLVASISNSGSTNYADSAK
GRFTVSRDNDKNTGYLQMNSLKPEDTGVYYC
TVDARRGWNTGYWGQGTQVTVSS

CX3CR1BI EVQLVESGGGLVQPGGSLRLSCATSGTIFSNNAM SEQ ID NO: 103
IPMP37B9 GWYRQAPGKKRDLVASISNSGSTNYADSVKGR
FTVSRDNDKNTGYLQMNSLKPEDTGVYYCTV
DARRGWNTAYWGQGTQVTVSS

CX3CR1BI EVQLVESGGGLVQAGGSLRLSCVASGSIFRSNA SEQ ID NO: 104
IPMP37C1 MGWYRQAPGKKRDLVASISNSGSTNYADSVK
2 GRFTVSRDNDKNTGYLQMNSLKPEDTGVYYC
TIDARRGWNTGYWGQGTQVTVSS

CX3CR1BI EVQLVESGGGLVQPGGSLRLSCATSRTIFSNNA SEQ ID NO: 105
IPMP37C7 MGWYRQAPGKKRDLVASISNSGSTNYADSVK
GRFTVSRDNDKNTGYLQMNSLKPEDTGVYYC
TVDARRGWNTAYWGQGTQVTVSS

CX3CR1BI EVQLVESGGGLVQPGGSLRLSCATSGTVFSNN SEQ ID NO: 106
IPMP37D9 AMGWYRQAPGKKRDLVASISSSGSTNYADSV
KGRFTVSRDNDKNTGYLQMNSLKPEDTGVYY
CTLDARRGWNTAYWGQGTQVTVSS

CX3CR1BI EVQLVESGGGLVQPGGSLRLSCATSKPIFRSNA SEQ ID NO: 107
IPMP37E1 MGWYRQAPGKKRDLVASISNSGSTNYADSVK
2 GRFTVSRDNDKNTGYLQMNSLKPEDTGVYYC
TVDARRGWNTGYWGQGTQVTVSS

CX3CR1BI EVQLVESEGGLVQPGGSLRLSCTTSGTIFSNNA SEQ ID NO: 108
IPMP41B1 MGWYRQAPGKKRDLVASISNSGSTNYADSVK
0 GRFTVSRDNDKNTGYLQMNNLKPEDTGVYYC
TLDARRGWNTAYWGQGTQVTVSS

CX3CR1BI EVQLVESGGGLVQPGGSLRLSCATSGTIFSNNA SEQ ID NO: 109
IPMP41B1 MGWYRQAPGKKRDLVASISNSGSTNYADSVK
1 GRFTVSRDNDKNTGYLQMNSPKPEDTGVYYC
TVDARRGWNTAYWGQGTQVTVSS

CX3CR1BI EVQLVESEGGVVQPGGSLRLSCVTSGIIFSNNA SEQ ID NO: 110
IPMP41B8 MGWYRQGPGKKRDLVASIGSTYSTNYADSVK
GRFTVSRDNDKNTGYLQMNSLKPEDTGVYYC
TIDARRGWNTAYWGQGTPVTVSS

CX3CR1BI EMQLVESGGGLVQPGGSLRLSCATSRTIFRSNA SEQ ID NO: 111
IPMP41C1 MGWYRQAPGKKRDLVASISNSGSTNYADSVK
0 GRFTVSRDNDKSTGYLQMNSLKPEDTGVYYCT
VDARRGWNTGYWGQGTQVTVSS

CX3CR1BI EVQLVESGGGVVQPGESLRLSCVTSGIIFSNNA SEQ ID NO: 112
IPMP41F9 MGWYRQGPGKKRDLVASIGSTYSTNYADSVK
GRFTVSRDNDKNTGYLQMNSLKPEDTGVYYC
TIDARRGWNTAYWGQGTPVTVSS

CX3CR1BI KVQLVESGGGLVQPGDSLRLSCAASGLTLDDY SEQ ID NO: 113
IPMP41H1 AMGWYRQAPGKKRDLVASISNSGSTNYADSV
0 KGRFTVSRDNDKNTGYLQMNSLKPEDTGVYY
CTIDARRGWNTGYWGQGTQVTVSS

CX3CR1BI KVQLVESGGGLVQPGGSLRLSCATSRTIFRSNA SEQ ID NO: 114
IPMP46B5 MGWYRQAPGKKRDLVASISNSGSTNYADSVK
GRFTVSRDNDKNTGYLQMNSLKPEDTGVYYC
TIDARRGWNTGYWGQGTQVTVSS

CX3CR1BI EVQLVESGGGLVQPGGSLRLSCATSGTIFSNNA SEQ ID NO: 115
IPMP46D3 MGWYRQVPGKKRDLVASISNSGSTNYADSVK
GRFTVSRDNDKNTGYLRMNSLKPEDTGVYYC
TVDARRGWNTGYWGQGTQVTVSS

CX3CR1BI EVQLVESGGGLVQAGGSLRLSCVTSGIIFSNNA SEQ ID NO: 116
IPMP46H5 MGWYRQGPGKKRDLVASISSTYSTNYADSVK
GRFTVSRDNDKNTGYLQMNSLKPEDTGVYYC
TIDARRGWNTAYWGQGTPVTVSS

CX3CR1BI EVQLVESGGGLVQPGGSLRLSCATSKTIFRSNA SEQ ID NO: 117
IPMP48B8 MGWYRQAPGKKRDLVASISNSGSTNYTDSVK
GRFTVSRDNDKNTGYLQMNSLKPEDTGVYYC
TVDARRGWNTGYWGQGTQVTVSS

CX3CR1BI KVQLVESGGGLVQPGGSLRLSCATSRTIFRSNA SEQ ID NO: 118
IPMP48D1 MGWYRQAPGKKRDLVASISNSGSTNYADSVK
1 GRFTVSRDNDKNTGYLQMNSLKPEDTGVYYC
TVDARRGWNTGYWGQGTQVTVSS

CX3CR1BI EVQLVESGGGLVQPGGSLRLSCATSRTIFRSNA SEQ ID NO: 119
IPMP48G8 MGWYRQAPGKKRDLVASISNSGSTNYADSVK
GRFAVSRDNDKNTGYLQMNSLKPEDTGVYYC
TVDARRGWNTGYWGQGTQVTVSS

CX3CR1BI EVQLVESGGGLVQPGGSLRLSCATSGTIFSNNA SEQ ID NO: 120
IPMP48H9 MGWYRQAPGKKRDLVASISNSGSTNYADFVK
GRFTVSRDNDKNTGYLQMNSLKPEDTGVYYC
TVDARRGWNTAYWGQGTQVTVSS

TABLE 6

Optimized VHH domains

CX3CR1BI EVQLVESGGGSVQPGESLRLSCAASGSIFSNNA SEQ ID NO: 121
I043 MAWYRQAPGKRDLVAAINSVGVTKYADSVK
GRFTISRDNSKNTVYLQMNSLRPEDTAVYYCT
SDPRRGWDTRYWGQGTLVTVSS

CX3CR1BI DVQLVESGGGSVQPGESLRLSCAASGSIFSNNA SEQ ID NO: 122
I045 MAWYRQAPGKRDLVAAINSVGVTKYADSVK
GRFTISRDNSKNTVYLQMNSLRPEDTAVYYCT
SDPRRGWDTRYWGQGTLVTVSS

TABLE 6-continued

Optimized VHH domains

| | | |
|---|---|---|
| CX3CR1BI I047 | EVQLVESGGGLVQPGESLRLSCAASGSIFSSNAMAWYRQAPGKRRDLVAAINSVGVTKYADSVKGRFTISRDNSKNTVYLQMNSLRPEDTAVYYCTSDPRRGWDTRYWGQGTLVTVSS | SEQ ID NO: 123 |
| CX3CR1BI I048 | EVQLVESGGGSVQPGGSLRLSCAASGSIFSSNAMAWYRQAPGKRRDLVAAINSVGVTKYADSVKGRFTISRDNSKNTVYLQMNSLRPEDTAVYYCTSDPRRGWDTRYWGQGTLVTVSS | SEQ ID NO: 124 |
| CX3CR1BI I049 | EVQLVESGGGSVQPGESLRLSCAASGSIFSSNAMAWYRQAPGKQRDLVAAINSVGVTKYADSVKGRFTISRDNSKNTVYLQMNSLRPEDTAVYYCTSDPRRGWDTRYWGQGTLVTVSS | SEQ ID NO: 125 |
| CX3CR1BI I050 | EVQLVESGGGSVQPGESLRLSCAASGSIFSSNAMAWYRQAPGKRRELVAAINSVGVTKYADSVKGRFTISRDNSKNTVYLQMNSLRPEDTAVYYCTSDPRRGWDTRYWGQGTLVTVSS | SEQ ID NO: 126 |
| CX3CR1BI I061 | EVQLVESGGGLVQPGGSLRLSCAASGSIFSSNAMAWYRQAPGKRRDLVAAINSVGVTKYADSVKGRFTISRDNSKNTVYLQMNSLRPEDTAVYYCTSDPRRGWDTRYWGQGTLVTVSS | SEQ ID NO: 127 |
| CX3CR1BI I056 | EVQLVESGGGLVQPGGSLRLSCAASGSIFSSNAMAWYRQAPGKQRDLVAAINSVGVTKYADSVKGRFTISRDNSKNTVYLQMNSLRPEDTAVYYCTSDPRRGWDTRYWGQGTLVTVSS | SEQ ID NO: 128 |
| CX3CR1BI I057 | EVQLVESGGGLVQPGGSLRLSCAASGSIFSSNAMAWYRQAPGKRRELVAAINSVGVTKYADSVKGRFTISRDNSKNTVYLQMNSLRPEDTAVYYCTSDPRRGWDTRYWGQGTLVTVSS | SEQ ID NO: 129 |
| CX3CR1BI I060 | EVQLVESGGGLVQPGGSLRLSCAASGSIFSSNAMAWYRQAPGKQRELVAAINSVGVTKYADSVKGRFTISRDNSKNTVYLQMNSLRPEDTAVYYCTSDPRRGWDTRYWGQGTLVTVSS | SEQ ID NO: 130 |
| CX3CR1BI I065 | EVQLVESGGGSVQAGESLRLSCAASGSIFSSNAMAWYRQAPGKRRDLVAAISSVGVTKYADSVKGRFTISRDNAKNTVYLQMNSLKPEDTAVYYCTSDPRRGWDTRYWGQGTLVTVSS | SEQ ID NO: 131 |
| CX3CR1BI I067 | EVQLVESGGGSVQAGESLRLSCAASGSIFSSNAMAWYRQAPGKRRDLVAAIQSVGVTKYADSVKGRFTISRDNAKNTVYLQMNSLKPEDTAVYYCTSDPRRGWDTRYWGQGTLVTVSS | SEQ ID NO: 132 |
| CX3CR1BI I068 | EVQLVESGGGSVQAGESLRLSCAASGSIFSSNAMAWYRQAPGKRRDLVAAIGSVGVTKYADSVKGRFTISRDNAKNTVYLQMNSLKPEDTAVYYCTSDPRRGWDTRYWGQGTLVTVSS | SEQ ID NO: 133 |
| CX3CR1BI I074 | EVQLVESGGGSVQAGESLRLSCAASGSIFSSNAMAWYRQAPGKRRDLVAAITSVGVTKYADSVKGRFTISRDNAKNTVYLQMNSLKPEDTAVYYCTSDPRRGWDTRYWGQGTLVTVSS | SEQ ID NO: 134 |
| CX3CR1BI I118 | EVQLVESGGGSVQAGESLRLSCAASGSIFSSNAMAWYRQAPGKRRDLVAAINTVGVTKYADSVKGRFTISRDNAKNTVYLQMNSLKPEDTAVYYCTSDPRRGWDTRYWGQGTLVTVSS | SEQ ID NO: 135 |
| CX3CR1BI I129 | EVQLVESGGGSVQAGESLRLSCAASGSIFSSNAMAWYRQAPGKRRDLVAAINGVGVTKYADSVKGRFTISRDNAKNTVYLQMNSLKPEDTAVYYCTSDPRRGWDTRYWGQGTLVTVSS | SEQ ID NO: 136 |
| CX3CR1BI I158 | EVQLVESGGGSVQAGESLRLSCAASGSIFSSNAMAWYRQAPGKRRDLVAAINPVGVTKYADSVKGRFTISRDNAKNTVYLQMNSLKPEDTAVYYCTSDPRRGWDTRYWGQGTLVTVSS | SEQ ID NO: 137 |
| CX3CR1BI I306 | DVQLVESGGGLVQPGGSLRLSCAASGSIFSSTAMAWYRQAPGKRRDLVAAISSVGVTKYADSVKGRFTISRDNSKNTVYLQMNSLRPEDTAVYYCTSDPRRGWDTRYWGQGTLVTVSS | SEQ ID NO: 138 |
| CX3CR1BI I307 | DVQLVESGGGLVQPGGSLRLSCAASGSIFSSTAMAWYRQAPGKRRDLVAAISTVGVTKYADSVKGRFTISRDNSKNTVYLQMNSLRPEDTAVYYCTSDPRRGWDTRYWGQGTLVTVSS | SEQ ID NO: 139 |
| CX3CR1BI I308 | DVQLVESGGGLVQPGGSLRLSCAASGSIFSSNAMAWYRQAPGKRRDLVAAINSVGVTKYADSVKGRFTISRDNSKNTVYLQMNSLRPEDTAVYYCTSDPRRGWDTRYWGQGTLVTVSS | SEQ ID NO: 140 |
| CX3CR1BI I00306 (D1E) | EVQLVESGGGLVQPGGSLRLSCAASGSIFSSTAMAWYRQAPGKRRDLVAAISSVGVTKYADSVKGRFTISRDNSKNTVYLQMNSLRPEDTAVYYCTSDPRRGWDTRYWGQGTLVTVSS | SEQ ID NO: 197 |
| CX3CR1BI I00307 (D1E) | EVQLVESGGGLVQPGGSLRLSCAASGSIFSSTAMAWYRQAPGKRRDLVAAISTVGVTKYADSVKGRFTISRDNSKNTVYLQMNSLRPEDTAVYYCTSDPRRGWDTRYWGQGTLVTVSS | SEQ ID NO: 198 |
| CX3CR1BI I00308 (D1E) | EVQLVESGGGLVQPGGSLRLSCAASGSIFSSNAMAWYRQAPGKRRDLVAAINSVGVTKYADSVKGRFTISRDNSKNTVYLQMNSLRPEDTAVYYCTSDPRRGWDTRYWGQGTLVTVSS | SEQ ID NO: 199 |
| CX3CR1BI I00307A | DVQLVESGGGLVQPGGSLRLSCAASGSIFSSTAMAWYRQAPGKRRDLVAAISTVGVTKYADSVKGRFTISRDNSKNTVYLQMNSLRPEDTAVYYCTSDPRRGWDTRYWGQGTLVTVSSA | SEQ ID NO: 200 |
| CX3CR1BI I00307K | DVQLVESGGGLVQPGGSLRLSCAASGSIFSSTAMAWYRQAPGKRRDLVAAISTVGVTKYADSVKGRFTISRDNSKNTVYLQMNSLRPEDTAVYYCTSDPRRGWDTRYWGQGTLVTVSSK | SEQ ID NO: 201 |
| CX3CR1BI I00307AK | DVQLVESGGGLVQPGGSLRLSCAASGSIFSSTAMAWYRQAPGKRRDLVAAISTVGVTKYADSVKGRFTISRDNSKNTVYLQMNSLRPEDTAVYYCTSDPRRGWDTRYWGQGTLVTVSSAK | SEQ ID NO: 202 |

Representative sequences of CX3CR1-binding bivalent VHH domains that may comprise the CX3CR1-targeting polypeptide portion of the imaging agents described herein are shown in Tables 7 below. As seen in the sequences, the two VHH domains are joined by a Gly/Ser linker:

TABLE 7

CX3CR1-binding bivalent VHH domains

| | | |
|---|---|---|
| CX3CR1BII007 | EVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTQVTVSSGGGGSGGGGSGGGGSGGGGSGGGGSGGGGSGGGGSKVQLVESGGGLVQPGGSLRLSCATSGTIFSNNAMGWYRQAPGKKRDLVASISSSGSTNYADSVKGRFTVSRDNDKNTGYLQMNSLKPEDTGVYYCTLDARRGWNTAYWGQGAQVTVSS | SEQ ID NO: 203 |
| CX3CR1BII009 | KVQLVESGGGLVQPGGSLRLSCATSGTIFSNNAMGWYRQAPGKKRDLVASISSSGSTNYADSVKGRFTVSRDNDKNTGYLQMNSLKPEDTGVYYCTLDARRGWNTAYWGQGAQVTVSSGGGGSGGGGSGGGGSGGGGSGGGGSGGGGSGGEVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTQVTVSS | SEQ ID NO: 204 |

TABLE 7-continued

CX3CR1-binding bivalent VHH domains

| Name | Sequence | SEQ ID NO: |
|---|---|---|
| CX3CR1BII012 | EVQLVESGGGSVQAGGSLRLSCAASGSIFSSNAMAWYRQAPGKQRDLVAGINSVGITKYADSVKGRFTISRDNAKNTVYLQMNSLKPEDTAVYYCTSDPRRGWDTRYWGQGTLVTVSSGGGGSGGGGSGGGGSGGGGSGGGGSGGGGSKVQLVESGGGLVQPGGSLRLSCATSGTIFSNNAMGWYRQAPGKKRDLVASISSSGSTNYADSVKGRFTVSRDNDKNTGYLQMNSLKPEDTGVYYCTLDARRGWNTAYWGQGAQVTVSS | 205 |
| CX3CR1BII016 | EVQLVESGGGSVQAGESLRLSCAASGSIFSSNAMAWYRQAPGKQRDLVAVINSVGITKYADSVKGRFTISGDNAKNTVYLQMNSLKPEDTAVYYCTSDARRGWDTRYWGQGTQVTVSSGGGGSGGGGSGGGGSGGGGSGGGGSGGGGSEVQLVESGGGSVQAGESLRLSCAASGSIFSSNAMAWYRQAPGKQRDLVAVINSVGITKYADSVKGRFTISGDNAKNTVYLQMNSLKPEDTAVYYCTSDARRGWDTRYWGQGTQVTVSS | 206 |
| CX3CR1BII017 | EVQLVESGGGSVQAGESLRLSCAASGSIFSSNAMAWYRQAPPGKQRDLVALINSVGITKYADSVKGRFTISSDNAKNTVYLEMNSLKPEDTAVYYCTSDGRRGWDTRYWGQGTQVTVSSGGGGSGGGGSGGGGSGGGGSGGGGSGGGGSEVQLVESGGGSVQAGESLRLSCAASGSIFSSNAMAWYRQAPGKQRDLVALINSVGITKYADSVKGRFTISSDNAKNTVYLEMNSLKPEDTAVYYCTSDGRRGWDTRYWGQGTQVTVSS | 207 |
| CX3CR1BII018 | EVQLVESGGGSVQAGESLRLSCAASGSIFSSNAMAWYRQAPGKRRDLVAAINSVGVTKYADSVKGRFTISRDNAKNTVYLQMNSLKPEDTAVYYCTSDPRRGWDTRYWGQGTQVTVSSGGGGSGGGGSGGGSGGGGSGGGGSGGGGSEVQLVESGGGSVQAGESLRLSCAASGSIFSSNAMAWYRQAPGKRRDLVAAINSVGVTKYADSVKGRFTISRDNAKNTVYLQMNSLKPEDTAVYYCTSDPRRGWDTRYWGQGTQVTVSS | 208 |
| CX3CR1BII019 | EMQLVESGGGSVQAGESLRLSCAASGSIFSSNAMAWYRQAPGKQRDLVALINSVGITKYADSVKGRFTISRDNAKNTVYLQMNSLKPEDTAVYYCTSDGRRGWDTRYWGQGTQVTVSSGGGGSGGGGSGGGSGGGGSGGGGSGGGGSEMQLVESGGGSVQAGESLRLSCAASGSIFSSNAMAWYRQAPGKQRDLVALINSVGITKYADSVKGRFTISRDNAKNTVYLQMNSLKPEDTAVYYCTSDGRRGWDTRYWGQGTQVTVSS | 209 |
| CX3CR1BII020 | EVQLVESGGGSVQAGESLRLSCAASGSIFSSNAMAWYRQAPGKQRDLVAGINSVGITKYADSVKGRFTISRDNAKNTAYLQMNSLKPEDTAVYYCTSDPRRGWDTRYWGQGTLVTVSSGGGGSGGGGSGGGGSGGGGSEVQLVESGGGSVQAGESLRLSCAASGSIFSSNAMAWYRQAPGKQRDLVAGINSVGITKYADSVKGRFTISRDNAKNTAYLQMNSLKPEDTAVYYCTSDPRRGWDTRYWGQGTLVTVSS | 210 |
| CX3CR1BII026 | EVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTQVTVSSGGGGSGGGGSGGGGSGGGGSGGGGSEVQLVESGGGSVQAGESLRLSCAASGSIFSSNAMAWYRQAPGKRRDLVAAINSVGVTKYADSVKGRFTISRDNAKNTVYLQMNSLKPEDTAVYYCTSDPRRGWDTRYWGQGTQVTVSS | 211 |
| CX3CR1BII027 | EVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTQVTVSSGGGGSGGGGSGGGGSGGGGSGGGGSEVQLVESGGGSVQAGESLRLSCAASGSIFSSNAMAWYRQAPGKQRDLVAGINSVGITKYADSVKGRFTISRDNAKNTAYLQMNSLKPEDTAVYYCTSDPRRGWDTRYWGQGTLVTVSS | 212 |
| CX3CR1BII006 | EVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTLVTVSSGGGGSGGGGSGGGGSGGGGSGGGGSGGGGSEVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTLVTVSS | 222 |
| CX3CR1BII101 | DVQLVESGGGLVQPGGSLRLSCAASGSIFSSTAMAWYRQAPGKKRDLVAAISTVGVTKYADSVKGRFTISRDNSKNTVYLQMNSLRPEDTAVYYCTSDPRRGWDTRYWGQGTLVTVSSGGGGSGGGGSGGGGSGGGGSGGGGSGGGGSEVQLVESGGGLVQPGGSLRLSCAASGSIFSSTAMAWYRQAPGKRRDLVAAISTVGVTKYADSVKGRFTISRDNSKNTVYLQMNSLRPEDTAVYYCTSDPRRGWDTRYWGQGTLVTVSS | 223 |

The VHH domain or bivalent VHH domains that comprise the CX3CR1-targeting portion of the imaging agent may be further modified by methods known in the art in order to enable linking to the detection label as described herein, below. For example, in order enable linking to a $^{99m}$Tc detection label by the tricarbonyl method (described below), a hexahistidine (SEQ ID NO: 230) or myc-hexahistidine tag ("hexahistidine" disclosed as SEQ ID NO: 230) may be added to the C-terminal of the desired VHH domain or bivalent VHH domains. Representative examples of such modified VHH domains, monovalent or bivalent, are shown below in Table 8.

TABLE 8

C-terminal modified CX3CR1-binding VHH domains

| Name | Sequence | SEQ ID NO: |
|---|---|---|
| CX3CR1BII18E06 | KVQLVESGGGLVQPGGSLRLSCATSGTIFSNNAMGWYRQAPGKKRDLVASISSSGSTNYADSVKGRFTVSRDNDKNTGYLQMNSLKPEDTGVYYCTLDARRGWNTAYWGQGAQVTVSSAAAEQKLISEEDLNGAAHHHHHH | 224 |
| CX3CR1BII66B02 | EVQLVESGGGSVQAGESLRLSCAASGSIFSSNAMAWYRQAPGKRRDLVAAINSVGVTKYADSVKGRFTISRDNAKNTVYLQMNSLKPEDTAVYYCTSDPRRGWDTRYWGQGTQVTVSSAAAEQKLISEEDLNGAAHHHHHH | 225 |
| CX3CR1BII315 | EVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTQVTVSSAAAEQKLISEEDLNGAAHHHHHH | 226 |
| CX3CR1BII316 | EVQLVESGGGSVQAGESLRLSCAASGSIFSSNAMAWYRQAPPGKQRDLVALINSVGITKYADSVKGRFTISSDNAKNTVYLEMNSLKPEDTAVYYCTSDGRRGWDTRYWGQGTQVTVSSAAAEQKLISEEDLNGAAHHHHHH | 227 |
| CX3CR1BII317 | EVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTLVTVSSGGGGSGGGGSGGGGSGGGGSGGGGSEVQLVESGGGLVQAGGSLRLSCVASGRTFSSYAMGWFRQAPGKERAFVAGISGSASRKYYADSVKGRFTVSRDNARNTVYLQMNSLKPEDTAVYYCAASNSYPKVQFDYYGQGTLVTVSSAAAEQKLISEEDLNGAAHHHHHH | 228 |

TABLE 8-continued

C-terminal modified CX3CR1-binding VHH domains

| | | |
|---|---|---|
| CX3CR1BI I1318 | EVQLVESGGGSVQAGESLRLSCAASGSIFSSNA MAWYRQAPGKRRDLVAAINSVGVTKYADSVK GRFTISRDNAKNTVYLQMNSLKPEDTAVYYCT SDPRRGWDTRYWGQGTQVTVSSGGGSGGGG SGGGGSGGGGSGGGSGGGGSGGGGSEVQLV ESGGGSVQAGESLRLSCAASGSIFSSNAMAWY RQAPGKRRDLVAAINSVGVTKYADSVKGRFTI SRDNAKNTVYLQMNSLKPEDTAVYYCTSDPRR GWDTRYWGQGTQVTVSSAAAEQKLISEEDLN GAAHHHHHH | SEQ ID NO: 229 |

The CX3CR1-targeting polypeptide components of the imaging agents described herein may be prepared by methods known in the art, for example, see U.S. application Ser. No. 13/775,307, incorporated herein by reference. Such methods generally comprise the steps of:
- culturing host cells comprising a nucleic acid capable of encoding the desired polypeptide under conditions that allow expression of the polypeptide of the invention; and,
- recovering or isolating the polypeptide expressed by the host cells from the culture; and
- optionally further purifying and/or modifying and/or formulating the polypeptide of the invention.

In one aspect of the invention these imaging agents may be used in non-invasive imaging of atherosclerosis, for example to diagnose atherosclerotic disease. In another aspect the imaging agents of the invention would be useful as a companion diagnostic for a CX3CR1-antagonist therapeutic. That is, they may be used for patient stratification, i.e. to pre-select patients with atherosclerosis that may respond favorably to a CX3CR1-antagonist therapeutic. The imaging agents may also be used to monitor the effects of treatment with any therapeutic by evaluating the progression or regression of the atherosclerotic lesion.

In another aspect of the invention, the imaging agents may be used in non-invasive imaging to diagnose other diseases characterized by increased expression of CX3CR1. Increased CX3CR1 expression is also known to be associated with multiple inflammatory disease states or conditions including cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, pancreatitis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, and cancer.

Single variable domain polypeptides, such as VHH domains have favorable properties for use in imaging agents. They have high affinity and specificity for their target as well as good physicochemical properties such as serum stability. They have molecular weights below the renal cutoff for glomerular filtration and therefore are rapidly cleared, allowing in vivo imaging of the tissues where specific binding occurs. In one embodiment the CX3CR1-binding single variable domain comprising the imaging agent is a monovalent VHH domain. In another embodiment it is bivalent, comprising two VHH domains, which may be identical or different, covalently linked by a linker peptide. The linker peptide may be a naturally occurring sequence or a non-naturally occurring sequence, preferably non-immunogenic. Non-limiting examples of linker sequences are Gly/Ser linkers of different length such as $(gly_xser_y)_z$ linkers, including $(gly_4ser)_3$ (SEQ ID NO: 231), $(gly_4ser)_4$ (SEQ ID NO: 232), $(gly_4ser)$ (SEQ ID NO: 233), $(gly_3ser)$ (SEQ ID NO: 234), $gly_3$, and $(gly_3ser_2)_3$ (SEQ ID NO: 235).

For use as an imaging agent the single variable domain polypeptide is linked to a detection label. Various detection labels and linking methods are known in the art. For example, non-limiting examples of detection labels may include fluorescent, chemiluminescent, bioluminescent, phosphorescent labels, paramagnetic labels, radioisotope or radiotracer labels, microbubbles or imaging dyes. The detection label may be selected according to the desired use and imaging application.

Various imaging technologies are well known and currently in use in the art. Non-limiting examples of imaging applications or technologies that may be used include:

Single photon emission computed tomography (SPECT). Non-limiting examples of radio-isotopes that may be used in detection labels for SPECT imaging include $^{99m}$Tc, $^{111}$In, $^{123}$I, $^{201}$Tl and $^{133}$Xe.

Positron emission tomography (PET). Non-limiting examples of radio-isotopes that may be used in detection labels for PET imaging include $^{11}$C, $^{64}$Cu, $^{18}$F, $^{68}$Ga, $^{13}$N, $^{15}$O, $^{82}$Rb, $^{124}$I and $^{89}$Zr.

Near infrared fluorescence imaging (NIR or NIRF). Non-limiting examples of imaging dyes that may be used in detection labels for NIRF include Cy5.5, Alexa680, Dylight680, Dylight800 and IRDye800CW.

Ultrasound imaging. A non-limiting example of a detection label suitable for ultrasound imaging is microbubbles.

Magnetic resonance imaging (MRI). Non-limiting examples of paramagnetic materials suitable for MRI imaging include iron oxide or carbon-coated iron-cobalt nanoparticles and gadolinium chelates.

Methods for linking detection labels to a targeting antibody fragment, for example a CX3CR1-targeting single domain polypeptide, are well known in the art. Detection labels may be linked directly or indirectly, via another linking molecule, to the targeting polypeptide. The detection label may be joined covalently, for example by formation of an amide bond with an amino acid, or non-covalently, for example by an ionic interaction with a linking, chelating molecule.

Non-limiting examples of a covalent linking method include:

$^{99m}$Tc linking by a tricarbonyl method. $^{99m}$Tc-tricarbonyl is reacted with the hexahistidine tagged-targeting polypeptide ("hexahistidine" disclosed as SEQ ID NO: 230) followed by purification (for example, see V. Cortez-Retamozo, 2008; Curr Radiopharm 1:37).

IRDye800CW linking by NHS-ester method. IRDye800CW N-hydroxysuccinimide (NHS) ester is reacted with the targeting polypeptide followed by purification (for example, see S. Oliveira, 2012; Mol. Imaging, 7:254-264).

Microbubble linking by biotin-streptavidin bridge. Targeting polypeptide is biotinylated. The biotinylated targeting polypeptide is coupled to biotinylated microbubble by biotin-streptavidin bridge (for example, see S. Hernot, 2012; J. Control. Release 158:346-353).

A non-limiting example of a chelating linking method includes:

The targeting polypeptide is reacted with Df-Bz-NCS to form the chelating linker. The modified targeting polypeptide is then radiolabeled with $^{68}$Ga. (for example, see M. J. W. D. Vosjan, 2011; *Eur J. Nucl. Med. Mol. Imaging*, 38:753-763).

The targeting polypeptide is conjugated with S-2-(4-isothiocyanatobenzyl)-1,4,7-triazacyclononane-1,4,7-triacetic acid (pSCN-Bn-NOTA) and then radiolabelled with $^{68}$Ga. (for example, see C. Xavier, 2013; *J. Nucl. Med.*, 54: 776-784).

For use in in vivo imaging, the imaging agents of the invention may be formulated as a pharmaceutical preparation comprising (i) at least one imaging agent of the invention and (ii) at least one pharmaceutically acceptable carrier, diluent, excipient, adjuvant, and/or stabilizer. By "pharmaceutically acceptable" is meant that the respective material does not show any biological or otherwise undesirable effects when administered to an individual and does not interact in a deleterious manner with any of the other components of the pharmaceutical composition (such as e.g. the imaging agent) in which it is contained. Specific examples can be found in standard handbooks, such as e.g. Remington's Pharmaceutical Sciences, 18$^{th}$ Ed., Mack Publishing Company, USA (1990). For example, the imaging agents of the invention may be formulated and administered in any manner known per se for conventional antibodies and antibody fragments and other pharmaceutically active proteins. Thus, according to a further embodiment, the invention relates to a pharmaceutical composition or preparation that contains at least one imaging agent of the invention and at least one pharmaceutically acceptable carrier, diluent, excipient, adjuvant and/or stabilizer.

Such a formulation may be in a form suitable for parenteral administration (such as by intravenous, intramuscular, subcutaneous, intrathecal, intracavernosal or intraperitoneal injection or intravenous infusion). Such suitable administration forms—which may be solid, semi-solid or liquid, depending on the manner of administration—as well as methods and carriers for use in the preparation thereof, will be clear to the skilled person. The preferred formulation and route of administration would be known by one skilled in the art and would depend in part on the imaging method being used and tissue being examined.

Preparations for parenteral administration may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

For use in in vivo imaging a detectable amount of the composition containing the imaging agent is administered to a subject. The detectable amount may vary depending on a number of factors including the imaging agent, the route of administration, the imaging method and the subject and tissue being examined and can be determined by one skilled in the art.

The invention provides a method for detecting CX3CR1-containing atherosclerotic plaques in vivo comprising:
1) administering an imaging agent of the present invention to a subject; and
2) detecting the presence of the bound imaging agent in the vasculature being examined;

wherein the presence of the bound imaging agent indicates the presence of atherosclerotic plaque.

Vasculature that may be examined by in vivo imaging for detecting atherosclerotic plaque includes, for example, the carotid artery, coronary artery, femoral artery, abdominal artery and thoracic artery.

The invention also provides a method for ex vivo detection of atherosclerotic disease comprising:
1) providing a sample of tissue suspected of containing atherosclerotic plaque;
2) contacting the tissue with an imaging agent of the invention;
3) removing unbound imaging agent; and
4) detecting specifically bound imaging agent in the sample;

wherein the presence of the bound imaging agent indicates the presence of atherosclerotic plaque.

In a further aspect, the invention provides the following:

Embodiment 1

An imaging agent comprising a CX3CR1-targeting polypeptide linked to a detection label.

Embodiment 2

An imaging agent according to embodiment 1, wherein the CX3CR1-targeting polypeptide is an immunoglobulin single variable domain.

Embodiment 3

An imaging agent according to embodiment 1 or 2, wherein the CX3CR1-targeting polypeptide is a VHH domain.

Embodiment 4

An imaging agent according to any one of embodiments 1 to 3, wherein the CX3CR1-targeting polypeptide includes CDR1, CDR2 and CDR3 sequences selected from:
SEQ ID No: 141, 162 and 186, respectively; or
SEQ ID No: 141, 163 and 187, respectively; or
SEQ ID No: 141, 164 and 186, respectively; or
SEQ ID No: 141, 166 and 186, respectively; or
SEQ ID No: 141, 167 and 186, respectively; or
SEQ ID No: 141, 167 and 189, respectively; or
SEQ ID No: 141, 168 and 186, respectively; or
SEQ ID No: 141, 168 and 187, respectively; or
SEQ ID No: 141, 169 and 190, respectively; or
SEQ ID No: 141, 170 and 186, respectively; or
SEQ ID No: 141, 171 and 186, respectively; or
SEQ ID No: 141, 174 and 186, respectively; or
SEQ ID No: 141, 175 and 187, respectively; or
SEQ ID No: 142, 165 and 188, respectively; or
SEQ ID No: 142, 173 and 188, respectively; or
SEQ ID No: 143, 164 and 186, respectively; or
SEQ ID No: 144, 172 and 187, respectively; or
SEQ ID No: 145, 172 and 187, respectively; or
SEQ ID No: 141, 214 and 186, respectively; or
SEQ ID No: 141, 215 and 186, respectively; or
SEQ ID No: 141, 216 and 186, respectively; or
SEQ ID No: 141, 217 and 186, respectively; or
SEQ ID No: 141, 218 and 186, respectively; or
SEQ ID No: 141, 219 and 186, respectively; or
SEQ ID No: 141, 220 and 186, respectively; or
SEQ ID No: 213, 221 and 186, respectively; or SEQ ID No: 213, 214 and 186, respectively; or
SEQ ID No: 146, 176 and 191, respectively; or
SEQ ID No: 146, 177 and 191, respectively; or
SEQ ID No: 147, 178 and 192, respectively; or
SEQ ID No: 147, 179 and 192, respectively; or
SEQ ID No: 147, 179 and 194, respectively; or
SEQ ID No: 148, 179 and 193, respectively; or
SEQ ID No: 149, 179 and 192, respectively; or
SEQ ID No: 149, 180 and 192, respectively; or
SEQ ID No: 149, 181 and 192, respectively; or
SEQ ID No: 149, 183 and 192, respectively; or
SEQ ID No: 149, 185 and 192, respectively; or
SEQ ID No: 150, 179 and 194, respectively; or
SEQ ID No: 150, 182 and 194, respectively; or
SEQ ID No: 151, 179 and 193, respectively; or
SEQ ID No: 151, 182 and 194, respectively; or
SEQ ID No: 151, 184 and 196, respectively; or
SEQ ID No: 152, 179 and 195, respectively; or
SEQ ID No: 153, 179 and 194, respectively; or
SEQ ID No: 154, 182 and 194, respectively; or
SEQ ID No: 155, 179 and 195, respectively; or
SEQ ID No: 156, 181 and 192, respectively; or
SEQ ID No: 157, 179 and 194, respectively; or
SEQ ID No: 158, 179 and 192, respectively; or
SEQ ID No: 159, 178 and 192, respectively; or
SEQ ID No: 160, 179 and 194, respectively; or
SEQ ID No: 161, 179 and 194, respectively.

Embodiment 5

An imaging agent according to any one of embodiments 1 to 4, wherein the CX3CR1-targeting polypeptide includes CDR1, CDR2 and CDR3 sequences selected from:
SEQ ID No: 141, 162 and 186, respectively; or
SEQ ID No: 141, 214 and 186, respectively; or
SEQ ID No: 141, 215 and 186, respectively; or
SEQ ID No: 141, 216 and 186, respectively; or
SEQ ID No: 141, 217 and 186, respectively; or
SEQ ID No: 141, 218 and 186, respectively; or
SEQ ID No: 141, 219 and 186, respectively; or
SEQ ID No: 141, 220 and 186, respectively; or
SEQ ID No: 213, 221 and 186, respectively; or
SEQ ID No: 213, 214 and 186, respectively; or
SEQ ID No: 147, 178 and 192, respectively; or
SEQ ID No: 146, 176 and 191, respectively.

Embodiment 6

An imaging agent according to any one of embodiments 1-3, wherein the CX3CR1-targeting polypeptide is a VHH domain having a sequence selected from:
any one of SEQ ID No's: 1-140 or 197-202.

Embodiment 7

An imaging agent according to embodiment 6, wherein the CX3CR1-targeting polypeptide is a VHH domain having a sequence selected from:
any one of SEQ ID No's: 1, 11, 49, 53, 121-140 or 197-202.

Embodiment 8

An imaging agent according to embodiment 1 or 2, wherein the CX3CR1-targeting polypeptide is bivalent comprising two VHH domains, which may be identical or different, covalently linked by a linker peptide, wherein the sequence of the VHH domains are selected from:
any one of SEQ ID No's: 203-212, 222 or 223.

Embodiment 9

An imaging agent according to any one of embodiments 1, 2 or 8, wherein the sequence of the bivalent CX3CR1-targeting polypeptide is selected from:
any one of SEQ ID No's: 208, 222 or 223.

Embodiment 10

An imaging agent according to any one of embodiments 1-9, wherein the detection label is selected from a radio-isotope, an imaging dye, a paramagnetic material or a microbubble.

Embodiment 11

An imaging agent according to any one of embodiments 1-10, wherein the detection label is a radio-isotope.

Embodiment 12

An imaging agent according to any one of embodiments 1-11, wherein the detection label is selected from $^{99m}$Tc, $^{111}$In, $^{123}$I, $^{201}$Tl, $^{133}$Xe, $^{11}$C, $^{64}$Cu, $^{18}$F, $^{68}$Ga, $^{13}$N, $^{15}$O, $^{82}$Rb, $^{124}$I and $^{89}$Zr.

Embodiment 13

An imaging agent according to any one of embodiments 1-12, wherein the detection label is selected from $^{99m}$Tc and $^{68}$Ga.

Embodiment 14

An imaging agent according to embodiment 1, wherein the CX3CR1-targeting polypeptide is an immunoglobulin that competes for binding to CX3CR1 with a VHH domain selected from:
any one of SEQ ID No's: 224, 225, 226, 227 or 228.

Embodiment 15

An in vivo method for diagnosing a disease characterized by increased expression of CX3CR1 in a subject, comprising:
a) administering an imaging agent according to any one of embodiments 1-14;
b) detecting the binding of the imaging agent;
wherein the imaging agent specifically binds to CX3CR1 in the affected tissue at a level detectably higher than in undiseased tissue and the observed binding is indicative of said disease.

Embodiment 16

An in vivo method for diagnosing a disease characterized by increased expression of CX3CR1 in a subject, the method comprising:
a) administering to a subject an imaging agent according to any of embodiments 1-14; and
b) detecting a higher level of binding of the imaging agent in affected tissue in the subject as compared to undiseased tissue.

Embodiment 17

A method according to embodiment 15 or 16, wherein the disease is selected from cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, pancreatitis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, and cancer.

Embodiment 18

A method according to any one of embodiments 15-17, wherein the disease is atherosclerosis.

Embodiment 19

A method according to any one of embodiments 15-18 wherein the method for detecting the binding of the imaging agent is selected from:
a) single photon emission computed tomography;
b) positron emission tomography;
c) near infrared fluorescence imaging;
d) ultrasound imaging; and
e) magnetic resonance imaging.

Embodiment 20

A method according to any one of embodiments 15-19 wherein the method for detecting the binding of the imaging agent is positron emission tomography.

Embodiment 21

A method according to any one of embodiments 15-20, wherein the subject is a human.

Embodiment 22

An ex vivo method for diagnosing a disease characterized by increased expression of CX3CR1 in a subject, comprising:
1) contacting the tissue suspected of being affected by the disease from the subject with an imaging agent according to any of embodiments 1-14;
2) removing unbound imaging agent; and
3) detecting specifically bound imaging agent in the sample;
wherein the imaging agent specifically binds to CX3CR1 in the affected tissue at a level detectably higher than undiseased tissue and the observed binding is indicative of CX3CR1-mediated disease.

Embodiment 23

An ex vivo method for diagnosing a disease characterized by increased expression of CX3CR1 in a subject, comprising:
1) contacting a tissue sample from a subject with an imaging agent according to any of embodiments 1-14; and
2) detecting specifically bound imaging agent in the sample.

Embodiment 24

A method for identifying and treating patients suffering from a disease characterized by increased expression of CX3CR1 comprising:
a) administering an imaging agent according to any of embodiments 1-14;
b) detecting the binding of the imaging agent;
wherein, if the imaging agent specifically binds to CX3CR1 in the affected tissue at a level detectably higher than undiseased tissue, treating the patient with a therapeutically effective amount of a therapeutic agent known to be effective for said disease.

Embodiment 25

A method for treating a patient having a disease characterized by increased expression of CX3CR1 comprising:
a) identifying a patient as having a higher level of binding of the imaging agent according to any of embodiments 1-14 in affected tissue compared to undiseased tissue;
b) administering a therapeutic agent to the patient.

Embodiment 26

The method according to embodiment 24 or 25, wherein the disease is selected from cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, pancreatitis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, and cancer.

Embodiment 27

The method according to embodiment 25 or 26, wherein the disease is atherosclerosis.

Embodiment 28

The method according to any of embodiments 24 to 27, wherein the effective therapeutic agent is a CX3CR1 antagonist.

Embodiment 29

A method for the manufacturing of an imaging agent according to any of embodiments 1 to 14 comprising the steps of
a) production of the CX3CR1-targeting polypeptide,
b) binding of the detection label and
c) optionally admixing further excipients.

Embodiment 30

Use of a detection label selected from a radio-isotope, an imaging dye, a paramagnetic material or a microbubble for the manufacturing of an imaging agent according to any of embodiments 1 to 14.

Embodiment 31

Use of an imaging agent according to any of embodiments 1 to 14 for the preparation of a composition for the diagnosis of a disease characterized by increased expression of CX3CR1 in a subject.

Embodiment 32

A composition comprising an imaging agent according to any of embodiments 1 to 14 for use in a method for the diagnosis of a disease characterized by increased expression of CX3CR1 in a subject.

Embodiment 33

A kit for use in a method for the diagnosis of a disease characterized by increased expression of CX3CR1 in a subject comprising an imaging agent according to any of embodiments 1 to 14.

Embodiment 34

The kit according to embodiment 33 further comprising instructions for use in a method for the diagnosis of a disease characterized by increased expression of CX3CR1 in a subject.

Embodiment 35

A polypeptide comprising an anti-CX3CR1 immunoglobulin single variable domain, wherein said polypeptide is capable of blocking the binding of human fractalkine to human CX3CR1, wherein said anti-CX3CR1 immunoglobulin single variable domain is a VHH domain comprising the sequence set forth in any one of SEQ ID NO: 200-202.

Embodiment 36

A nucleic acid molecule encoding a polypeptide according to embodiment 35.

Embodiment 37

A pharmaceutical composition comprising (i) a polypeptide according to embodiment 35, and (ii) a pharmaceutically acceptable carrier, and optionally (iii) a diluent, excipient, adjuvant and/or stabilizer.

Embodiment 38

A method for the treatment of a CX3CR1-associated disease, disorder or condition, comprising administering a therapeutic amount of a compound according to embodiment 35 to a patient in need thereof.

Embodiment 39

The method according to embodiment 38, wherein the disease, disorder or condition is selected from cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, or cancer.

Embodiment 40

The method according to embodiment 39, wherein the disease, disorder or condition is atherosclerosis.

EXAMPLES

Example 1

Generation of Anti-Human CX3CR1 VHH Domains

Llamas were immunized according to standard protocols with pVAX1-hCX3CR1 plasmid vector (Invitrogen, Carlsbad, Calif., USA), Camel Kidney (Caki) cells overexpressing human CX3CR1 and/or recombinant peptides derived from the N-terminus and the third extracellular loop of CX3CR1 coupled to BSA. Peptides were ordered at Neo MPS (Polypeptidegroup, Strasbourg, France) and coupled to BSA according to standard protocols. At various times during the immunizations and following the final immunogen injection, blood samples and lymph node biopsies which served as the source of B-cells that produce the heavy-chain antibodies were collected from the llamas. From the blood samples, peripheral blood lymphocytes (PBLs) were prepared using Ficoll-Hypaque according to the manufacturer's instructions (Amersham Biosciences, Piscataway, N.J., USA). From the PBLs and the lymph node biopsies (LN), total RNA was extracted, which was used as starting material for RT-PCR to amplify the VHH encoding DNA segments.

From each immunized llama, libraries were constructed by pooling the total RNA isolated from samples originating from a certain subset of the immunization schedule i.e. after one type of immunization antigen, and for some llamas samples from the different animals were pooled into one library. In short, the PCR-amplified VHH repertoire was cloned via specific restriction sites into a vector designed to facilitate phage display of the VHH library. The vector was derived from pUC119 and contains the LacZ promoter, a M13 phage gIII protein coding sequence, a resistance gene for ampicillin or carbenicillin, a multiple cloning site and a hybrid gIII-pelB leader sequence (pAX050). In frame with the VHH coding sequence, the vector encodes a C-terminal c-myc tag and a hexahistidine tag (SEQ ID NO: 230). Phages were prepared according to standard protocols and stored after filter sterilization at 4° C. or at −80° C. in 20% glycerol for further use.

VHH repertoires obtained from all llamas and cloned as phage libraries were used in different selection strategies, applying a multiplicity of selection conditions. All solid coated phase selections were done in Maxisorp 96-well plates (Nunc, Wiesbaden, Germany). Selections were performed as follows: CX3CR1 antigen preparations for solid (CX3CR1 expressed on liposomes/VLPs, Integral Molecular, Philadelphia, Pa., USA) and solution (cells recombinantly expressing CX3CR1) phase selection formats were presented at multiple concentrations. After 2 hours incubation with the phage libraries followed by extensive washing, bound phages were eluted with trypsin (1 mg/mL) for 15 minutes. When trypsin was used for phage elution, the protease activity was immediately neutralized by applying 0.8 mM protease inhibitor ABSF. As a control, selections without antigen were performed in parallel.

Phage outputs were used to infect *E. coli* which were then in turn used to prepare phage for the next selection round (phage rescue) After the second round selection the phage outputs were used to infect *E. coli* which were then plated on agar plates (LB+carb+glucose$^{2\%}$) for analysis of individual VHH clones. In order to screen a selection output for specific binders, single colonies were picked from the agar plates and grown in 1 mL 96-deep-well plates. LacZ-controlled VHH expression was induced by adding IPTG (1 mM final) in the absence of glucose. Periplasmic extracts (in a volume of ~80 uL) were prepared according to standard protocols.

Periplasmic extracts were screened in a human CX3CR1/human fractalkine FACS competition assay to assess the ability of the expressed VHHs to block the binding of the unique CX3CR1 ligand to the receptor. Human CX3CR1 was presented on CHO cells. As a detection reagent fractalkine (R&D Systems, Minneapolis, Minn., USA) labeled with Alexa Fluor 647 (A647-Fractalkine) at a degree of labeling of 1 was used. In brief, 50 µl of periplasmic extract was added to 6 nM labeled fractalkine (50 µl) and 2E5 CHO-hCX3CR1 cells. After one hour incubation at 4° C., cells were washed three times before analysis on a FACS Array (Becton Dickinson). First a gate was set on the intact cells as determined from the scatter profile. Next, dead cells were gated out by their fluorescence profile from the PI stain (Sigma, St Louis, US). The fluorescence profile from the Alexa Fluor 647 label was determined for each sample and used for the calculation of blocking capacity. As controls, conditions were taken along where there was no VHH present in the periplasmic extract or a known irrelevant VHH and samples were included with excess cold fractalkine. For each sample the percentage block was determined using the control samples to determine the assay window.

From this screening, VHHs were selected and sequence analysis revealed unique VHHs belonging to 3 different B-cell lineages designated families 9, 13 and 101. In order to determine whether formatting monovalent VHHs as bivalent molecules would increase potency and/or efficacy, bivalent molecules were constructed by genetic engineering. Two VHHs were genetically linked together with a 35GS linker in between the two building blocks.

Anti-CX3CR1 VHHs were expressed and purified for further characterization. Monovalent and bivalent VHHs were expressed in *E. coli* TG1 as c-myc, His6-tagged proteins ("His6" disclosed as SEQ ID NO: 230). Expression was induced by addition of 1 mM IPTG and allowed to continue for 4 hours at 37° C. After spinning the cell cultures, periplasmic extracts were prepared by freeze-thawing the pellets. These extracts were used as starting material and VHHs were purified via IMAC and size exclusion chromatography (SEC) resulting in 95% purity as assessed via SDS-PAGE.

Representative epitope tagged monovalent and bivalent VHH domains from different families and with diverse predicted charge and pI were selected for evaluation as imaging reagents. All of these VHH domains were shown to block fractalkine binding to the receptor in the competition FACS assay outlined above. Either BA/F3-hCX3CR1 cells, CHO-hCX3CR1 cells or transiently transfected HEK293T cells were used. The amount of labeled ligand used in the different competition setups was also varied. The $IC_{50}$ values for VHHs blocking the interaction of human fractalkine to human CX3CR1 are depicted Table 9.

Specificity for the hCX3CR1 receptor was evaluated by performing a FACS binding experiment on CHO-K1 parental cells or CHO cells expressing human CCR2, human CCR5 or mouse CX3CR1. The VHHs were incubated with the respective cell lines for 30 minutes at 4° C. followed by three wash steps and subsequently incubated with the detection reagents. As detection, a mouse anti-cmyc antibody (Serotec, MCA2200) followed by a goat anti-mouse antibody coupled to PE (Jackson 115-116-071) was used, each incubation was for 30 minutes at 4° C. and was followed by three wash steps. For each cell line a quality control with receptor-specific antibody was included. In addition, the highest concentration of each VHH was also incubated with CHO cells expressing hCX3CR1 as a positive control. No binding to mouse CX3CR1, human CCR2 or human CCR5 could be observed.

TABLE 9

Characteristics of the VHH Domains selected for imaging study

| Sample ID | Family | Charge/pI | Cell Line | $IC_{50}$ (M) | % Block | Repeats |
|---|---|---|---|---|---|---|
| CX3CR1BII18E06 | 13 | 3/7.67 | BA/F3-hCX3CR1 | 2.8E-9 | 71 | 3 |
| CX3CR1BII66B02 | 101 | 4/8.24 | HEK 293-hCX3CR1 | 2.5E-9 | 102 | 2 |
| CX3CR1BII315 | 9 | 5/8.65 | BA/F3-hCX3CR1 | 8.1E-9 | 100 | 3 |
| CX3CR1BII316 | 101 | 1/6.79 | HEK 293-hCX3CR1 | 5.3E-9 | 94 | 5 |
| CX3CR1BII317 | 9 bivalent | 10/9.29 | CHO-hCX3CR1 | 3.4E-9 | 105 | 4 |
| CX3CR1BII318 | 101 bivalent | 8/9.05 | HEK 293-hCX3CR1 | 3.0E-10 | 102 | 2 |

Example 2

Labeling of VHH Domains

Radiolabeling of VHH Domains

VHH domains were radiolabeled site-specifically on their hexahistidine tags (SEQ ID NO: 230) with $^{99m}$Tc using the $^{99m}$Tc-tricarbonyl-method. [$^{99m}$Tc(H$_2$O)$_3$(CO)$_3$]$^+$ ($^{99m}$Tc-tricarbonyl) was synthesized by adding $^{99m}$TcO$_4^-$ solution ($^{99}$Mo/$^{99m}$Tc generator eluate; 0.74-3.7 GBq; Drytec; GE Healthcare, Piscataway, N.J.) to an Isolink kit (Covidien, St Louis, Mo.). The vial was incubated at 100° C. for 20 minutes. After cooling, the $^{99m}$Tc-tricarbonyl solution was neutralized to pH 7.4 with 1 M HCl. 500 µl $^{99m}$Tc-tricarbonyl was then added to 50 µl of VHH domain (1 mg/ml for monovalent VHH domains, 2 mg/ml for bivalent VHH domains) and incubated for 90 minutes at 50° C. Separation of labeled molecules from free label and buffer exchange into phosphate buffered saline (PBS) was carried out by gel filtration using Sephadex G25 disposable columns (NAP-5; GE Healthcare, Piscataway, N.J.). The labeled VHH domains were then passed through a 0.22 µm filter (Millipore, Bedford, Mass.) to remove aggregates.

All VHH domains were successfully labeled with $^{99m}$Tc. Radiochemical purity was shown to be >95% by Instant Thin Layer Chromatography using acetone as the mobile phase. The radiochemical purity was also assessed by RP-HPLC analysis and shown to be >89% using an analytical C4 column 214TP53 (Grace Vydac, Deerfield, Ill.) with 0.1% trifluoracetic acid in $H_2O$ (solvent A)/0.1% trifluoracetic acid in acetonitrile (solvent B) gradient as the mobile phase.

Example 3

In Vitro Cell Binding of Labeled VHH Domains

To confirm that the labeled VHH domain molecules retained their binding to CX3CR1, binding studies were carried out utilizing CHO-hCX3CR1 cells. Untransfected CHO cells (CHO-WT) were included as controls. CHO-hCX3CR1 or CHO-WT cells were plated at 2 E5 cells/well in 24-well plates containing F12 medium supplemented with 10% FBS, 500 µg/ml G418 and 100 µg/ml Zeocin (CHO-hCX3CR1) or RPMI medium supplemented with 10% FBS, 100 U/ml Penicillin, 100 µg/ml Streptavidin and 2 mM L-glutamine (CHO-WT) and incubated overnight at 37° C. After blocking of non-specific binding with 0.5% HSA in F12 medium, 1 nM of $^{99m}$Tc-VHH domain in 0.5 ml F12 medium+0.5% HSA was added to the wells in triplicate and the plates were incubated for 1 hour at 37° C. Unbound $^{99m}$Tc-VHH domain was removed by washing the cells three times with ice-cold PBS+0.5% HSA. The cells were solubilized with 1 M NaOH and $^{99m}$Tc- was quantitated in a gamma-well counter (Cobra II Inspector 5003, Canberra-Packard). The results are shown in FIG. 1. Specific binding to CHO-hCX3CR1 cells was normalized to the binding on CX3CR1-negative CHO-WT cells (binding/binding on CHO-WT cells). For statistical analysis an unpaired Student-t-test was used (SPSS Statistics 20). P-values<0.05 were considered significant.

Binding to CX3CR1-positive CHO cells was significantly higher than to untransfected cells for all six $^{99m}$Tc-labeled VHH domains (*p≤0.001) demonstrating that specific binding to CX3CR1 was preserved with the $^{99m}$Tc-labeling of the VHH domains. While strong binding and a large window was observed with 5 of the 6 VHH domains, weaker binding was seen with CX3CR1BII315.

Example 4

Biodistribution of Labeled VHH Domains in Healthy hCX3CR1 KI and C57BL/6 Mice

Experiments were carried out to examine the biodistribution of the labeled VHH domains in healthy (nondiseased) mice. Since the VHH domains identified did not cross react with mouse CX3CR1, a human CX3CR1 knock-in mouse line (hCX3CR1 KI) was generated at TaconicArtemis (Koeln, Germany) to enable testing of these molecules in mouse disease models. A strategy was employed that allowed the expression of the human chemokine receptor under the control of the corresponding mouse promoter while disrupting the expression of the endogenous mouse protein. Briefly, a targeting vector was constructed where the mouse CX3CR1 coding region in exon 2 was replaced with the complete human CX3CR1 open reading frame and flanked by selection markers and loxP sites. The targeting vector was introduced into mouse ES cells and clones that had successfully undergone homologous recombination were used to generate chimeric mice. These mice were bred to highly efficient Flp-deleter mice to achieve removal of the selection marker and germline transmission. C57BL/6 mice were utilized as controls to evaluate non-specific target independent binding.

Figure 2:
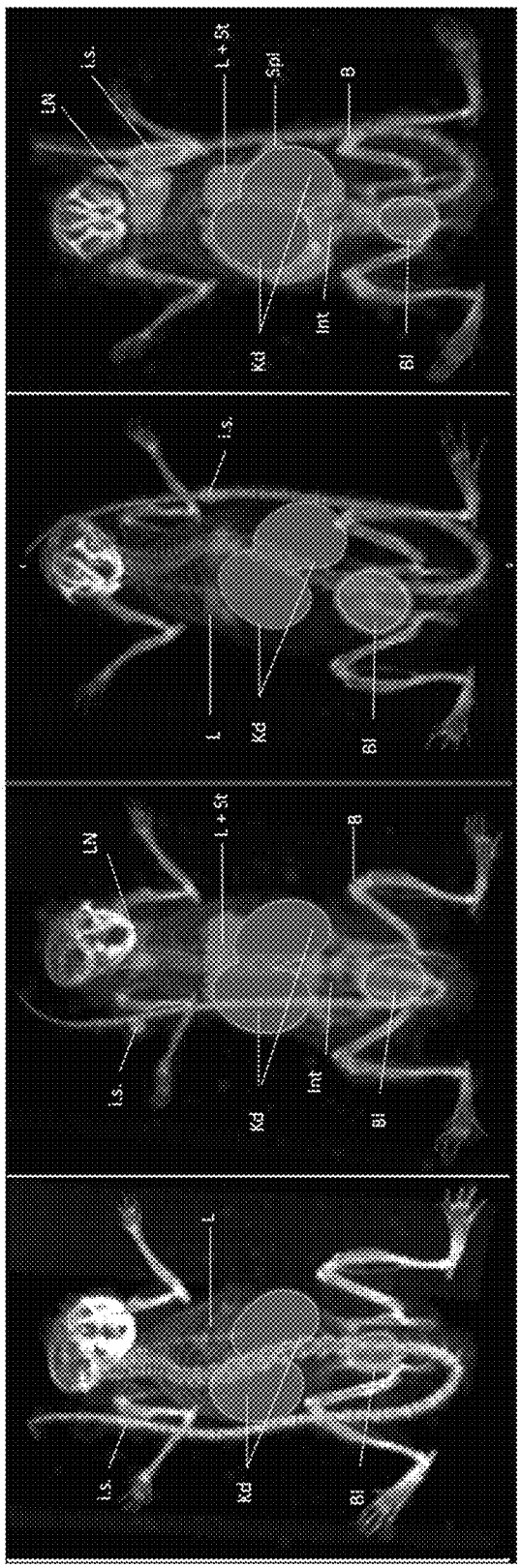
FIG. 2: Representative in vivo SPECT/CT whole-body maximum intensity projection images of the biodistribution of monovalent VHH domain $^{99m}$Tc-CX3CR1BII66B02 and bivalent VHH domain $^{99m}$Tc-CX3CR1BII318 in C57BL/6 and hCX3CR1 KI mice obtained 3 hours after intravenous injection. L=liver, Kd=Kidney, Bl=Bladder, LN=lymph node, St=Stomach, B=Bone, Int=Intestines, Spl=Spleen, i.s.=injection site.

17 week old female C57BL/6 (n=35) and hCXCR3 KI mice (n=35) were fed a normal chow diet. Each VHH domain was evaluated in six C57BL/6 and six hCX3CR1 KI mice, except $^{99m}$Tc-CX3CR1BII315 (2×n=5). 100 µl of the $^{99m}$Tc-VHH domain solution (53±10 MBq) was injected intravenously via the tail vein. Three hours post-injection, anesthetized animals were placed in prone position in an animal bed along with six $^{57}$Co landmarks and sequentially subjected to pinhole-SPECT and microCT. The pinhole-SPECT acquisitions were performed using a dual-headed gamma camera (e.cam$^{180}$ Siemens Medical Solutions, Wheaton, Ill., USA) equipped with a triple 1.5 mm pinhole collimator. Sixty-four projections, 10 seconds each, were acquired over 360° of rotation into a 128×128 matrix with a zoom factor of 1. The microCT imaging was performed on a Skyscan 1178 (Skyscan, Kontich, Belgium) using the following acquisition parameters: 50 kV, 615 µA and 83 µm resolution. After reconstruction, both data sets were automatically fused on the basis of the six $^{57}$Co landmarks. Images were analyzed with the software Amide (http://amide.sourceforge.net) and Osirix (Pixmeo SARL, Bernex, Switzerland). The color scale of SPECT images was normalized to % IA/cm$^3$ to allow direct visual comparison between the animals (FIG. 2).

After the imaging, animals were euthanized by an overdose of sodium pentobarbital (CEVA, Libourne, France). All major organs and tissues were harvested, weighed and their radioactivity was quantitated in the gamma-well counter. Counts were corrected for background and decay, and expressed as percentage of injected activity per gram tissue (% IA/g). Statistical analysis was performed using both a parametric test (ANOVA) and a non-parametric test (Mann-Whitney U) (SPSS Statistics 20). P-values<0.05 were considered significant.

The biodistribution data of the $^{99m}$Tc-VHH domains in C57BL/6 and hCX3CR1 KI mice are summarized in Table 10.

TABLE 10

Ex Vivo VHH domain biodistribution in C57BL/6 and hCX3CR1 KI mice

| | 18E06 | | 66B02 | | 315 | |
|---|---|---|---|---|---|---|
| | C57Bl/6 n = 6 | hCX3CR1 KI n = 6 | C57Bl/6 n = 6 | hCX3CR1 KI n = 6 | C57Bl/6 n = 5 | hCX3CR1 KI n = 5 |
| Heart | 0.24 ± 0.03 | 0.34 ± 0.04* | 0.19 ± 0.02 | 044 ± 0.05* | 0.35 ± 0.10 | 0.40 ± 0.07 |
| Lungs | 0.47 ± 0.11 | 0.88 ± 0.11* | 0.45 ± 0.12 | 1.11 ± 0.21* | 0.70 ± 0.15 | 0.83 ± 0.21 |
| Liver | 1.31 ± 0.12 | 1.81 ± 0.15* | 1.55 ± 0.16 | 1.85 ± 0.17* | 1.94 ± 0.27 | 2.00 ± 0.20 |
| Spleen | 0.47 ± 0.04 | 1.41 ± 0.21* | 0.58 ± 0.08 | 2.22 ± 0.36* | 0.66 ± 0.29 | 0.77 ± 0.09 |
| Pancreas | 0.13 ± 0.02 | 0.22 ± 0.04* | 0.11 ± 0.02 | 0.26 ± 0.03* | 0.17 ± 0.02 | 0.19 ± 0.02 |
| Left Kidney | 237 ± 30 | 228 ± 29 | 279 ± 45 | 218 ± 31* | 206 ± 47 | 235 ± 15 |
| Right Kidney | 233 ± 28 | 243 ± 27 | 298 ± 32 | 233 ± 29* | 217 ± 50 | 257 ± 11 |
| Brain | 0.01 ± 0.00 | 0.03 ± 0.00* | 0.01 ± 0.00 | 0.03 ± 0.01* | 0.02 ± 0.00 | 0.02 ± 0.01 |
| Aorta | 0.16 ± 0.02 | 0.19 ± 0.04 | 0.15 ± 0.04 | 0.24 ± 0.05* | 0.29 ± 0.08 | 0.32 ± 0.10 |
| Stomach | 0.24 ± 0.10 | 0.42 ± 0.06* | 0.21 ± 0.06 | 0.80 ± 0.20* | 0.28 ± 0.06 | 0.35 ± 0.08 |
| Small Intestine | 0.35 ± 0.05 | 1.22 ± 0.25* | 0.38 ± 0.10 | 2.32 ± 0.29* | 0.69 ± 0.44 | 0.57 ± 0.10 |
| Large Intestine | 0.27 ± 0.19 | 1.12 ± 0.31* | 0.24 ± 0.06 | 1.48 ± 0.68* | 0.38 ± 0.33 | 0.53 ± 0.38 |
| Muscle | 0.04 ± 0.01 | 0.06 ± 0.01* | 0.05 ± 0.01 | 0.07 ± 0.03 | 0.07 ± 0.01 | 0.08 ± 0.02 |
| Bone | 0.11 ± 0.02 | 0.41 ± 0.09* | 0.11 ± 0.02 | 0.71 ± 0.08* | 0.15 ± 0.02 | 0.16 ± 0.03 |
| Lymph Nodes | 0.14 ± 0.05 | 0.45 ± 0.24* | 0.15 ± 0.02 | 0.74 ± 0.29* | 0.37 ± 0.30 | 0.25 ± 0.05 |
| Blood | 0.55 ± 0.09 | 0.66 ± 0.13 | 0.43 ± 0.04 | 0.49 ± 0.05* | 0.77 ± 0.15 | 0.92 ± 0.16 |

| | 316 | | 317 | | 318 | |
|---|---|---|---|---|---|---|
| | C57Bl/6 n = 6 | hCX3CR1 KI n = 6 | C57Bl/6 n = 6 | hCX3CR1 KI n = 6 | C57Bl/6 n = 6 | hCX3CR1 KI n = 6 |
| Heart | 0.18 ± 0.02 | 0.34 ± 0.04* | 0.37 ± 0.09 | 0.45 ± 0.08 | 0.22 ± 0.03 | 0.57 ± 0.06* |
| Lungs | 0.56 ± 0.13 | 1.11 ± 0.22* | 0.86 ± 0.29 | 1.42 ± 0.41* | 0.63 ± 0.23 | 0.89 ± 0.25† |
| Liver | 2.12 ± 0.22 | 2.53 ± 0.08* | 3.21 ± 0.53 | 3.49 ± 0.47 | 1.87 ± 0.06 | 1.98 ± 0.25 |
| Spleen | 0.89 ± 0.18 | 2.10 ± 0.25* | 0.77 ± 0.21 | 1.80 ± 0.24* | 0.60 ± 0.06 | 3.63 ± 0.79* |
| Pancreas | 0.09 ± 0.01 | 0.19 ± 0.02* | 0.18 ± 0.03 | 0.28 ± 0.04* | 0.11 ± 0.01 | 0.46 ± 0.07* |
| Left Kidney | 214 ± 32 | 203 ± 20 | 243 ± 9 | 201 ± 25* | 252 ± 34 | 196 ± 40* |
| Right Kidney | 229 ± 33 | 205 ± 22 | 252 ± 15 | 214 ± 22* | 278 ± 28 | 213 ± 42* |
| Brain | 0.01 ± 0.00 | 0.02 ± 0.00* | 0.02 ± 0.01 | 0.03 ± 0.01§ | 0.01 ± 0.00 | 0.03 ± 0.01* |
| Aorta | 0.13 ± 0.03 | 0.16 ± 0.03 | 0.34 ± 0.09 | 0.37 ± 0.09 | 0.27 ± 0.04 | 0.44 ± 0.08* |
| Stomach | 0.16 ± 0.02 | 0.60 ± 0.45* | 0.29 ± 0.07 | 0.70 ± 0.06* | 0.29 ± 0.06 | 1.38 ± 0.38* |
| Small Intestine | 0.37 ± 0.14 | 1.16 ± 0.12* | 0.49 ± 0.12 | 1.92 ± 0.14* | 0.41 ± 0.12 | 3.11 ± 0.36* |
| Large Intestine | 0.31 ± 0.15 | 0.73 ± 0.29* | 0.43 ± 0.22 | 0.62 ± 0.15 | 0.30 ± 0.18 | 1.27 ± 0.12* |
| Muscle | 0.04 ± 0.01 | 0.05 ± 0.01* | 0.09 ± 0.01 | 0.11 ± 0.03 | 0.07 ± 0.01 | 0.08 ± 0.03 |
| Bone | 0.12 ± 0.02 | 0.48 ± 0.10* | 0.20 ± 0.04 | 0.57 ± 0.11* | 0.16 ± 0.04 | 0.77 ± 0.20* |
| Lymph Nodes | 0.12 ± 0.03 | 0.47 ± 0.13* | 0.25 ± 0.06 | 0.70 ± 0.15* | 0.18 ± 0.04 | 1.52 ± 0.32* |
| Blood | 0.46 ± 0.07 | 0.49 ± 0.09 | 0.47 ± 0.16 | 0.53 ± 0.18 | 0.28 ± 0.02 | 0.21 ± 0.02* |

Data are shown as percentage of injected activity per gram tissue (% IA/g; *p < 0.05 C57BL/6 vs. hCX3CR1 KI mice for each VHH domain (ANOVA and Mann-Whitney U-test (same results)); §p < 0.05 on ANOVA, but not Mann-Whitney U-test; †p < 0.05 on Mann-Whitney U-test, but not on ANOVA).

In C57BL/6 mice all VHH domains showed the typical biodistribution of molecules with a molecular weight lower than 60 kDa: fast blood clearance with high renal excretion (Table 10, FIG. 2). At 3 h post-injection, kidney values were higher than 200% IA/g and blood values ranged between 0.21 and 0.92% IA/g. In all other organs and tissues, except liver, values were lower than 1% IA/g at that time point. For the liver, values ranged between 1.31% IA/g for $^{99m}$Tc-CX3CR1BII18E06 and 3.21% IA/g for $^{99m}$Tc-CX3CR1BII317. In hCX3CR1 KI mice, higher uptake of the $^{99m}$Tc-VHH domains in almost all organs and tissues was observed, except for $^{99m}$Tc-VHH domain CX3CR1BII315 (Table 10) consistent with its weaker cell binding.

Although significant, these differences were minor for the following organs: heart, lungs, liver, pancreas, kidneys, brain, aorta and muscles. The difference was more remarkable for spleen, stomach, intestines, bone and lymph nodes, presumably reflecting binding to tissue-resident immune cells in these organs such as macrophages and dendritic cells. The highest specific targeting was observed for the monovalent $^{99m}$Tc-CX3CR1BII66B02 and bivalent $^{99m}$Tc-CX3CR1BII318.

Example 5

Identification of CX3CR1 VHH Domain Binding to Atherosclerotic Plaques in Apo E$^{-/-}$ Mice Fed a High Fat Diet In Vivo Competition Experiments in Mice with Atherosclerotic Disease To show specific targeting of the anti-CX3CR1 VHH domains to atherosclerotic plaques, the hCX3CR1 KI mice were crossed to Apo E$^{-/-}$ mice (The Jackson Laboratory, Bar Harbor, Me., USA) to generate hCX3CR1 KI Apo E$^{-/-}$ mice. The Apo E$^{-/-}$ mouse model provides a robust method to elicit extensive atherosclerotic plaque formation that is grossly similar to the human disease with respect to the site-specific localization of plaque formation, histological composition, and the known risk factors (cholesterol, inflammation, hypertension, etc).

4 week old female ApoE$^{-/-}$ and hCX3CR1 KI ApoE$^{-/-}$ mice were fed a high fat/high cholesterol diet containing 1.5% cholesterol for 16 weeks. Each $^{99m}$Tc-VHH domain was evaluated in six ApoE$^{-/-}$ and six hCX3CR1KI ApoE$^{-/-}$ mice (The monovalent $^{99m}$Tc-VHH domain CX3CR1BII315 was excluded, based on the loss of functionality after $^{99m}$Tc-labeling observed by in vitro cell binding and biodistribution studies in non-diseased mice). A control $^{99m}$Tc-VHH domain cAbBCII10 generated against a bacterial enzyme (Conrath, 2001; Antimicrob. Agents Chemother. 45: 2807) was evaluated in six hCX3CR1 KI ApoE$^{-/-}$ mice. 100 μl of a $^{99m}$Tc-VHH domain solution (61±16 MBq) was injected intravenously via the tail vein. A group of mice were also co-injected with a 100-fold excess of the equivalent unlabeled VHH molecule (referred to as "blocking"). Three hours post-injection, anesthetized animals were placed in prone position in an animal bed along with six $^{57}$Co landmarks and sequentially subjected to pinhole-SPECT and microCT as described in Example 4. After the imaging, animals were euthanized by an overdose of sodium pentobarbital, and tissue and organs were harvested for further ex vivo analysis.

Representative images of the biodistribution of $^{99m}$Tc-CX3CR1BII66B02 and $^{99m}$Tc-CX3CR1BII318 in ApoE$^{-/-}$ and hCX3CR1KI ApoE$^{-/-}$ mice with and without blocking are shown in FIG. 3. Three hours post-injection, high signals were detected in total body SPECT/CT images of the anti-hCX3CR1 $^{99m}$Tc-VHH domains in aortic lesions at the base of the aorta and in the aortic arch in hCX3CR1 KI ApoE$^{-/-}$ mice (white arrows). Specific uptake in aortic lesions and all other organs was suppressed by competition. No specific accumulation was observed in ApoE$^{-/-}$ mice. Similarly, no accumulation was observed in hCX3CR1 mice without disease (Example 4 and FIG. 2).

The ex vivo biodistribution of each VHH domain was evaluated in ApoE$^{-/-}$ and hCX3CR1 KI ApoE$^{-/-}$ mice, as well as in hCX3CR1 KI ApoE$^{-/-}$ mice in the presence of an excess of unlabeled VHH domain. Uptake of hCX3CR1-specific VHH domains related with the SPECT/CT images presented above and was higher in the hCX3CR1KI ApoE$^{-/-}$ mice than in ApoE$^{-/-}$ mice consistent with target expression of CX3CR1 (Table 11). Uptake of VHH domain was blocked by competition with the unlabeled VHH domain. Since the control $^{99m}$Tc-VHH domain cAbBCII10 does not recognize any target in mammalian cells, clearance through the kidneys was observed as with all VHH domains, but $^{99m}$Tc-cAbBCII10 was not taken up by any other organ. The results largely correspond to the biodistribution data obtained in hCX3CR1 KI mice, demonstrating the lack of large differences in biodistribution of anti-hCX3CR1-targeting VHH domains between healthy mice and mice with atherosclerotic disease.

TABLE 11

Ex Vivo VHH domain biodistribution in Apo E$^{-/-}$ mice, Apo E$^{-/-}$hCX3CR1 KI mice and ApoE$^{-/-}$ hCX3CR1 KI mice co-injected with an excess of unlabeled VHH domain

| | Mean ± St. Dev. | | |
|---|---|---|---|
| | ApoE-/-<br>n = 6 | ApoE-/-<br>hCX3CR1<br>KI<br>n = 6 | ApoE-/-<br>hCX3CR1<br>KI + Blocking<br>n = 6 |
| | 18E06 | | |
| Heart | 0.19 ± 0.03 | 0.35 ± 0.09 | 0.10 ± 0.02 |
| Lungs | 0.43 ± 0.11 | 0.90 ± 0.50 | 0.20 ± 0.09 |

TABLE 11-continued

Ex Vivo VHH domain biodistribution in Apo E$^{-/-}$ mice, Apo E$^{-/-}$hCX3CR1 KI mice and ApoE$^{-/-}$ hCX3CR1 KI mice co-injected with an excess of unlabeled VHH domain

| Liver | 1.59 ± 0.22 | 1.51 ± 0.29 | 1.07 ± 0.16 |
|---|---|---|---|
| Spleen | 0.91 ± 0.21 | 1.92 ± 0.44 | 0.76 ± 0.23 |
| Pancreas | 0.15 ± 0.03 | 0.24 ± 0.10 | 0.07 ± 0.03 |
| Kidney L | 214 ± 13 | 167 ± 37 | 98 ± 13 |
| Kidney R | 213 ± 19 | 180 ± 44 | 102 ± 19 |
| Stomach | 0.20 ± 0.04 | 0.80 ± 0.29 | 0.22 ± 0.08 |
| Small intestine | 0.62 ± 0.35 | 1.79 ± 0.58 | 0.35 ± 0.06 |
| Large Intestine | 0.46 ± 0.31 | 0.90 ± 0.35 | 0.26 ± 0.15 |
| Muscle | 0.08 ± 0.01 | 0.07 ± 0.02 | 0.05 ± 0.02 |
| Bone | 0.16 ± 0.02 | 0.31 ± 0.14 | 0.11 ± 0.02 |
| Blood | 0.59 ± 0.08 | 0.42 ± 0.13 | 0.22 ± 0.03 |
| | 66B02 | | |
| Heart | 0.23 ± 0.06 | 0.65 ± 0.14 | 0.12 ± 0.02 |
| Lungs | 0.70 ± 0.30 | 1.48 ± 0.58 | 0.27 ± 0.12 |
| Liver | 1.48 ± 0.60 | 1.63 ± 0.32 | 0.99 ± 0.28 |
| Spleen | 0.74 ± 0.24 | 2.85 ± 0.71 | 0.61 ± 0.20 |
| Pancreas | 0.14 ± 0.04 | 0.46 ± 0.15 | 0.08 ± 0.02 |
| Kidney L | 2.05 ± 35 | 177 ± 8 | 118 ± 19 |
| Kidney R | 227 ± 33 | 181 ± 9 | 124 ± 16 |
| Stomach | 0.23 ± 0.06 | 1.14 ± 0.29 | 0.26 ± 0.13 |
| Small intestine | 1.01 ± 0.97 | 3.09 ± 0.54 | 0.51 ± 0.20 |
| Large Intestine | 0.29 ± 0.11 | 1.69 ± 0.42 | 0.52 ± 0.34 |
| Muscle | 0.08 ± 0.02 | 0.13 ± 0.10 | 0.04 ± 0.01 |
| Bone | 0.17 ± 0.05 | 0.53 ± 0.12 | 0.12 ± 0.04 |
| Blood | 0.65 ± 0.34 | 0.53 ± 0.27 | 0.20 ± 0.07 |
| | 316 | | |
| Heart | 0.26 ± 0.10 | 0.43 ± 0.11 | 0.22 ± 0.15 |
| Lungs | 092 ± 0.61 | 1.18 ± 0.41 | 0.55 ± 0.40 |
| Liver | 7.97 ± 4.69 | 6.25 ± 3.06 | 5.48 ± 1.94 |
| Spleen | 3.23 ± 2.14 | 4.01 ± 1.26 | 2.68 ± 1.36 |
| Pancreas | 0.18 ± 0.05 | 0.25 ± 0.05 | 0.10 ± 0.02 |
| Kidney L | 202 ± 34 | 177 ± 21 | 89 ± 13 |
| Kidney R | 210 ± 40 | 186 ± 27 | 90 ± 12 |
| Stomach | 0.25 ± 0.05 | 0.71 ± 0.10 | 0.18 ± 0.02 |
| Small intestine | 0.54 ± 0.24 | 1.76 ± 0.22 | 0.39 ± 0.04 |
| Large Intestine | 0.25 ± 0.05 | 0.87 ± 0.07 | 0.30 ± 0.11 |
| Muscle | 0.08 ± 0.06 | 0.11 ± 0.03 | 0.05 ± 0.02 |
| Bone | 0.29 ± 0.10 | 0.44 ± 0.13 | 0.21 ± 0.04 |
| Blood | 0.79 ± 0.23 | 0.60 ± 0.08 | 0.30 ± 0.02 |
| | 317 | | |
| Heart | 0.28 ± 0.05 | 0.32 ± 0.04 | 0.17 ± 0.04 |
| Lungs | 0.81 ± 0.21 | 0.95 ± 0.38 | 0.30 ± 0.04 |
| Liver | 2.34 ± 0.50 | 2.09 ± 0.34 | 1.32 ± 0.17 |
| Spleen | 0.49 ± 0.07 | 1.55 ± 0.22 | 0.36 ± 0.06 |
| Pancreas | 0.17 ± 0.02 | 0.25 ± 0.03 | 0.12 ± 0.02 |
| Kidney L | 217 ± 38 | 183 ± 44 | 85 ± 19 |
| Kidney R | 231 ± 57 | 193 ± 48 | 89 ± 16 |
| Stomach | 0.26 ± 0.02 | 0.68 ± 0.12 | 0.22 ± 0.03 |
| Small intestine | 0.43 ± 0.05 | 1.89 ± 0.19 | 0.29 ± 0.04 |
| Large Intestine | 0.29 ± 0.08 | 0.86 ± 0.08 | 0.36 ± 0.09 |
| Muscle | 0.12 ± 0.03 | 0.11 ± 0.01 | 0.09 ± 0.01 |
| Bone | 0.25 ± 0.02 | 0.36 ± 0.08 | 0.18 ± 0.04 |
| Blood | 0.46 ± 0.11 | 0.32 ± 0.04 | 0.25 ± 0.07 |
| | 318 | | |
| Heart | 0.36 ± 0.11 | 0.81 ± 0.24 | 0.21 ± 0.03 |
| Lungs | 1.05 ± 0.34 | 1.05 ± 0.24 | 0.43 ± 0.14 |
| Liver | 1.80 ± 0.20 | 1.77 ± 0.08 | 1.23 ± 0.13 |
| Spleen | 0.70 ± 0.15 | 3.65 ± 0.79 | 0.50 ± 0.07 |

TABLE 11-continued

Ex Vivo VHH domain biodistribution in Apo E$^{-/-}$ mice,
Apo E$^{-/-}$hCX3CR1 KI mice and ApoE$^{-/-}$ hCX3CR1
KI mice co-injected with an excess of unlabeled VHH domain

| Pancreas | 0.18 ± 0.02 | 0.67 ± 0.12 | 0.12 ± 0.02 |
|---|---|---|---|
| Kidney L | 274 ± 31 | 207 ± 33 | 79 ± 4 |
| Kidney R | 283 ± 41 | 207 ± 31 | 78 ± 14 |
| Stomach | 0.32 ± 0.08 | 1.43 ± 0.29 | 0.26 ± 0.07 |
| Small intestine | 0.63 ± 0.18 | 3.67 ± 0.29 | 0.40 ± 0.07 |
| Large Intestine | 0.32 ± 0.07 | 1.89 ± 0.60 | 0.30 ± 0.12 |
| Muscle | 0.12 ± 0.02 | 0.14 ± 0.02 | 0.10 ± 0.02 |
| Bone | 0.23 ± 0.06 | 0.71 ± 0.10 | 0.18 ± 0.03 |
| Blood | 0.53 ± 0.11 | 0.36 ± 0.07 | 0.28 ± 0.04 |

| | cAbBCII10 Mean ± St. Dev. ApoE-/- hCX3CR1 KI n = 6 |
|---|---|
| Heart | 0.15 ± 0.03 |
| Lungs | 0.88 ± 0.25 |
| Liver | 0.54 ± 0.10 |
| Spleen | 0.30 ± 0.04 |
| Pancreas | 0.11 ± 0.02 |
| Kidney L | 190 ± 17 |
| Kidney R | 201 ± 27 |
| Stomach | 0.29 ± 0.08 |
| Small intestine | 0.30 ± 0.05 |
| Large Intestine | 0.26 ± 0.19 |
| Muscle | 0.06 ± 0.02 |
| Bone | 0.11 ± 0.03 |
| Blood | 0.41 ± 0.08 |

Data are shown as percentage of injected activity per gram tissue (% IA/g).

Identification of Major Sites of Atherosclerosis in Live Animals Via SPECT/CT

Lesion-to-heart ratios were calculated as a read-out to quantitate atherosclerotic lesions in coronary arteries close to heart muscle. It is clear from the dissection analyses and autoradiography that the major sites of plaque formation in the atherosclerotic mice were the aortic root and arch, and that these sites are associated with the highest accumulation of $^{99m}$Tc-CX3CR1BlI66B02. As discussed above and shown in FIG. 3 uptake of $^{99m}$Tc-CX3CR1BlI66B02 in this region is observed in the SPECT/CT images. These signals were further quantified by drawing regions of interest (ROIs) at the aortic root/arch site and expressing them as percentage of injected activity per cm$^3$ (% IA/cm$^3$) (Table 12).

TABLE 12

Uptake of $^{99m}$Tc- VHH domains in aorta segments

| | arch:blood (arch:heart LV) | % IA/cm$^3$ in arch |
|---|---|---|
| 66B02 in ApoE$^{-/-}$hCX3CR1 KI | 3.07 ± 1.51 | 0.32 ± 0.03 |
| 66B02 in ApoE$^{-/-}$ | 1.43 ± 0.36** | 0.15 ± 0.02*** |
| 66B02 in ApoE$^{-/-}$hCX3CR1 KI + excess 66B02 | 1.81 ± 0.38* | 0.05 ± 0.01*** |
| 66B02 in C57BL6 hCX3CR1 KI | 1.50 ± 0.25** | N.A. |

TABLE 12-continued

Uptake of $^{99m}$Tc- VHH domains in aorta segments

| | arch:blood (arch:heart LV) | % IA/cm$^3$ in arch |
|---|---|---|
| 66B02 in WT C57BL6 | 1.19 ± 0.43*** | N.A. |
| cAbBcII10 in ApoE$^{-/-}$hCX3CR1 KI | 1.00 ± 0.21*** | 0.08 ± 0.01*** |

*//*P < 0.05/0.01/0.001 vs. $^{99m}$Tc-CX3CR1BII66B02 in hCX3CR1KI ApoE$^{-/-}$ mice As compared to the targeting group ($^{99m}$Tc-CX3CR1B1166B02 in hCX3CR1KI ApoE$^{-/-}$ mice), the arch signals were 6- to 8-fold lower when tracer binding was blocked by injection of unlabeled 66B02 and 2- to 3-fold lower in the absence of molecular target (ApoE$^{-/-}$ mice). The arch signals of control VHH domain $^{99m}$Tc-cAbBcII10 in hCX3CR1KI ApoE$^{-/-}$ mice were about 4-fold lower than the targeting group. Using CT images, equally-sized regions of interest (ROIs) were drawn over the aortic arch/root and the heart left ventricle (as a measure of blood pool activity). SPECT signals in these ROIs were calculated and expressed as percentage of injected activity per volume (% IA/cm$^3$). These values were used to calculate arch-to-blood ratios. Statistical analysis was performed using a parametric test (ANOVA). P-values<0.05 were considered significant.

Arch-to-blood ratios were calculated by drawing a ROI in the heart left ventricle (LV), as a measurement of blood pool (Table 12). The arch-to-blood ratios in atherosclerotic mice were 2-to 3-fold lower when uptake of $^{99m}$Tc-CX3CR1BII66B02 was blocked by injection of excess unlabeled 66B02 or in the absence of hCX3CR1 expression. A similar significant difference was observed for $^{99m}$Tc-cAbBcII10 or for $^{99m}$Tc-CX3CR1BII66B02 in mice without atherosclerotic disease. The specific uptake of $^{99m}$Tc-CX3CR1BII66B02 and $^{99m}$Tc-CX3CR1BII318 in the atherosclerotic aortic arch and root was clearly visible on SPECT/CT images and demonstrates the utility of CX3CR1 VHH domains as radiotracers for noninvasive imaging of atherosclerotic lesions in live animals.

Ex Vivo Analysis of Aortic Segments

The aorta from each of the mice in the study was carefully excised, cleaned free from adherent tissues and cut in 10 segments. Upon visual examination, each segment was given a score between 0 and 3 (0: 0%, 1: 1-50%, 2: 51-75%, 3: 76-100% of area covered with atherosclerotic lesions). All segments, along with other organs and tissues, were collected, weighed and their radioactivity quantitated. Counts were corrected for background and decay and expressed as percentage of injected activity per gram tissue (% IA/g). Statistical analysis was performed using a parametric test (ANOVA). P-values<0.05 were considered significant. For each animal, autoradiographic images were obtained after overnight exposure of all aorta segments to a dedicated phosphorscreen (Typhoon FLA 7000, GE Healthcare). Images were analysed with ImageQuant (GE Healthcare Biosciences, Pittsburgh, Pa.).

Based on visual inspection of the whole aorta, atherosclerotic lesions were seen to be most prevalent at the root and in the arch of the aorta. These segments generally had a lesion score of 3 or 2. In the abdominal section of the aorta, segments with small individual lesions were alternated with segments without lesions. These segments were scored as 1 and 0, respectively. The scores of the thoracic segments varied between 0 and 2. In all mice and for all conditions, the uptake of a $^{99m}$Tc-VHH domain in a segment was significantly increased for hCX3CR1-specific $^{99m}$Tc-VHH domains in hCX3CR1KI ApoE$^{-/-}$ mice (Table 13).

TABLE 13

Uptake of $^{99m}$Tc-VHH domains in aorta segments

|  | ApoE−/− | | ApoE−/− hCX3CR1 KI | | ApoE−/− hCX3CR1 KI + Blocking | |
| --- | --- | --- | --- | --- | --- | --- |
|  | Mean ± St. Dev. | n | Mean ± St. Dev. | n | Mean ± St. Dev. | n |
| 18E06 | | | | | | |
| Score 0 | 0.34 ± 0.14 | 14 | 0.38 ± 0.15 | 10 | 0.27 ± 0.19 | 10 |
| Score 1 | 0.33 ± 0.09 | 28 | 0.59 ± 0.29 | 33 | 0.22 ± 0.06 | 24 |
| Score 2 | 0.39 ± 0.06 | 8 | 0.63 ± 0.32 | 7 | 0.25 ± 0.10 | 9 |
| Score 3 | 0.46 ± 0.12 | 10 | 1.34 ± 0.70 | 9 | 0.30 ± 0.09 | 9 |
| 66B02 | | | | | | |
| Score 0 | 0.44 ± 0.15 | 13 | 0.65 ± 0.49 | 13 | 0.24 ± 0.11 | 8 |
| Score 1 | 0.44 ± 0.19 | 25 | 0.80 ± 0.30 | 23 | 0.31 ± 0.14 | 23 |
| Score 2 | 0.64 ± 0.24 | 10 | 1.00 ± 0.30 | 8 | 0.41 ± 0.11 | 5 |

TABLE 13-continued

Uptake of $^{99m}$Tc-VHH domains in aorta segments

| Score 3 | 0.72 ± 0.30 | 6 | 2.68 ± 1.03 | 6 | 0.49 ± 0.12 | 5 |
| --- | --- | --- | --- | --- | --- | --- |
| 316 | | | | | | |
| Score 0 | 0.24 ± 0.09 | 20 | 0.25 ± 0.12 | 14 | 0.20 ± 0.17 | 9 |
| Score 1 | 0.24 ± 0.06 | 27 | 0.31 ± 0.13 | 24 | 0.17 ± 0.09 | 27 |
| Score 2 | 0.31 ± 0.05 | 9 | 0.45 ± 0.17 | 18 | 0.19 ± 0.07 | 11 |
| Score 3 | 0.34 ± 0.07 | 8 | 1.29 ± 0.44 | 5 | 0.23 ± 0.00 | 2 |
| 317 | | | | | | |
| Score 0 | 0.43 ± 0.15 | 15 | 0.58 ± 0.44 | 8 | 0.38 ± 0.19 | 10 |
| Score 1 | 0.71 ± 0.27 | 24 | 0.60 ± 0.24 | 23 | 0.45 ± 0.22 | 25 |
| Score 2 | 1.06 ± 0.17 | 7 | 0.91 ± 0.27 | 9 | 0.80 ± 0.13 | 8 |
| Score 3 | 1.05 ± 0.23 | 7 | 1.56 ± 0.40 | 10 | 0.89 ± 0.22 | 6 |
| 318 | | | | | | |
| Score 0 | 0.52 ± 0.17 | 18 | 0.45 ± 0.08 | 11 | 0.35 ± 0.14 | 10 |
| Score 1 | 0.54 ± 0.22 | 24 | 0.60 ± 0.15 | 31 | 0.55 ± 0.48 | 26 |
| Score 2 | 0.91 ± 0.40 | 15 | 1.19 ± 0.40 | 19 | 0.75 ± 0.33 | 18 |
| Score 3 | 1.14 ± 0.42 | 10 | 2.37 ± 0.67 | 7 | 0.93 ± 0.08 | 7 | cAbBCII10

| | ApoE−/− hCX3CR1 KI | |
| --- | --- | --- |
| | Mean ± St. Dev | n |
| Score 0 | 0.26 ± 0.10 | 14 |
| Score 1 | 0.37 ± 0.09 | 22 |
| Score 2 | 0.44 ± 0.11 | 13 |
| Score 3 | 0.52 ± 0.14 | 10 |

Figure 4A:
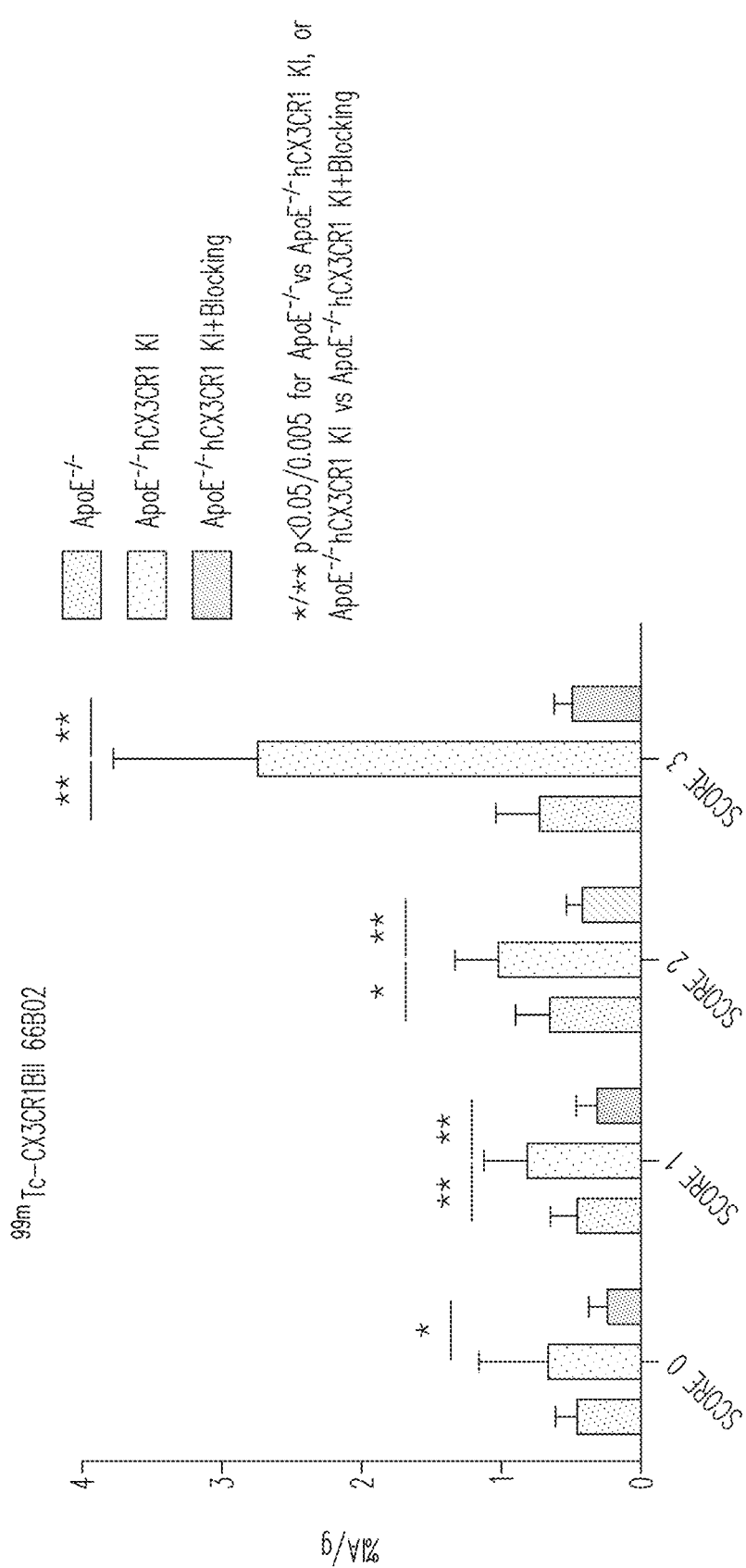
FIGS. 4A and 4B: Ex vivo quantitation of the uptake of $^{99m}$Tc-CX3CR1BII66B02 (FIG. 4A) and $^{99m}$Tc-CX3CR1BII318 (FIG. 4B) into aorta segments from ApoE$^{-/-}$ mice, hCX3CR1 KI ApoE$^{-/-}$ mice and hCX3CR1KI ApoE$^{-/-}$ mice co-administered an excess of unlabeled VHH domain ranked according to lesion score.
Figure 4B:
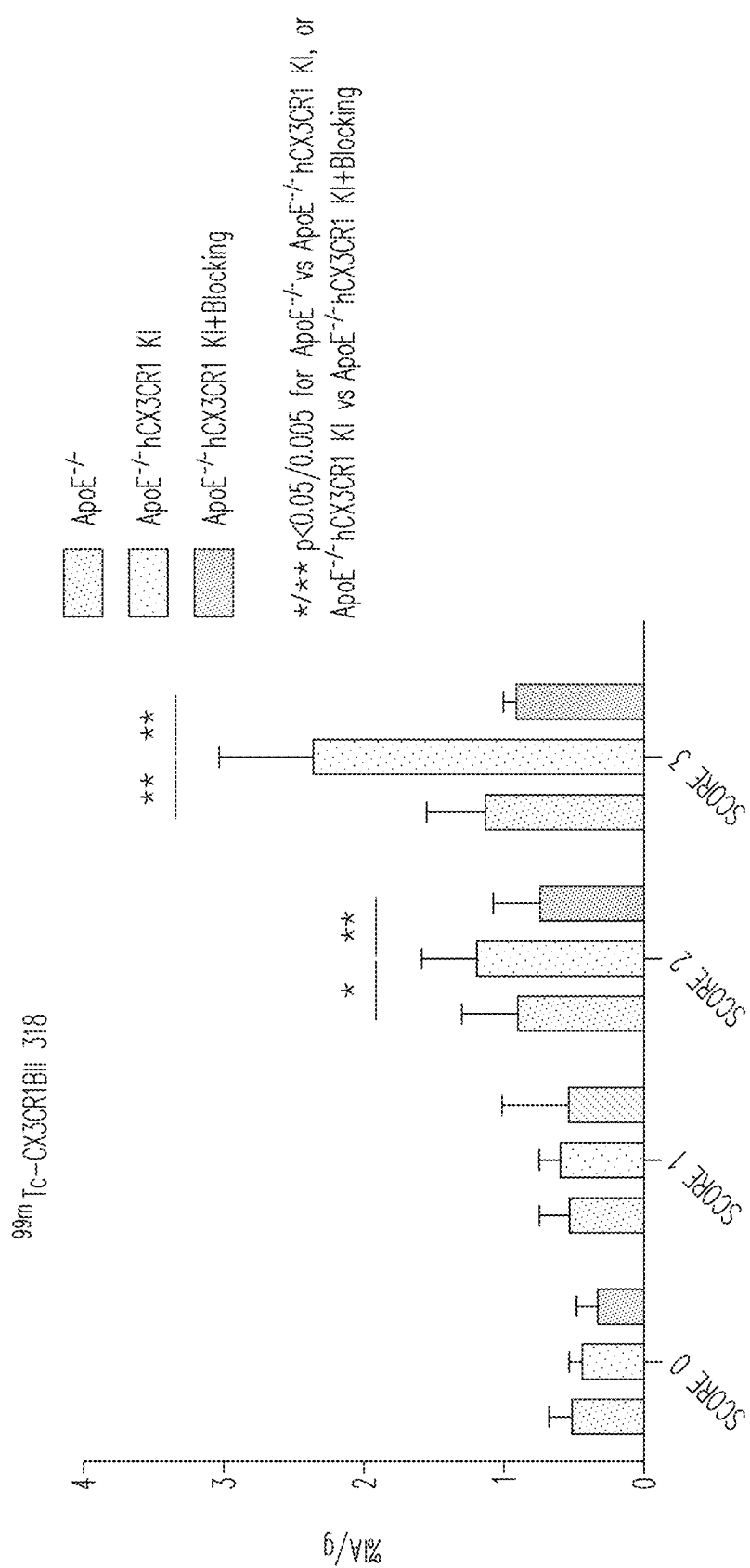

The highest values in segments with score 3 were obtained for the monovalent VHH domain $^{99m}$Tc-CX3CR1BII66B02 and the bivalent VHH domain $^{99m}$Tc-CX3CR1BII318, with average values of 2.68 and 2.37% IA/g respectively (Table 14). Addition of excess unlabeled VHH domains reduced the uptake of the anti-hCX3CR1 $^{99m}$Tc-VHH domains to the level of uptake in the control conditions (anti-hCX3CR1 $^{99m}$Tc-VHH domain in ApoE$^{-/-}$ mice or $^{99m}$Tc-cAbBCII10 in hCX3CR1 KI ApoE$^{-/-}$ mice, FIGS. 4A and 4B) confirming binding specificity. In FIGS. 4A and 4B, for each score, the bars on the left, center and right show the % IA/g found for ApoE$^{-/-}$, ApoE$^{-/-}$ hCX3CR1 KI and ApoE$^{-/-}$ hCX3CR1 KI with blocking mice respectively.

TABLE 14

Uptake of $^{99m}$Tc-VHH domains in aorta segments

| | % IA/g in lesions (score 3) | lesion:normal aorta (score 3:score 0) | lesion:blood (score3:blood) | lesion:heart (score3:blood) |
| --- | --- | --- | --- | --- |
| 66B02 in ApoE$^{-/-}$hCX3CR1 KI | 2.68 ± 1.03 | 4.29 ± 2.07 | 5.63 ± 2.83 | 4.01 ± 1.04 |
| 66B02 in ApoE$^{-/-}$ | 0.72 ± 0.30** | 1.90 ± 1.32* | 1.23 ± 0.68** | 3.03 ± 1.12 |
| 66B02 in ApoE$^{-/-}$hCX3CR1 KI + excess 66B02 | 0.49 ± 0.12** | 2.14 ± 0.49* | 2.45 ± 0.41** | 4.11 ± 0.42 |

*/**P < 0.05/0.01 vs. $^{99m}$Tc-CX3CR1BII66B02 in hCX3CR1KI ApoE$^{-/-}$ mice

Figure 5:
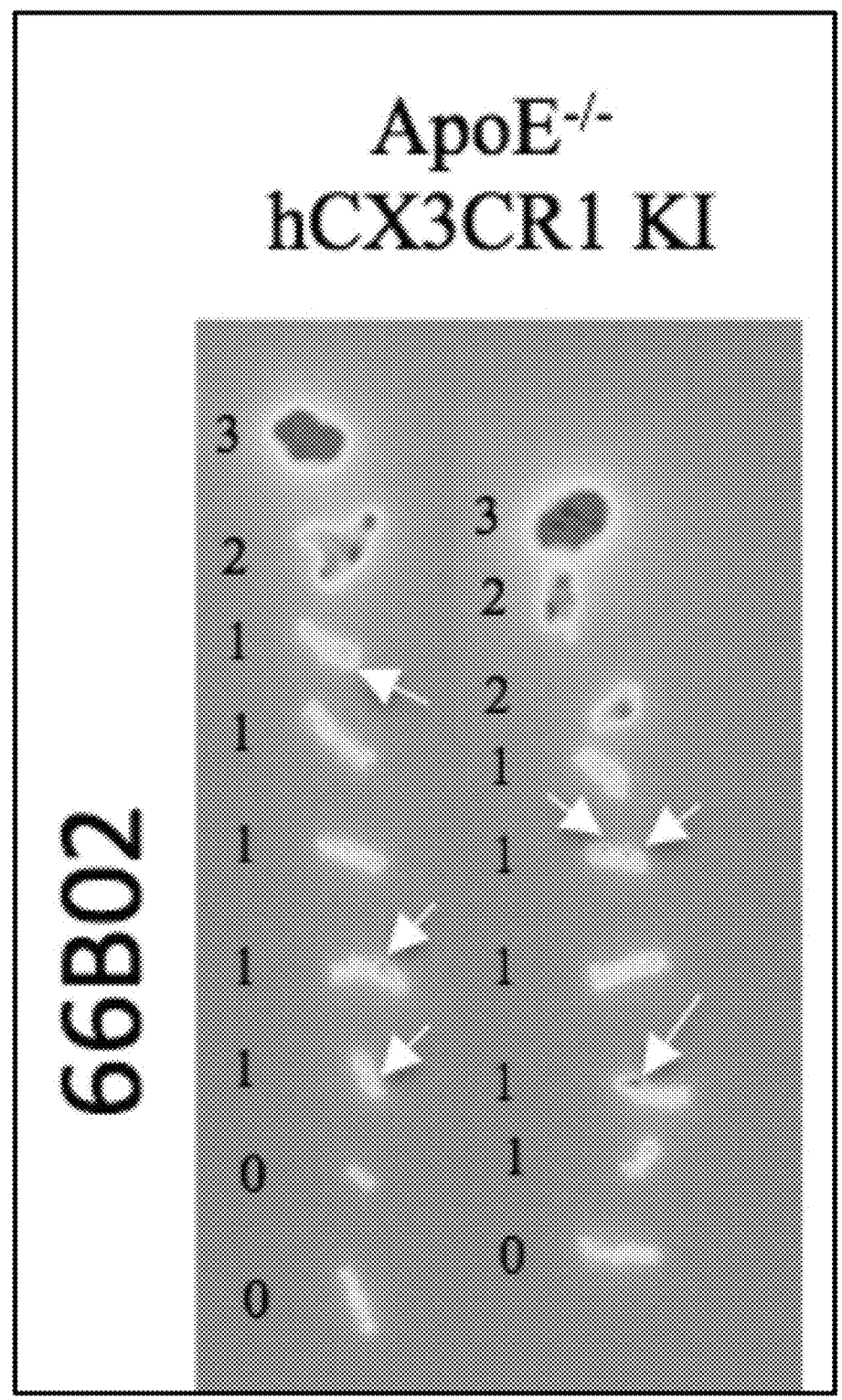
FIG. 5: Representative color-scaled autoradiographic images from isolated aortic segments from $^{99m}$Tc-CX3CR1BII66B02 injected hCX3CR1 KI ApoE$^{-/-}$ mice. White arrows point to small, individual plaques in segments with lesion score 1.

Besides evaluating tracer uptake in individual aortic segments by quantification of lesion weight and radioactive counts, these segments were also exposed to radiosensitive phosphorscreens in order to visualize the spatial distribution of radioactive signals. Elevated uptake of $^{99m}$Tc-CX3CR1B1166B02 was observed in segments with increasing lesion burden in hCX3CR1KI ApoE$^{-/-}$ mice as compared to segments from ApoE$^{-/-}$ mice, or with $^{99m}$Tc-cAbBcII10 in hCX3CR1 KI ApoE$^{-/-}$ mice. $^{99m}$Tc-CX3CR1B1166B02 was shown to bind focally to small plaques in segments with a low lesion score (white arrows in FIG. 5).

We claim:

1. An imaging agent comprising a CX3CR1-targeting polypeptide linked to a detection label, wherein the CX3CR1-targeting polypeptide includes CDR1, CDR2 and CDR3 sequences selected from:

SEQ ID No: 141, 162 and 186, respectively; or
SEQ ID No: 141, 163 and 187, respectively; or
SEQ ID No: 141, 164 and 186, respectively; or
SEQ ID No: 141, 166 and 186, respectively; or
SEQ ID No: 141, 167 and 186, respectively; or
SEQ ID No: 141, 167 and 189, respectively; or
SEQ ID No: 141, 168 and 186, respectively; or
SEQ ID No: 141, 168 and 187, respectively; or
SEQ ID No: 141, 169 and 190, respectively; or
SEQ ID No: 141, 170 and 186, respectively; or
SEQ ID No: 141, 171 and 186, respectively; or
SEQ ID No: 141, 174 and 186, respectively; or
SEQ ID No: 141, 175 and 187, respectively; or
SEQ ID No: 142, 165 and 188, respectively; or
SEQ ID No: 142, 173 and 188, respectively; or
SEQ ID No: 143, 164 and 186, respectively; or
SEQ ID No: 144, 172 and 187, respectively; or
SEQ ID No: 145, 172 and 187, respectively; or
SEQ ID No: 141, 214 and 186, respectively; or
SEQ ID No: 141, 215 and 186, respectively; or
SEQ ID No: 141, 216 and 186, respectively; or
SEQ ID No: 141, 217 and 186, respectively; or
SEQ ID No: 141, 218 and 186, respectively; or
SEQ ID No: 141, 219 and 186, respectively; or
SEQ ID No: 141, 220 and 186, respectively; or
SEQ ID No: 213, 221 and 186, respectively; or
SEQ ID No: 213, 214 and 186, respectively; or
SEQ ID No: 146, 176 and 191, respectively; or
SEQ ID No: 146, 177 and 191, respectively; or
SEQ ID No: 147, 178 and 192, respectively; or
SEQ ID No: 147, 179 and 192, respectively; or
SEQ ID No: 147, 179 and 194, respectively; or
SEQ ID No: 148, 179 and 193, respectively; or
SEQ ID No: 149, 179 and 192, respectively; or
SEQ ID No: 149, 180 and 192, respectively; or
SEQ ID No: 149, 181 and 192, respectively; or
SEQ ID No: 149, 183 and 192, respectively; or
SEQ ID No: 149, 185 and 192, respectively; or
SEQ ID No: 150, 179 and 194, respectively; or
SEQ ID No: 150, 182 and 194, respectively; or
SEQ ID No: 151, 179 and 193, respectively; or
SEQ ID No: 151, 182 and 194, respectively; or
SEQ ID No: 151, 184 and 196, respectively; or
SEQ ID No: 152, 179 and 195, respectively; or
SEQ ID No: 153, 179 and 194, respectively; or
SEQ ID No: 154, 182 and 194, respectively; or
SEQ ID No: 155, 179 and 195, respectively; or
SEQ ID No: 156, 181 and 192, respectively; or
SEQ ID No: 157, 179 and 194, respectively; or
SEQ ID No: 158, 179 and 192, respectively; or
SEQ ID No: 159, 178 and 192, respectively; or SEQ ID No: 160, 179 and 194, respectively; or
SEQ ID No: 161, 179 and 194, respectively;
and wherein the detection label is a radio-isotope.

2. An imaging agent according to claim 1, wherein the CX3CR1-targeting polypeptide is an immunoglobulin single variable domain.

3. An imaging agent according to claim 1, wherein the CX3CR1-targeting polypeptide is a VHH domain.

4. An imaging agent according to claim 1, wherein the CX3CR1-targeting polypeptide includes CDR1, CDR2 and CDR3 sequences selected from:
SEQ ID No: 141, 162 and 186, respectively; or
SEQ ID No: 141, 214 and 186, respectively; or
SEQ ID No: 141, 215 and 186, respectively; or
SEQ ID No: 141, 216 and 186, respectively; or
SEQ ID No: 141, 217 and 186, respectively; or
SEQ ID No: 141, 218 and 186, respectively; or
SEQ ID No: 141, 219 and 186, respectively; or
SEQ ID No: 141, 220 and 186, respectively; or
SEQ ID No: 213, 221 and 186, respectively; or
SEQ ID No: 213, 214 and 186, respectively; or
SEQ ID No: 147, 178 and 192, respectively; or
SEQ ID No: 146, 176 and 191, respectively.

5. An imaging agent according to claim 1, wherein the CX3CR1-targeting polypeptide is a VHH domain having a sequence selected from:
any one of SEQ ID No's: 1-140 or 197-202.

6. An imaging agent according to claim 5, wherein the CX3CR1-targeting polypeptide is a VHH domain having a sequence selected from:
any one of SEQ ID No's: 1, 11, 49, 53, 121-140 or 197-202.

7. An imaging agent according to claim 1, wherein the CX3CR1-targeting polypeptide is bivalent comprising two VHH domains, which may be identical or different, covalently linked by a linker peptide, wherein the bivalent CX3CR1-targeting polypeptide is selected from:
any one of SEQ ID No's: 203-212, 222 or 223.

8. An imaging agent according to claim 7, wherein the sequence of the bivalent CX3CR1-targeting polypeptide is selected from:
any one of SEQ ID No's: 208, 222 or 223.

9. An imaging agent according to claim 1, wherein the detection label is selected from $^{99m}$Tc, $^{111}$In, $^{123}$I, $^{201}$Tl, $^{133}$Xe, $^{11}$C, $^{64}$Cu, $^{18}$F, $^{68}$Ga, $^{13}$N, $^{15}$O, $^{82}$Rb, $^{124}$I and $^{89}$Zr.

10. An imaging agent according to claim 9, wherein the detection label is selected from $^{99m}$Tc and $^{68}$Ga.

11. An in vivo method for diagnosing a disease characterized by increased expression of CX3CR1 in a subject, the method comprising:
a) administering to a subject an imaging agent according to claim 1; and
b) detecting a higher level of binding of the imaging agent in affected tissue in the subject as compared to undiseased tissue.

12. The method according to claim 11, wherein the disease is selected from cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, pancreatitis, vasculitis, rheumatoid arthritis, osteoarthritis, allograft rejection, systemic sclerosis, neurodegenerative disorders, demyelinating disease, multiple sclerosis (MS), Alzheimer's disease, COPD, asthma, neuropathic pain, inflammatory pain, and cancer.

13. The method according to claim 11, wherein the disease is atherosclerosis.

14. The method according to claim 11 wherein the method for detecting the binding of the imaging agent is selected from:
a) single photon emission computed tomography; and
b) positron emission tomography.

15. The method according to claim 11 wherein the method for detecting the binding of the imaging agent is positron emission tomography.

16. The method according to claim 11, wherein the subject is a human.

* * * * *